(12) United States Patent
Singh et al.

(10) Patent No.: US 11,098,306 B1
(45) Date of Patent: Aug. 24, 2021

(54) PROMOTERS AND USES THEREOF

(71) Applicant: National Technology & Engineering Solutions of Sandia, LLC, Albuquerque, NM (US)

(72) Inventors: Seema Singh, Clarksburg, MD (US); Arul Mozhy Varman, Chandler, AZ (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 16/711,146

(22) Filed: Dec. 11, 2019

Related U.S. Application Data

(60) Provisional application No. 62/778,545, filed on Dec. 12, 2018.

(51) Int. Cl.
*C12N 15/11* (2006.01)
*C12P 7/24* (2006.01)
*C12N 15/70* (2006.01)

(52) U.S. Cl.
CPC .............. *C12N 15/11* (2013.01); *C12N 15/70* (2013.01); *C12P 7/24* (2013.01); *C12N 2840/002* (2013.01)

(58) Field of Classification Search
CPC .. C12N 15/11; C12N 15/70; C12N 2840/002; C12P 7/24
See application file for complete search history.

(56) References Cited

U.S. PATENT DOCUMENTS

| | | |
|---|---|---|
| 7,485,343 B1 | 2/2009 | Branson et al. |
| 8,481,974 B1 | 7/2013 | Davis et al. |
| 9,765,044 B2 | 9/2017 | Socha et al. |
| 10,112,916 B2 | 10/2018 | Sathitsuksanoh et al. |
| 10,155,735 B2 | 12/2018 | Socha et al. |
| 10,208,076 B2 | 2/2019 | Singh et al. |
| 10,233,292 B2 | 3/2019 | Singh et al. |
| 10,240,180 B2 | 3/2019 | Northen et al. |
| 2012/0225797 A1 | 9/2012 | Northen et al. |
| 2013/0183739 A1 | 7/2013 | Singh et al. |
| 2015/0322214 A1 | 11/2015 | Singh et al. |
| 2016/0031843 A1 | 2/2016 | Socha et al. |
| 2016/0122379 A1 | 5/2016 | Singh et al. |
| 2016/0176838 A1 | 6/2016 | Sathitsuksanoh et al. |
| 2016/0376564 A1 | 12/2016 | Strachan et al. |
| 2017/0349561 A1 | 12/2017 | Socha et al. |
| 2017/0349617 A1 | 12/2017 | Sun et al. |
| 2017/0369918 A1 | 12/2017 | Sun et al. |
| 2018/0305773 A1 | 10/2018 | Abudayyeh et al. |
| 2018/0346938 A1 | 12/2018 | Xu et al. |
| 2018/0355392 A1 | 12/2018 | Ramakrishnan et al. |
| 2019/0062293 A1 | 2/2019 | Sathitsuksanoh et al. |
| 2019/0062519 A1 | 2/2019 | Dutta et al. |
| 2019/0136281 A1 | 5/2019 | Gladden et al. |
| 2019/0153011 A1 | 5/2019 | Singh et al. |
| 2019/0263748 A1 | 8/2019 | Dutta et al. |
| 2019/0292572 A1 | 9/2019 | Ramakrishnan et al. |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Jha et al., A microbial sensor for organophosphate hydrolysis exploiting an engineered specificity switch in a transcription factor. Nuc. Acids. Res., 2016, vol. 44(17): 8490-8500. (Year: 2016).*
Jha et al., A protocatechuate biosensor for Pseudomonas putida KT2440 via promoter and protein evolution. Metabol. Eng. Commun., 2018, vol. 6: 33-38. (Year: 2018).*
Petersen et al., Transcriptional response elements in promoter of CYP6B1, and insect P450 gene regulated by plant chemicals. Biochim. Biophys. Acta., 2003, vol. 1619: 269-282. (Year: 2003).*
Seffernick et al., Melamine deaminase and Atrazine chlorohydrolase: 98 percent identical but functionally different. J. Bacteriol., 2001, vol. 183 (8): 2405-2410. (Year: 2001).*
Varman et al., Hybrid promoter engineering towards the construction of self-inducible systems for microbial lignin valorization. SANDIA National Lab., Report No. SAND2016-7801J, 2016, pp. 1-37. (Year: 2016).*
Vogne., Characterization of putative effector interaction site of the regulatory HbpR protein from Pseudomonas azelaica by site-directed mutagenesis. PLoS One., 2011, Vo. 6(2), e16539, pp. 1-12. (Year: 2011).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Ajikumar PK at al., "Isoprenoid pathway optimization for taxol precursor overproduction in *Escherichia coli*" Science 2010;330(6000)70-4.
Akerlund T et al., "Analysis of cell-size and DNA content in exponentially growing and stationary-phase batch cultures of *Escherichia coli*," *J. Bacteriol.* 1995;177(23):6791-7.
Alper H et al., "Tunic genetic control through promoter engineering," *Proc. Nat'l Acad. Sci. USA* 2005;102(36):12678-83 (correction in *Proc. Nat'l Acad. Sci. USA* 2006;103(8):3006-7).
Balzer S et al., "A comparative analysis of the properties of regulated promoter systems commonly used for recombinant gene expression in *Escherichia coli*" Microb. Cell Fact. 2013;12:26 (14 pp.).

(Continued)

*Primary Examiner* — Ganapathirama Raghu
(74) *Attorney, Agent, or Firm* — Helen S. Baca; Medley, Behrens & Lewis, LLC

(57) ABSTRACT

The present invention relates to synthetic promoters, as well as expression cassettes, and recombinant scaffolds, and methods thereof. In particular embodiments, the synthetic promoter is inducible by one or more chemical compounds present during lignin depolymerization.

18 Claims, 12 Drawing Sheets
Specification includes a Sequence Listing.

(56) References Cited

OTHER PUBLICATIONS

Baneyx F et al., "Recombinant protein folding and misfolding in *Escherichia coli*," *Nat. Biotechnol.* 2004;22(11):1399-408.

Blazeck J et al. "Controlling promoter strength and regulation in *Saccaromyces cerevisiae* using synthetic hybrid promoters," *Biotechnol. Bioeng.* 2012;109(11):2884-95.

Blazeck et al., "Promoter engineering: recent advances in controlling transcription at the most fundamental level," *Biotechnol. J.* 2013 8(1):46-58.

Blazeck J et al., "Tuning gene expression in *Yarrowia lipolytica* by a hybrid promoter approach," *Appl. Environ. Microbiol.* 2011;77(22):7905-14.

Brosius J et al. "Spacing of the -10 and -35 regions in the tac promoter: effect on its in vivo activity," *J. Biol. Chem* 1985;260(6):3539-41.

Bruijnincx PCA et al., "Biomass conversion: lignin up for breakdown" *Nat. Chem.* 2014;6(12):1035-6.

Bugg TDH et al., "Pathways for degradation of lignin in bacteria and fungi," *Nat. Prod. Rep.* 2011;28(12):1883-96.

Chen Y et al , "Kraft lignin biodegradation by *Novosphingobium* sp. B-7 and analysis of the degradation process," *Bioresour. Technol.* 2012;123:682-5.

Chou CH et al., "Characerization of a pH-inducible promoter system for high-level expression of recombinant proteins in *Escherichia coli*" *Biotechnol. Bioeng.* 1995;47(2):187-92.

Chou HH et al., "Programming adaptive control to evolve increased metabolite production," *Nat. Commun.* 2013;4:2595 (8 pp.).

Chubukov V et al., "Synthetic and systems biology for microbial production of commodity chemicals,"*NPJ Syst. Biol. Appl.* 2016;2:16009 (11 pp.).

Cotana F et al., "Lignin as co-product of second generation bioethanol production from ligno-cellulosic biomass,"*Energy Procedia* 2014;45:52-60.

Davis RW et al., "Multiplex fluorometric assessment of nutrient limitation as a strategy for enhanced lipid enrichment and harvesting of *Neochloris oleoabundans*," *Bioteohnol. Bioeng.* 2012;109(10):2503-12.

De Mey M et al., "Construction and model-based analysis of a promoter library for *Escherichia coli*; an indispensable tool for metabolic engineering," *BMC Biotechnol.* 2007;7:34 (14 pp.).

De Boer HA et al., "The tac promoter: a functional hybrid derived from the trp and lac promoters,"*Proc. Nat'l Acad. Sci. USA* 1983;80(1)21-5.

Dinkelmann M et al., "Expanding fluorescence detection options with the Accuri® C6 Flow Cytometer® System," *Nat. Methods* 2010;7(9):768 (2 pp.).

Duan J et al., "Biodegradation of kraft lignin by a newly isolated anaerobic bacterial strain *Acetoanaerobium* sp. WJDL-Y2," *Lett. Appl. Microbiol.* Lett. Appl. Microbiol. 2016;62(1):55-62.

Dunn MA et al., "Identification of promoter elements in a low-temperature-responsive gene (blt4.9) from barley (*Hordeum vulgare* L.)," *Plant Biol.* 1998;38(4):551-64.

Gilman J et al., "Synthetic promoter design for new microbial chassis," *Biochem. Soc. Trans.* 2016;44:731-7.

Hannig G et al., "Strategies for optimizing heterologous protein expression in *Escherichia coli*," *Trends Biotechnol.* 1998;16(2)54-60.

Harley CB et al., "Analysis of *Escherichia coli* promoter sequences," *Nucl. Acids Res.* 1987;15;2340-61.

Haugen SP et al., "Advances in bacterial promoter recognition and its control by factors that do not bind DNA,"*Nat. Rev. Microbiol.* 2008;6:507-19.

Harris EE et al., "Reaction of hardwood lignin with hydrogen," *J. Am. Chem. Soc.* 1938;60(6):1467-70.

Haugen SP et al., "Advances in bacterial promoter recognition and its control by factors that do not bind DNA," *Nat. Rev. Microbiol.* 2008;6(7):507-19.

Higuchi Y et al., "Bacterial catabolism of β-hydroxypropiovanillone and β-hydroxypropiosyringone produced in the reductive cleavage of arylglycerol-β-aryl ether in lignin," *Appl. Environ. Microbiol.* 2018:84:e02670 (21 pp.).

Ho JCH et al., "An improved whole-cell biosensor for the discovery of lignin-transformlnq enymes in functional matagenomic screens," *ACS Synth Biol.* 2018;7(2):392-8.

Ho JCH et al., Supplementary Information for "An improved whole-cell biosensor for the discovery of lignin-transforming enzymes in functional metagenomic screens," *ACS Synth. Biol.* 2018;7(2):392-8 (20 pp.).

Jensen PR et al., "The sequence of spacers between the consensus sequences modulates the strength of prokaryotic promoters," *Appl. Environ. Microbiol.* 1998:64(1):82-7.

Jiménez Ji et al., "Chapter 35: A Genomic View of the Catabolism of Aromatic Compounds in *Pseudomonas*," in *Handbook of Hydrocarbon and Lipid Microbiology* (Timmis KN, ed.), Spinger-Verlag Berlin Heidelberg, 2010, pp. 1297-325.

Jiménez Ji et al., "Genomic analysis of the aromatic cataboilc pathways from *Pseudomonas putida* KT2440," *Environ. Microbiol.* 2002;4(12):824-41.

Jung DH et al., "Production of p-hydroxybenzoic add from p-coumaric acid by *Burkholderia glumae* BGR1," *Biotechnol. Bioeng.* 2016;113(7):1493-503.

Juven-Gershon T et al., "Rational design of a super core promoter that enhances gene expression," *Nat. Methods* 2006;3(11):917-22.

Kamimura N. et al., "Bacterial catabolism of lignin-derived aromatics: new findings in a recent decade," *Environ Microbiol Rep.* 2017;9:(6):679-705.

Know O et al., "Strategies for production of active eukaryotic proteins in bacterial expression system," *Asian Pac. J. Trop. Biomed.* 2012;2(2):159-62.

Lee BR et al., "Utilization of *Escherichia coli* tac promoter in *Bacillus subtilis*," *Biotechnol. Lett.* 1990;12(12):925-30.

Lee JW et al., "Systems metabolic engineering of microorganisms for natural and non-natural chemicals," *Nat. Chem. Biol.* 2012;8(6):536-46.

Madzak C et al., "Helerologous protein expression and secretion in the non-conventional yeast *Yarrowia lipolytica*: a review," *J. Biotechnol.* 2004;109(1-2):63-81.

Makrides SC, "Strategies for achieving high-level expression of genes in *Escherichia coli*," Microbiol. Rev. 1996;60(3):512-38.

Masai E et al., "Characterization of *Sphingomonas paucimobilis* SYK-6 genes invloved in degradation of lignin-related compounds," *J. Ind. Microbiol. Biotechnol.* 1999;23(4-5):364-73.

Masai E et al., "Complete genome sequence of *Sphingobium* sp. strain SYK-6, a degrader of lignin-derived biaryls and monoarlys," *J. Bacteriol.* 2012;194:534-5.

Mnich E et al., "Degradation of lignin β-aryl ether unites in *Arabidopsis thaliana* exprissing LigG, LigF and LigG from *Sphingomonas paucimobilis* SYK-6," *Plant Biotechnol. J.* 2017;15(5):581-93.

Nevoigt E et al., "Engineering promoter regulation," *Biotechnol. Bioeng.* 2007;96(3)550-8.

Nguyen TTM et al., "The ADH7 promoter of *Saccharomyces cerevisiae* is vanillin-inducible and enables mRNA translation under severe vanillin stress," *Front. Microbiol.* 2015;6:1390 (11 pp.).

Oasmaa A et al., "Catalytic hydrotreating of lignin with water-soluble molybdenum catalyst," *Energy Fuels* 1993;7(3):426-9.

Overtom TW, "Recombinant protein production in bacterial hosts," *Drug Discov. Today* 2014;19(5):590-601.

Oxer MD et al., "High level heterologous expression in *Escherichia coli* using the anaerobically-activated nirB promoter," *Nucleic Acids Res.* 1991;19(11):2869-92.

Pribnow D. "Bacteriophage T7 early promoters: nucleotide sequences of two RNA polymerase binding sites," *J. Mol. Biol.* 1975;99(3):419-43.

Pribnow D, "Nucleotide sequene of an RNA polymerase binding site at an early T7 promoter," *Proc. Nat'l Acad. Sci. USA* 1975;72(3):784-8.

Raj A et al., "Identification of low molecular weight aromatic compounds by gas chromatography-mass spectromerty (GC-MS)

(56) References Cited

OTHER PUBLICATIONS from kraft lignin degradation by three *Bacillus* sp.," *Int. Biodeterior. Biodegradation* 2007;59(4):292-6.

Reiter J et al., "Enzymatic cleavage of lignin β-O-4 aryl ether bonds via net internal hydrogen transfer," *Green Chem.* 2013;15(15):1373-81.

Rosini E et al., "Cascade enzymatic cleavage of the β-O-4 linkage in a lignin model compound," *Catal. Sci. Technol.* 2016;6:2195-205.

Ross W et al., "*Escherichia coli* promoters with UP elements of different strengths: modular structure of bacterial promoters," *J. Bacteriol.* 1998;180(20):5375-83.

Sainsbury PD et al., "Breaking down lignin to high-value chemicals: the conversion of lignocellulose to vanillin in a gene deletion mutant of *Rhodococcus jostii* RHA1," *ACS Chem. Biol.* 2013;8(10):2151-6.

Salvachúa D et al., "Towards lignin consolidated bioprocessing: simultaneous lignin depolymerization and product generation by bacteria," *Green Chem.* 2015;17(11):4951-67.

Singh S et al., "Development and demonstration of an integrated biofuels and chemicals production platform based on ionic liquids," *Sandia Report No. SAND2015-1904C*, 2015 (1 p.).

Singh S et al., "Understanding and regulation of microbiol lignolysis for renewable platform chemicals," *Sandia Report No. SAND2014-0453*, 2014 (33 pp.).

Strachan CR et al., "Metagenomic scaffolds enable combinatorial lignin transformation," *Proc. Nat'l Acad. Sci. USA* 2014;111(28):10143-8.

Strachan CR et al., Supporting information for "Metagenomic scaffolds enable combinatorial lignin transformation," *Proc. Nat'l Acad. Sci. USA* 2014;111(28):10143-8 (15 pp.).

Sun J et al., "Integrated process for ethanol production from lignocellulosic biomass," *Sandia Report No. SAND2016-4626PE*, 2016 (1 p.).

Terpe K, "Overview of bacterief expression systems for heterologous protein production: from molecular and biochemical fundamentals to commercial systems," *Appl. Microbiol. Biotechnol.* 2006;72:211-22.

Tornøe J et al., "Generation of a synthetic mammalian promoter library by modifiation of sequences spacing transcription factor binding sites," *Gene* 2002;297(1-2):21-32.

Tracy BP et al., "Flow cytometry for bacteria: enabling metabolic engineering, synthetic biology and the elucidation of complex phenotypes," *Curr. Opin. Biotechnol.* 2010;21(1):85-99.

Varanasi P et al., "Survey of renewable chemicals produced from lignocellulosic biomass during ionic liquid pretreatment," *Biotechnol. Biofuels* 2013;6:14 (9 pp.)

Vardon DR et al., "Adipic acid production from lignin," *Energy Environ. Sci.* 2015;8(2):617-28.

Varman AM et al., "Metabolic egineering and synthetic biology for the renewable production of fuels and chemicals," *Sandia Report No. SAND2016-11725C*, 2016 (1 p.).

Varman AM et al., "Understanding and engineering microbial ligninolysis for chemical production," *Sandia Report No. SAND2016-7679D*, 2016 (1 p.).

Varman AM et al., "Decoding how a soil bacterium extracts building blocks and metabolic energy from ligninolysis provides road map for lignin valorization," *Proc. Nat'l Acad. Sci. USA* 2016;113(40):E5802-11.

Varman AM et al., Supplementary Information for "Decoding how a soil bacterium extracts building blocks and metabolic energy from ligninolysis provides road map for lignin valorization," *Proc. Nat'l Acad. Sci. USA* 2016;113(40):E5802-11 (23 pp.).

Varman AM et al., "Hybrid phenolic-inducible promoters towards construction of self-inducible systems for microbial lignin valorization," *Biotechnol. Biofuels* 2018;11:182 (13 pp.).

Varman AM et al., "Metabolic engineering of *Synechocystis* sp. strain PCC 6803 for isobutanol production," *Appl. Environ. Microbiol.* 2012;79(3):908-14.

Varman AM at al., Electronic Supporting Information for "Hybrid phenolic-inducible promoters towards construction of self-inducible systems for microbial lignin valorization," *Biotechnol. Biofuels* 2018;11:182 (9 pp.).

Villar JC et al., "Oxidation of hardwood kraft-lignin to phenolic derivatives with oxygen as oxidant," *Wood Sci. Technol.* 2001;35(3):245-55.

Voitl T et al., "Oxidation of lignin using aqueous polyoxometalates in the presence of alcohols," *ChemSusChem* 2008;1(8-9):763-9.

Wang W et al., "Efficient, environmentally-friendiy and specific valorization of lignin: promising role of non-radical lignolytic enzymes," *World J. Microbiol. Biotechnol.* 2017;33(6):125 (14 pp.).

Wardak Z et al., "Microbial production of a precursor for biodegradable plastic," *Sandia Report No. SAND2017-7660D*, 2017 (1 p.).

White RH, "Effect of lignin content and extractives on the higher heating value of wood," *Wood Fiber Sci.* 1987;19(4):446-52.

Wu W et al., "Lignin valorization: two hybrid biochemical routes for the converston of polymeric lignin into value-added chemicals," *Sci. Rep.* 2017;7:8420 (13 pp.).

Wu W et al., "Toward engineering *Escherichia coli* with an autoregulatory system for lignin valorization," *Proc. Nat'l Acad. Sci., USA* 2018;115(12):2970-5.

Wu W et al., Supporting Information for "Toward engineering *Escherichia coli* with an autoregulatory system for lignin valorization," *Proc. Nat'l Acad. Sci. USA* 2018;115(12):2970-5 (4 pp.).

Xia Q et al. "Direct hydrodeoxygenation of raw woody biomass into liquid alkanes," *Nat. Commun.* 2016;7:11162 (10 pp.).

Xiang Q et al., "Production of oxychemicals from precipitated hardwood lignin," *Appl. Biochem. Biotechnol.* 2001;91(1):71-80.

Yadav VG et al., "The future of metabolic engineering and synthetic biology: towards a systematic practice," *Metab. Eng.* 2012;14(3)233-41.

Zhang F et al., "Design of a fuels derived sensor-regulator system for production of chemicals and fuels derived from fatty adds," *Nat. Biotechnol.* 2012;30(4):354-9.

\* cited by examiner

```
gaatcatttttctaaaacaataca tttact ttatttgtcactgtcgt        tactat atcggctgaaattaatgaggtcataccaaat (SEQ ID NO:1)

gaatcatttttctaaaacaataca tttgac aattaatcat--cggctcg      tataat gatcggctgaaattaatgaggtcataccaaat (SEQ ID NO:2)
gaatcatttttctaaaacaataca tttgac aattaatcatc-cggctcg      tataat gatcggctgaaattaatgaggtcataccaaat (SEQ ID NO:3)
gaatcatttttctaaaacaataca tttgac aattaatcatcgcggctcg      tataat gatcggctgaaattaatgaggtcataccaaat (SEQ ID NO:4)
         10          20         30         40          50          60         70
gaatcatttttctaaaacaataca tttgac aattaatcatnncggctcg      tataat natcggctgaaattaatgagg            (SEQ ID NO:5)
naammnttttnnnaaannnnnnn   tttgac aattaatcatnncggctcg      tataat natcggctgaaattaatgagg            (SEQ ID NO:6)
naanhdwttthhaaaanmnnnmn   tttgac aattaatcatnncggctcg      tataat natcggctgaaattaatgagg            (SEQ ID NO:7)
naawtwttttnnaaammnnnnn    tttgac aattaatcatnncggctcg      tataat natcggctgaaattaatgagg            (SEQ ID NO:8)
naawtwttttnnaaammnnmn     tttrmy aattaatcatnncggctcg      taywat natcggctgaaattaatgagg            (SEQ ID NO:9)
```

FIG. 11

|  | Sequence | SEQ ID NO: |
|---|---|---|
| Exemplary UP elements | gaatcatttttctaaaacaataca | 10 |
|  | naannnntttttnnnaaaannnnnnn | 11 |
|  | naanhdnttttthhaaaannnnnnn | 12 |
|  | naanhdnttttthhaaaannnnnnn | 13 |
|  | naanhdwttttthhaaaannnnnnn | 14 |
|  | naawwtwttttnnaaaannnnnnn | 15 |
|  | aannnntttttnnnaaa | 16 |
|  | aanhdnttttthhaaaa | 17 |
|  | aanhdwttttthhaaaa | 18 |
|  | aawwtwttttnnaaaa | 19 |
|  | nnnaannnnttttnnnaaaannn | 20 |
|  | nnaaawwtwttttnnaaaannn | 21 |
| Exemplary -35 elements | tttact | 22 |
|  | tttgac | 23 |
|  | tttrmy | 24 |
|  | tttnnn | 25 |
| Exemplary variable elements | aattaatcatcggctcg | 26 |
|  | aattaatcatcgactag | 27 |
|  | aattaatcatcgaactag | 28 |
|  | aattaatcatccggctcg | 29 |
|  | aattaatcatcgcggctcg | 30 |
|  | aattaatcatnncgrctmg | 31 |
|  | aattaatcatnncggctcg | 32 |
|  | aattaatcatnncgnctng | 33 |
| Exemplary -10 elements | tactat | 34 |
|  | tataat | 35 |
|  | taywat | 36 |
|  | tannat | 37 |
| Exemplary DOWN elements | gatcggctgaaattaatgaggtcatacccaaat | 38 |
|  | natcggctgaaattaatgagg | 39 |
|  | nttgttggcataattaa | 40 |
|  | ncagcaaatctgtatat | 41 |
|  | gtgtggaattgtg | 42 |

FIG. 12

SEQUENCE LISTING

```
<160> NUMBER OF SEQ ID NOS: 55

<210> SEQ ID NO 1
<211> LENGTH: 85
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(85)
<223> OTHER INFORMATION: t, if present, may be u

<400> SEQUENCE: 1
gaatcatttt tctaaaacaa tacatttact ttatttgtca ctgtcgttac tatatcggct      60
gaaattaatg aggtcatacc caaat                                            85

<210> SEQ ID NO 2
<211> LENGTH: 86
```

```
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(86)
<223> OTHER INFORMATION: t, if present, may be u

<400> SEQUENCE: 2
gaatcatttt tctaaaacaa tacatttgac aattaatcat cggctcgtat aatgatcggc     60
tgaaattaat gaggtcatac ccaaat                                         86

<210> SEQ ID NO 3
<211> LENGTH: 87
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(87)
<223> OTHER INFORMATION: t, if present, may be u

<400> SEQUENCE: 3
gaatcatttt tctaaaacaa tacatttgac aattaatcat ccggctcgta taatgatcgg     60
ctgaaattaa tgaggtcata cccaaat                                        87

<210> SEQ ID NO 4
<211> LENGTH: 88
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(88)
<223> OTHER INFORMATION: t, if present, may be u

<400> SEQUENCE: 4
gaatcatttt tctaaaacaa tacatttgac aattaatcat cgcggctcgt ataatgatcg     60
gctgaaatta atgaggtcat acccaaat                                       88

<210> SEQ ID NO 5
<211> LENGTH: 76
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(76)
<223> OTHER INFORMATION: t, if present, may be u
<220> FEATURE:
<221> NAME/KEY: misc_feature
<222> LOCATION: (41)..(41)
<223> OTHER INFORMATION: any nucleic acid or absent (e.g., c or absent)
<220> FEATURE:
<221> NAME/KEY: misc_feature
<222> LOCATION: (42)..(42)
<223> OTHER INFORMATION: any nucleic acid or absent (e.g., g or absent)
<220> FEATURE:
<221> NAME/KEY: misc_feature
<222> LOCATION: (56)..(56)
<223> OTHER INFORMATION: any nucleic acid or absent (e.g., g or absent)

<400> SEQUENCE: 5
gaatcatttt tctaaaacaa tacatttgac aattaatcat nncggctcgt ataatnatcg     60
```
gctgaaatta atgagg                                                          76

<210> SEQ ID NO 6
<211> LENGTH: 76
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: any nucleic acid or absent (e.g., g or absent)
<220> FEATURE:
<221> NAME/KEY: misc_feature
<222> LOCATION: (1)..(76)
<223> OTHER INFORMATION: t, if present, may be u
<220> FEATURE:
<221> NAME/KEY: misc_feature
<222> LOCATION: (4)..(4)
<223> OTHER INFORMATION: any nucleic acid or absent (e.g., t, u, w, or absent)
<220> FEATURE:
<221> NAME/KEY: misc_feature
<222> LOCATION: (5)..(5)
<223> OTHER INFORMATION: any nucleic acid or absent (e.g., c, h, w, or absent)
<220> FEATURE:
<221> NAME/KEY: misc_feature
<222> LOCATION: (6)..(6)
<223> OTHER INFORMATION: any nucleic acid or absent (e.g., a, t, u, d, or absent)
<220> FEATURE:
<221> NAME/KEY: misc_feature
<222> LOCATION: (7)..(7)
<223> OTHER INFORMATION: any nucleic acid or absent (e.g., t u, w, or absent)
<220> FEATURE:
<221> NAME/KEY: misc_feature
<222> LOCATION: (12)..(12)
<223> OTHER INFORMATION: any nucleic acid or absent (e.g., c, h, or absent)
<220> FEATURE:
<221> NAME/KEY: misc_feature
<222> LOCATION: (13)..(13)
<223> OTHER INFORMATION: any nucleic acid or absent (e.g., t, u, h, or absent)
<220> FEATURE:
<221> NAME/KEY: misc_feature
<222> LOCATION: (14)..(14)
<223> OTHER INFORMATION: any nucleic acid or absent (e.g., a or absent)
<220> FEATURE:
<221> NAME/KEY: misc_feature
<222> LOCATION: (18)..(18)
<223> OTHER INFORMATION: any nucleic acid or absent (e.g., c or absent)
<220> FEATURE:
<221> NAME/KEY: misc_feature
<222> LOCATION: (19)..(20)
<223> OTHER INFORMATION: any nucleic acid or absent (e.g., independently, a or absent)
<220> FEATURE:
<221> NAME/KEY: misc_feature
<222> LOCATION: (21)..(21)
<223> OTHER INFORMATION: any nucleic acid or absent (e.g., t, u, or absent)
<220> FEATURE:
<221> NAME/KEY: misc_feature
<222> LOCATION: (22)..(22)
<223> OTHER INFORMATION: any nucleic acid or absent (e.g., a or absent)
<220> FEATURE:
<221> NAME/KEY: misc_feature
<222> LOCATION: (23)..(23)
<223> OTHER INFORMATION: any nucleic acid or absent (e.g., c or absent)
<220> FEATURE:
<221> NAME/KEY: misc_feature
<222> LOCATION: (24)..(24)
<223> OTHER INFORMATION: any nucleic acid or absent (e.g., a or absent)
<220> FEATURE:
<221> NAME/KEY: misc_feature

```
<222> LOCATION: (41)..(41)
<223> OTHER INFORMATION: any nucleic acid or absent (e.g., c or absent)
<220> FEATURE:
<221> NAME/KEY: misc_feature
<222> LOCATION: (42)..(42)
<223> OTHER INFORMATION: any nucleic acid or absent (e.g., g or absent)
<220> FEATURE:
<221> NAME/KEY: misc_feature
<222> LOCATION: (56)..(56)
<223> OTHER INFORMATION: any nucleic acid or absent (e.g., g or absent)

<400> SEQUENCE: 6
naannnnttt tnnnaaannn nnnntttgac aattaatcat nncggctcgt ataatnatcg    60
gctgaaatta atgagg                                                   76

<210> SEQ ID NO 7
<211> LENGTH: 76
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: any nucleic acid or absent (e.g., g or absent)
<220> FEATURE:
<221> NAME/KEY: misc_feature
<222> LOCATION: (1)..(76)
<223> OTHER INFORMATION: t, if present, may be u
<220> FEATURE:
<221> NAME/KEY: misc_feature
<222> LOCATION: (4)..(4)
<223> OTHER INFORMATION: any nucleic acid or absent (e.g., t, u, w, or
      absent)
<220> FEATURE:
<221> NAME/KEY: misc_feature
<222> LOCATION: (18)..(18)
<223> OTHER INFORMATION: any nucleic acid or absent (e.g., c or absent)
<220> FEATURE:
<221> NAME/KEY: misc_feature
<222> LOCATION: (19)..(20)
<223> OTHER INFORMATION: any nucleic acid or absent (e.g.,
      independently, a or absent)
<220> FEATURE:
<221> NAME/KEY: misc_feature
<222> LOCATION: (21)..(21)
<223> OTHER INFORMATION: any nucleic acid or absent (e.g., t, u, or
      absent)
<220> FEATURE:
<221> NAME/KEY: misc_feature
<222> LOCATION: (22)..(22)
<223> OTHER INFORMATION: any nucleic acid or absent (e.g., a or absent)
<220> FEATURE:
<221> NAME/KEY: misc_feature
<222> LOCATION: (23)..(23)
<223> OTHER INFORMATION: any nucleic acid or absent (e.g., c or absent)
<220> FEATURE:
<221> NAME/KEY: misc_feature
<222> LOCATION: (24)..(24)
<223> OTHER INFORMATION: any nucleic acid or absent (e.g., a or absent)
<220> FEATURE:
<221> NAME/KEY: misc_feature
<222> LOCATION: (41)..(41)
<223> OTHER INFORMATION: any nucleic acid or absent (e.g., c or absent)
<220> FEATURE:
<221> NAME/KEY: misc_feature
<222> LOCATION: (42)..(42)
<223> OTHER INFORMATION: any nucleic acid or absent (e.g., g or absent)
<220> FEATURE:
<221> NAME/KEY: misc_feature
<222> LOCATION: (56)..(56)
<223> OTHER INFORMATION: any nucleic acid or absent (e.g., g or absent)

<400> SEQUENCE: 7
naanhdwttt thhaaaannn nnnntttgac aattaatcat nncggctcgt ataatnatcg    60
```
gctgaaatta atgagg                                                76

<210> SEQ ID NO 8
<211> LENGTH: 76
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: any nucleic acid or absent (e.g., g or absent)
<220> FEATURE:
<221> NAME/KEY: misc_feature
<222> LOCATION: (1)..(76)
<223> OTHER INFORMATION: t, if present, may be u
<220> FEATURE:
<221> NAME/KEY: misc_feature
<222> LOCATION: (12)..(12)
<223> OTHER INFORMATION: any nucleic acid or absent (e.g., c, h, or
      absent)
<220> FEATURE:
<221> NAME/KEY: misc_feature
<222> LOCATION: (13)..(13)
<223> OTHER INFORMATION: any nucleic acid or absent (e.g., t, u, h, or
      absent)
<220> FEATURE:
<221> NAME/KEY: misc_feature
<222> LOCATION: (18)..(18)
<223> OTHER INFORMATION: any nucleic acid or absent (e.g., c or absent)
<220> FEATURE:
<221> NAME/KEY: misc_feature
<222> LOCATION: (19)..(20)
<223> OTHER INFORMATION: any nucleic acid or absent (e.g.,
      independently, a or absent)
<220> FEATURE:
<221> NAME/KEY: misc_feature
<222> LOCATION: (21)..(21)
<223> OTHER INFORMATION: any nucleic acid or absent (e.g., t, u, or
      absent)
<220> FEATURE:
<221> NAME/KEY: misc_feature
<222> LOCATION: (22)..(22)
<223> OTHER INFORMATION: any nucleic acid or absent (e.g., a or absent)
<220> FEATURE:
<221> NAME/KEY: misc_feature
<222> LOCATION: (23)..(23)
<223> OTHER INFORMATION: any nucleic acid or absent (e.g., c or absent)
<220> FEATURE:
<221> NAME/KEY: misc_feature
<222> LOCATION: (24)..(24)
<223> OTHER INFORMATION: any nucleic acid or absent (e.g., a or absent)
<220> FEATURE:
<221> NAME/KEY: misc_feature
<222> LOCATION: (41)..(41)
<223> OTHER INFORMATION: any nucleic acid or absent (e.g., c or absent)
<220> FEATURE:
<221> NAME/KEY: misc_feature
<222> LOCATION: (42)..(42)
<223> OTHER INFORMATION: any nucleic acid or absent (e.g., g or absent)
<220> FEATURE:
<221> NAME/KEY: misc_feature
<222> LOCATION: (56)..(56)
<223> OTHER INFORMATION: any nucleic acid or absent (e.g., g or absent)

<400> SEQUENCE: 8
naawwtwttt tnnaaaannn nnnntttgac aattaatcat nncggctcgt ataatnatcg    60
gctgaaatta atgagg                                                76

<210> SEQ ID NO 9
<211> LENGTH: 76
<212> TYPE: DNA
<213> ORGANISM: Artificial Sequence
<220> FEATURE:

```
<223> OTHER INFORMATION: Synthetic construct
<220> FEATURE:
<221> NAME/KEY: misc_feature
<222> LOCATION: (1)..(1)
<223> OTHER INFORMATION: any nucleic acid or absent (e.g., g or absent)
<220> FEATURE:
<221> NAME/KEY: misc_feature
<222> LOCATION: (1)..(76)
<223> OTHER INFORMATION: t, if present, may be u
<220> FEATURE:
<221> NAME/KEY: misc_feature
<222> LOCATION: (12)..(12)
<223> OTHER INFORMATION: any nucleic acid or absent (e.g., c, h, or
      absent)
<220> FEATURE:
<221> NAME/KEY: misc_feature
<222> LOCATION: (13)..(13)
<223> OTHER INFORMATION: any nucleic acid or absent (e.g., t, u, h, or
      absent)
<220> FEATURE:
<221> NAME/KEY: misc_feature
<222> LOCATION: (18)..(18)
<223> OTHER INFORMATION: any nucleic acid or absent (e.g., c or absent)
<220> FEATURE:
<221> NAME/KEY: misc_feature
<222> LOCATION: (19)..(20)
<223> OTHER INFORMATION: any nucleic acid or absent (e.g.,
      independently, a or absent)
<220> FEATURE:
<221> NAME/KEY: misc_feature
<222> LOCATION: (21)..(21)
<223> OTHER INFORMATION: any nucleic acid or absent (e.g., t, u, or
      absent)
<220> FEATURE:
<221> NAME/KEY: misc_feature
<222> LOCATION: (22)..(22)
<223> OTHER INFORMATION: any nucleic acid or absent (e.g., a or absent)
<220> FEATURE:
<221> NAME/KEY: misc_feature
<222> LOCATION: (23)..(23)
<223> OTHER INFORMATION: any nucleic acid or absent (e.g., c or absent)
<220> FEATURE:
<221> NAME/KEY: misc_feature
<222> LOCATION: (24)..(24)
<223> OTHER INFORMATION: any nucleic acid or absent (e.g., a or absent)
<220> FEATURE:
<221> NAME/KEY: misc_feature
<222> LOCATION: (41)..(41)
<223> OTHER INFORMATION: any nucleic acid or absent (e.g., c or absent)
<220> FEATURE:
<221> NAME/KEY: misc_feature
<222> LOCATION: (42)..(42)
<223> OTHER INFORMATION: any nucleic acid or absent (e.g., g or absent)
<220> FEATURE:
<221> NAME/KEY: misc_feature
<222> LOCATION: (56)..(56)
<223> OTHER INFORMATION: any nucleic acid or absent (e.g., g or absent)

<400> SEQUENCE: 9
naawwtwttt tnnaaaannn nnnntttrmy aattaatcat nncggctcgt aywatnatcg    60
gctgaaatta atgagg                                                   76

<210> SEQ ID NO 10
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(24)
<223> OTHER INFORMATION: t, if present, may be u

<400> SEQUENCE: 10
gaatcatttt tctaaaacaa taca                                          24
```

```
<210> SEQ ID NO 11
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: any nucleic acid or absent (e.g., g or absent)
<220> FEATURE:
<221> NAME/KEY: misc_feature
<222> LOCATION: (1)..(24)
<223> OTHER INFORMATION: t, if present, may be u
<220> FEATURE:
<221> NAME/KEY: misc_feature
<222> LOCATION: (4)..(4)
<223> OTHER INFORMATION: any nucleic acid or absent (e.g., t, u, w, or
      absent)
<220> FEATURE:
<221> NAME/KEY: misc_feature
<222> LOCATION: (5)..(5)
<223> OTHER INFORMATION: any nucleic acid or absent (e.g., c, h, w, or
      absent)
<220> FEATURE:
<221> NAME/KEY: misc_feature
<222> LOCATION: (6)..(6)
<223> OTHER INFORMATION: any nucleic acid or absent (e.g., a, t, u, d,
      or absent)
<220> FEATURE:
<221> NAME/KEY: misc_feature
<222> LOCATION: (7)..(7)
<223> OTHER INFORMATION: any nucleic acid or absent (e.g., t, u, w, or
      absent)
<220> FEATURE:
<221> NAME/KEY: misc_feature
<222> LOCATION: (12)..(12)
<223> OTHER INFORMATION: any nucleic acid or absent (e.g., c, h, or
      absent)
<220> FEATURE:
<221> NAME/KEY: misc_feature
<222> LOCATION: (13)..(13)
<223> OTHER INFORMATION: any nucleic acid or absent (e.g., t, u, h, or
      absent)
<220> FEATURE:
<221> NAME/KEY: misc_feature
<222> LOCATION: (14)..(14)
<223> OTHER INFORMATION: any nucleic acid or absent (e.g., a or absent)
<220> FEATURE:
<221> NAME/KEY: misc_feature
<222> LOCATION: (18)..(18)
<223> OTHER INFORMATION: any nucleic acid or absent (e.g., c or absent)
<220> FEATURE:
<221> NAME/KEY: misc_feature
<222> LOCATION: (19)..(20)
<223> OTHER INFORMATION: any nucleic acid or absent (e.g.,
      independently, a or absent)
<220> FEATURE:
<221> NAME/KEY: misc_feature
<222> LOCATION: (21)..(21)
<223> OTHER INFORMATION: any nucleic acid or absent (e.g., t, u, or
      absent)
<220> FEATURE:
<221> NAME/KEY: misc_feature
<222> LOCATION: (22)..(22)
<223> OTHER INFORMATION: any nucleic acid or absent (e.g., a or absent)
<220> FEATURE:
<221> NAME/KEY: misc_feature
<222> LOCATION: (23)..(23)
<223> OTHER INFORMATION: any nucleic acid or absent (e.g., c or absent)
<220> FEATURE:
<221> NAME/KEY: misc_feature
<222> LOCATION: (24)..(24)
<223> OTHER INFORMATION: any nucleic acid or absent (e.g., a or absent)

<400> SEQUENCE: 11
```

```
naannnnttt tnnnaaannn nnnn                                              24
```

<210> SEQ ID NO 12
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: any nucleic acid or absent (e.g., g or absent)
<220> FEATURE:
<221> NAME/KEY: misc_feature
<222> LOCATION: (1)..(24)
<223> OTHER INFORMATION: t, if present, may be u
<220> FEATURE:
<221> NAME/KEY: misc_feature
<222> LOCATION: (4)..(4)
<223> OTHER INFORMATION: any nucleic acid or absent (e.g., t, u, w, or absent)
<220> FEATURE:
<221> NAME/KEY: misc_feature
<222> LOCATION: (7)..(7)
<223> OTHER INFORMATION: any nucleic acid or absent (e.g., t, u, w, or absent)
<220> FEATURE:
<221> NAME/KEY: misc_feature
<222> LOCATION: (18)..(18)
<223> OTHER INFORMATION: any nucleic acid or absent (e.g., c or absent)
<220> FEATURE:
<221> NAME/KEY: misc_feature
<222> LOCATION: (19)..(20)
<223> OTHER INFORMATION: any nucleic acid or absent (e.g., independently, a or absent)
<220> FEATURE:
<221> NAME/KEY: misc_feature
<222> LOCATION: (21)..(21)
<223> OTHER INFORMATION: any nucleic acid or absent (e.g., t, u, or absent)
<220> FEATURE:
<221> NAME/KEY: misc_feature
<222> LOCATION: (22)..(22)
<223> OTHER INFORMATION: any nucleic acid or absent (e.g., a or absent)
<220> FEATURE:
<221> NAME/KEY: misc_feature
<222> LOCATION: (23)..(23)
<223> OTHER INFORMATION: any nucleic acid or absent (e.g., c or absent)
<220> FEATURE:
<221> NAME/KEY: misc_feature
<222> LOCATION: (24)..(24)
<223> OTHER INFORMATION: any nucleic acid or absent (e.g., a or absent)

<400> SEQUENCE: 12

```
naanhdnttt thhaaaannn nnnn                                              24
```

<210> SEQ ID NO 13
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: any nucleic acid or absent (e.g., g or absent)
<220> FEATURE:
<221> NAME/KEY: misc_feature
<222> LOCATION: (1)..(24)
<223> OTHER INFORMATION: t, if present, may be u
<220> FEATURE:
<221> NAME/KEY: misc_feature
<222> LOCATION: (4)..(4)
<223> OTHER INFORMATION: any nucleic acid or absent (e.g., t, u, w, or absent)
<220> FEATURE:

```
<221> NAME/KEY: misc_feature
<222> LOCATION: (7)..(7)
<223> OTHER INFORMATION: any nucleic acid or absent (e.g., t, u, w, or
      absent)
<220> FEATURE:
<221> NAME/KEY: misc_feature
<222> LOCATION: (18)..(18)
<223> OTHER INFORMATION: any nucleic acid or absent (e.g., c or absent)
<220> FEATURE:
<221> NAME/KEY: misc_feature
<222> LOCATION: (19)..(20)
<223> OTHER INFORMATION: any nucleic acid or absent (e.g.,
      independently, a or absent)
<220> FEATURE:
<221> NAME/KEY: misc_feature
<222> LOCATION: (21)..(21)
<223> OTHER INFORMATION: any nucleic acid or absent (e.g., t, u, or
      absent)
<220> FEATURE:
<221> NAME/KEY: misc_feature
<222> LOCATION: (22)..(22)
<223> OTHER INFORMATION: any nucleic acid or absent (e.g., a or absent)
<220> FEATURE:
<221> NAME/KEY: misc_feature
<222> LOCATION: (23)..(23)
<223> OTHER INFORMATION: any nucleic acid or absent (e.g., c or absent)
<220> FEATURE:
<221> NAME/KEY: misc_feature
<222> LOCATION: (24)..(24)
<223> OTHER INFORMATION: any nucleic acid or absent (e.g., a or absent)

<400> SEQUENCE: 13
naanhdnttt thhaaaannn nnnn                                            24

<210> SEQ ID NO 14
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: any nucleic acid or absent (e.g., g or absent)
<220> FEATURE:
<221> NAME/KEY: misc_feature
<222> LOCATION: (1)..(24)
<223> OTHER INFORMATION: t, if present, may be u
<220> FEATURE:
<221> NAME/KEY: misc_feature
<222> LOCATION: (4)..(4)
<223> OTHER INFORMATION: any nucleic acid or absent (e.g., t, u, w, or
      absent)
<220> FEATURE:
<221> NAME/KEY: misc_feature
<222> LOCATION: (18)..(18)
<223> OTHER INFORMATION: any nucleic acid or absent (e.g., c or absent)
<220> FEATURE:
<221> NAME/KEY: misc_feature
<222> LOCATION: (19)..(20)
<223> OTHER INFORMATION: any nucleic acid or absent (e.g.,
      independently, a or absent)
<220> FEATURE:
<221> NAME/KEY: misc_feature
<222> LOCATION: (21)..(21)
<223> OTHER INFORMATION: any nucleic acid or absent (e.g., t, u, or
      absent)
<220> FEATURE:
<221> NAME/KEY: misc_feature
<222> LOCATION: (22)..(22)
<223> OTHER INFORMATION: any nucleic acid or absent (e.g., a or absent)
<220> FEATURE:
<221> NAME/KEY: misc_feature
<222> LOCATION: (23)..(23)
<223> OTHER INFORMATION: any nucleic acid or absent (e.g., c or absent)
<220> FEATURE:
<221> NAME/KEY: misc_feature
```

```
<222> LOCATION: (24)..(24)
<223> OTHER INFORMATION: any nucleic acid or absent (e.g., a or absent)

<400> SEQUENCE: 14
naanhdwttt thhaaaannn nnnn                                             24

<210> SEQ ID NO 15
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: any nucleic acid or absent (e.g., g or absent)
<220> FEATURE:
<221> NAME/KEY: misc_feature
<222> LOCATION: (1)..(24)
<223> OTHER INFORMATION: t, if present, may be u
<220> FEATURE:
<221> NAME/KEY: misc_feature
<222> LOCATION: (12)..(12)
<223> OTHER INFORMATION: any nucleic acid or absent (e.g., c, h, or
      absent)
<220> FEATURE:
<221> NAME/KEY: misc_feature
<222> LOCATION: (13)..(13)
<223> OTHER INFORMATION: any nucleic acid or absent (e.g., t, u, h, or
      absent)
<220> FEATURE:
<221> NAME/KEY: misc_feature
<222> LOCATION: (18)..(18)
<223> OTHER INFORMATION: any nucleic acid or absent (e.g., c or absent)
<220> FEATURE:
<221> NAME/KEY: misc_feature
<222> LOCATION: (19)..(20)
<223> OTHER INFORMATION: any nucleic acid or absent (e.g.,
      independently, a or absent)
<220> FEATURE:
<221> NAME/KEY: misc_feature
<222> LOCATION: (21)..(21)
<223> OTHER INFORMATION: any nucleic acid or absent (e.g., t, u, or
      absent)
<220> FEATURE:
<221> NAME/KEY: misc_feature
<222> LOCATION: (22)..(22)
<223> OTHER INFORMATION: any nucleic acid or absent (e.g., a or absent)
<220> FEATURE:
<221> NAME/KEY: misc_feature
<222> LOCATION: (23)..(23)
<223> OTHER INFORMATION: any nucleic acid or absent (e.g., c or absent)
<220> FEATURE:
<221> NAME/KEY: misc_feature
<222> LOCATION: (24)..(24)
<223> OTHER INFORMATION: any nucleic acid or absent (e.g., a or absent)

<400> SEQUENCE: 15
naawwtwttt tnnaaaannn nnnn                                             24

<210> SEQ ID NO 16
<211> LENGTH: 16
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(16)
<223> OTHER INFORMATION: t, if present, may be u
<220> FEATURE:
<221> NAME/KEY: misc_feature
<222> LOCATION: (3)..(3)
<223> OTHER INFORMATION: any nucleic acid or absent (e.g., t, u, w, or
      absent)
```

```
<220> FEATURE:
<221> NAME/KEY: misc_feature
<222> LOCATION: (4)..(4)
<223> OTHER INFORMATION: any nucleic acid or absent (e.g., c, h, w, or
      absent)
<220> FEATURE:
<221> NAME/KEY: misc_feature
<222> LOCATION: (5)..(5)
<223> OTHER INFORMATION: any nucleic acid or absent (e.g., a, t, u, d,
      or absent)
<220> FEATURE:
<221> NAME/KEY: misc_feature
<222> LOCATION: (6)..(6)
<223> OTHER INFORMATION: any nucleic acid or absent (e.g., t, u, w, or
      absent)
<220> FEATURE:
<221> NAME/KEY: misc_feature
<222> LOCATION: (11)..(11)
<223> OTHER INFORMATION: any nucleic acid or absent (e.g., c, h, or
      absent)
<220> FEATURE:
<221> NAME/KEY: misc_feature
<222> LOCATION: (12)..(12)
<223> OTHER INFORMATION: any nucleic acid or absent (e.g., t, u, h, or
      absent)
<220> FEATURE:
<221> NAME/KEY: misc_feature
<222> LOCATION: (13)..(13)
<223> OTHER INFORMATION: any nucleic acid or absent (e.g., a or absent)

<400> SEQUENCE: 16
aannnntttt nnnaaa                                                       16

<210> SEQ ID NO 17
<211> LENGTH: 16
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(16)
<223> OTHER INFORMATION: t, if present, may be u
<220> FEATURE:
<221> NAME/KEY: misc_feature
<222> LOCATION: (3)..(3)
<223> OTHER INFORMATION: any nucleic acid or absent (e.g., t, u, w, or
      absent)
<220> FEATURE:
<221> NAME/KEY: misc_feature
<222> LOCATION: (6)..(6)
<223> OTHER INFORMATION: any nucleic acid or absent (e.g., t, u, w, or
      absent)

<400> SEQUENCE: 17
aanhdntttt hhaaaa                                                       16

<210> SEQ ID NO 18
<211> LENGTH: 16
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(16)
<223> OTHER INFORMATION: t, if present, may be u
<220> FEATURE:
<221> NAME/KEY: misc_feature
<222> LOCATION: (3)..(3)
<223> OTHER INFORMATION: any nucleic acid or absent (e.g., t, u, w, or
      absent)

<400> SEQUENCE: 18
```
aanhdwtttt hhaaaa                                                          16

<210> SEQ ID NO 19
<211> LENGTH: 16
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(16)
<223> OTHER INFORMATION: t, if present, may be u
<220> FEATURE:
<221> NAME/KEY: misc_feature
<222> LOCATION: (11)..(11)
<223> OTHER INFORMATION: any nucleic acid or absent (e.g., c, h, or
      absent)
<220> FEATURE:
<221> NAME/KEY: misc_feature
<222> LOCATION: (12)..(12)
<223> OTHER INFORMATION: any nucleic acid or absent (e.g., t, u, h, or
      absent)

<400> SEQUENCE: 19
aawwtwtttt nnaaaa                                                          16

<210> SEQ ID NO 20
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(3)
<223> OTHER INFORMATION: any nucleic acid or absent (e.g.,
      independently, g or absent)
<220> FEATURE:
<221> NAME/KEY: misc_feature
<222> LOCATION: (1)..(22)
<223> OTHER INFORMATION: t, if present, may be u
<220> FEATURE:
<221> NAME/KEY: misc_feature
<222> LOCATION: (6)..(6)
<223> OTHER INFORMATION: any nucleic acid or absent (e.g., t, u, w, or
      absent)
<220> FEATURE:
<221> NAME/KEY: misc_feature
<222> LOCATION: (7)..(7)
<223> OTHER INFORMATION: any nucleic acid or absent (e.g., c, h, w, or
      absent)
<220> FEATURE:
<221> NAME/KEY: misc_feature
<222> LOCATION: (8)..(8)
<223> OTHER INFORMATION: any nucleic acid or absent (e.g., a, t, u, d,
      or absent)
<220> FEATURE:
<221> NAME/KEY: misc_feature
<222> LOCATION: (9)..(9)
<223> OTHER INFORMATION: any nucleic acid or absent (e.g., t, u, w, or
      absent)
<220> FEATURE:
<221> NAME/KEY: misc_feature
<222> LOCATION: (14)..(14)
<223> OTHER INFORMATION: any nucleic acid or absent (e.g., c, h, or
      absent)
<220> FEATURE:
<221> NAME/KEY: misc_feature
<222> LOCATION: (15)..(15)
<223> OTHER INFORMATION: any nucleic acid or absent (e.g., t, u, h, or
      absent)
<220> FEATURE:
<221> NAME/KEY: misc_feature
<222> LOCATION: (16)..(16)
<223> OTHER INFORMATION: any nucleic acid or absent (e.g., a or absent)
<220> FEATURE:

```
<221> NAME/KEY: misc_feature
<222> LOCATION: (20)..(20)
<223> OTHER INFORMATION: any nucleic acid or absent (e.g., c or absent)
<220> FEATURE:
<221> NAME/KEY: misc_feature
<222> LOCATION: (21)..(22)
<223> OTHER INFORMATION: any nucleic acid or absent (e.g.,
      independently, a or absent)

<400> SEQUENCE: 20
nnnaannnnt tttnnnaaan nn                                              22

<210> SEQ ID NO 21
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: any nucleic acid or absent (e.g.,
      independently, g or absent)
<220> FEATURE:
<221> NAME/KEY: misc_feature
<222> LOCATION: (1)..(22)
<223> OTHER INFORMATION: t, if present, may be u
<220> FEATURE:
<221> NAME/KEY: misc_feature
<222> LOCATION: (14)..(14)
<223> OTHER INFORMATION: any nucleic acid or absent (e.g., c, h, or
      absent)
<220> FEATURE:
<221> NAME/KEY: misc_feature
<222> LOCATION: (15)..(15)
<223> OTHER INFORMATION: any nucleic acid or absent (e.g., t, u, h, or
      absent)
<220> FEATURE:
<221> NAME/KEY: misc_feature
<222> LOCATION: (20)..(20)
<223> OTHER INFORMATION: any nucleic acid or absent (e.g., c or absent)
<220> FEATURE:
<221> NAME/KEY: misc_feature
<222> LOCATION: (21)..(22)
<223> OTHER INFORMATION: any nucleic acid or absent (e.g.,
      independently, a or absent)

<400> SEQUENCE: 21
nnaaawwtwt tttnnaaaan nn                                              22

<210> SEQ ID NO 22
<211> LENGTH: 6
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(6)
<223> OTHER INFORMATION: t, if present, may be u

<400> SEQUENCE: 22 tttact                                                                 6

<210> SEQ ID NO 23
<211> LENGTH: 6
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(6)
```

<223> OTHER INFORMATION: t, if present, may be u

<400> SEQUENCE: 23 tttgac                                                                        6

<210> SEQ ID NO 24
<211> LENGTH: 6
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(6)
<223> OTHER INFORMATION: t, if present, may be u

<400> SEQUENCE: 24 tttrmy                                                                        6

<210> SEQ ID NO 25
<211> LENGTH: 6
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(6)
<223> OTHER INFORMATION: t, if present, may be u
<220> FEATURE:
<221> NAME/KEY: misc_feature
<222> LOCATION: (4)..(4)
<223> OTHER INFORMATION: any nucleic acid or absent (e.g., a, g, r, or
      absent)
<220> FEATURE:
<221> NAME/KEY: misc_feature
<222> LOCATION: (5)..(5)
<223> OTHER INFORMATION: any nucleic acid or absent (e.g., c, a, m, or
      absent)
<220> FEATURE:
<221> NAME/KEY: misc_feature
<222> LOCATION: (6)..(6)
<223> OTHER INFORMATION: any nucleic acid or absent (e.g., t, u, c, y,
      or absent)

<400> SEQUENCE: 25 tttnnn                                                                        6

<210> SEQ ID NO 26
<211> LENGTH: 17
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(17)
<223> OTHER INFORMATION: t, if present, may be u

<400> SEQUENCE: 26
aattaatcat cggctcg                                                           17

<210> SEQ ID NO 27
<211> LENGTH: 17
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(17)

-continued

<223> OTHER INFORMATION: t, if present, may be u

<400> SEQUENCE: 27
aattaatcat cgactag                                                      17

<210> SEQ ID NO 28
<211> LENGTH: 18
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(18)
<223> OTHER INFORMATION: t, if present, may be u

<400> SEQUENCE: 28
aattaatcat cgaactag                                                     18

<210> SEQ ID NO 29
<211> LENGTH: 18
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(18)
<223> OTHER INFORMATION: t, if present, may be u

<400> SEQUENCE: 29
aattaatcat ccggctcg                                                     18

<210> SEQ ID NO 30
<211> LENGTH: 19
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(19)
<223> OTHER INFORMATION: t, if present, may be u

<400> SEQUENCE: 30
aattaatcat cgcggctcg                                                    19

<210> SEQ ID NO 31
<211> LENGTH: 19
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(19)
<223> OTHER INFORMATION: t, if present, may be u
<220> FEATURE:
<221> NAME/KEY: misc_feature
<222> LOCATION: (11)..(11)
<223> OTHER INFORMATION: any nucleic acid or absent (e.g., c or absent)
<220> FEATURE:
<221> NAME/KEY: misc_feature
<222> LOCATION: (12)..(12)
<223> OTHER INFORMATION: any nucleic acid or absent (e.g., c, g, or
      absent)

<400> SEQUENCE: 31
aattaatcat nncgrctmg                                                    19

<210> SEQ ID NO 32
<211> LENGTH: 19
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(19)
<223> OTHER INFORMATION: t, if present, may be u
<220> FEATURE:
<221> NAME/KEY: misc_feature
<222> LOCATION: (11)..(11)
<223> OTHER INFORMATION: any nucleic acid or absent (e.g., c or absent)
<220> FEATURE:
<221> NAME/KEY: misc_feature
<222> LOCATION: (12)..(12)
<223> OTHER INFORMATION: any nucleic acid or absent (e.g., g, c, or
      absent)

<400> SEQUENCE: 32
aattaatcat nncggctcg                                              19

<210> SEQ ID NO 33
<211> LENGTH: 19
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(19)
<223> OTHER INFORMATION: t, if present, may be u
<220> FEATURE:
<221> NAME/KEY: misc_feature
<222> LOCATION: (11)..(11)
<223> OTHER INFORMATION: any nucleic acid or absent (e.g., c or absent)
<220> FEATURE:
<221> NAME/KEY: misc_feature
<222> LOCATION: (12)..(12)
<223> OTHER INFORMATION: any nucleic acid or absent (e.g., g, c, or
      absent)
<220> FEATURE:
<221> NAME/KEY: misc_feature
<222> LOCATION: (15)..(15)
<223> OTHER INFORMATION: any nucleic acid or absent (e.g., t, u, c, g,
      r, or absent)
<220> FEATURE:
<221> NAME/KEY: misc_feature
<222> LOCATION: (18)..(18)
<223> OTHER INFORMATION: any nucleic acid or absent (e.g., g, c, m, or
      absent)

<400> SEQUENCE: 33
aattaatcat nncgnctng                                              19

<210> SEQ ID NO 34
<211> LENGTH: 6
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(6)
<223> OTHER INFORMATION: t, if present, may be u

<400> SEQUENCE: 34 tactat                                                            6

<210> SEQ ID NO 35
<211> LENGTH: 6

```
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(6)
<223> OTHER INFORMATION: t, if present, may be u

<400> SEQUENCE: 35 tataat                                                                      6

<210> SEQ ID NO 36
<211> LENGTH: 6
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(6)
<223> OTHER INFORMATION: t, if present, may be u

<400> SEQUENCE: 36 taywat                                                                      6

<210> SEQ ID NO 37
<211> LENGTH: 6
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(6)
<223> OTHER INFORMATION: t, if present, may be u
<220> FEATURE:
<221> NAME/KEY: misc_feature
<222> LOCATION: (3)..(3)
<223> OTHER INFORMATION: any nucleic acid or absent (e.g., c, t, u, y,
      or absent)
<220> FEATURE:
<221> NAME/KEY: misc_feature
<222> LOCATION: (4)..(4)
<223> OTHER INFORMATION: any nucleic acid or absent (e.g., t, u, a, w,
      or absent)

<400> SEQUENCE: 37 tannat                                                                      6

<210> SEQ ID NO 38
<211> LENGTH: 33
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(33)
<223> OTHER INFORMATION: t, if present, may be u

<400> SEQUENCE: 38
gatcggctga aattaatgag gtcatacccca aat                                      33

<210> SEQ ID NO 39
<211> LENGTH: 21
<212> TYPE: DNA
<213> ORGANISM: Artificial Sequence
<220> FEATURE:
<223> OTHER INFORMATION: Synthetic construct
<220> FEATURE:
```

```
<221> NAME/KEY: misc_feature
<222> LOCATION: (1)..(1)
<223> OTHER INFORMATION: any nucleic acid or absent (e.g., g or absent)
<220> FEATURE:
<221> NAME/KEY: misc_feature
<222> LOCATION: (1)..(21)
<223> OTHER INFORMATION: t, if present, may be u

<400> SEQUENCE: 39
natcggctga aattaatgag g                                              21

<210> SEQ ID NO 40
<211> LENGTH: 17
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: any nucleic acid or absent (e.g., g or absent)
<220> FEATURE:
<221> NAME/KEY: misc_feature
<222> LOCATION: (1)..(17)
<223> OTHER INFORMATION: t, if present, may be u

<400> SEQUENCE: 40
nttgttggca taattaa                                                   17

<210> SEQ ID NO 41
<211> LENGTH: 17
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: any nucleic acid or absent (e.g., g or absent)
<220> FEATURE:
<221> NAME/KEY: misc_feature
<222> LOCATION: (1)..(17)
<223> OTHER INFORMATION: t, if present, may be u

<400> SEQUENCE: 41
ncagcaaatc tgtatat                                                   17

<210> SEQ ID NO 42
<211> LENGTH: 13
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(13)
<223> OTHER INFORMATION: t, if present, may be u

<400> SEQUENCE: 42
gtgtggaatt gtg                                                       13

<210> SEQ ID NO 43
<211> LENGTH: 128
<212> TYPE: DNA
<213> ORGANISM: Artificial Sequence
<220> FEATURE:
<223> OTHER INFORMATION: Synthetic construct

<400> SEQUENCE: 43
gcgcggatcc gaatcatttt tctaaaacaa tacatttact ttatttgtca ctgtcgttac    60
```

```
tatatcggct gaaattaatg aggtcatacc caaataagga ggatattatg gtttccaagg    120
gcgaggag                                                             128

<210> SEQ ID NO 44
<211> LENGTH: 131
<212> TYPE: DNA
<213> ORGANISM: Artificial Sequence
<220> FEATURE:
<223> OTHER INFORMATION: Synthetic construct

<400> SEQUENCE: 44
gcgcggatcc gaatcatttt tctaaaacaa tacatttgac aattaatcat cggctcgtat    60
aatgatcggc tgaaattaat gaggtcatac ccaaataagg aggggaattc atggtttcca    120
agggcgagga g                                                         131

<210> SEQ ID NO 45
<211> LENGTH: 132
<212> TYPE: DNA
<213> ORGANISM: Artificial Sequence
<220> FEATURE:
<223> OTHER INFORMATION: Synthetic construct

<400> SEQUENCE: 45
gcgcggatcc gaatcatttt tctaaaacaa tacatttgac aattaatcat ccggctcgta    60
taatgatcgg ctgaaattaa tgaggtcata cccaaataag gaggggaatt catggtttcc    120
aagggcgagg ag                                                        132

<210> SEQ ID NO 46
<211> LENGTH: 133
<212> TYPE: DNA
<213> ORGANISM: Artificial Sequence
<220> FEATURE:
<223> OTHER INFORMATION: Synthetic construct

<400> SEQUENCE: 46
gcgcggatcc gaatcatttt tctaaaacaa tacatttgac aattaatcat cgcggctcgt    60
ataatgatcg gctgaaatta atgaggtcat acccaaataa ggaggggaat tcatggtttc    120
caagggcgag gag                                                       133

<210> SEQ ID NO 47
<211> LENGTH: 28
<212> TYPE: DNA
<213> ORGANISM: Artificial Sequence
<220> FEATURE:
<223> OTHER INFORMATION: Synthetic construct

<400> SEQUENCE: 47
cggctgaaat taatgaggtc atacccaa                                       28

<210> SEQ ID NO 48
<211> LENGTH: 44
<212> TYPE: DNA
<213> ORGANISM: Artificial Sequence
<220> FEATURE:
<223> OTHER INFORMATION: Synthetic construct

<400> SEQUENCE: 48
gcgcaagctt gcggccgcag agtttgtaga aacgcaaaaa ggcc                     44

<210> SEQ ID NO 49
```

```
<211> LENGTH: 21
<212> TYPE: DNA
<213> ORGANISM: Artificial Sequence
<220> FEATURE:
<223> OTHER INFORMATION: Synthetic construct

<400> SEQUENCE: 49
aagcttgcgg ccgcagagtt t                                            21

<210> SEQ ID NO 50
<211> LENGTH: 25
<212> TYPE: DNA
<213> ORGANISM: Artificial Sequence
<220> FEATURE:
<223> OTHER INFORMATION: Synthetic construct

<400> SEQUENCE: 50
gtcgatcggt tcatcattca ccaaa                                        25

<210> SEQ ID NO 51
<211> LENGTH: 25
<212> TYPE: DNA
<213> ORGANISM: Artificial Sequence
<220> FEATURE:
<223> OTHER INFORMATION: Synthetic construct

<400> SEQUENCE: 51
tgtgagttag ctcactcatt aggca                                        25

<210> SEQ ID NO 52
<211> LENGTH: 85
<212> TYPE: DNA
<213> ORGANISM: Artificial Sequence
<220> FEATURE:
<223> OTHER INFORMATION: Synthetic construct

<400> SEQUENCE: 52
gaatcatttt tctaaaacaa tacatttact ttatttgtca ctgtcgttac tatatcggct   60
gaaattaatg aggtcatacc caaat                                        85

<210> SEQ ID NO 53
<211> LENGTH: 86
<212> TYPE: DNA
<213> ORGANISM: Artificial Sequence
<220> FEATURE:
<223> OTHER INFORMATION: Synthetic construct

<400> SEQUENCE: 53
gaatcatttt tctaaaacaa tacatttgac aattaatcat cggctcgtat aatgatcggc   60
tgaaattaat gaggtcatac ccaaat                                       86

<210> SEQ ID NO 54
<211> LENGTH: 87
<212> TYPE: DNA
<213> ORGANISM: Artificial Sequence
<220> FEATURE:
<223> OTHER INFORMATION: Synthetic construct

<400> SEQUENCE: 54
gaatcatttt tctaaaacaa tacatttgac aattaatcat ccggctcgta taatgatcgg   60
ctgaaattaa tgaggtcata cccaaat                                      87

<210> SEQ ID NO 55
<211> LENGTH: 88
```

-continued

```
<212> TYPE: DNA
<213> ORGANISM: Artificial Sequence
<220> FEATURE:
<223> OTHER INFORMATION: Synthetic construct

<400> SEQUENCE: 55
gaatcatttt tctaaaacaa tacatttgac aattaatcat cgcggctcgt ataatgatcg    60
gctgaaatta atgaggtcat acccaaat                                       88
```

PROMOTERS AND USES THEREOF

CROSS-REFERENCE TO RELATED APPLICATION

This application claims the benefit of U.S. Provisional Application No. 62/778,545, filed Dec. 12, 2018, which is hereby incorporated by reference in its entirety.

STATEMENT OF GOVERNMENT INTEREST

This invention was made with Government support under Contract No. DE-NA0003525 awarded by the United States Department of Energy/National Nuclear Security Administration. The Government has certain rights in the invention.

REFERENCE TO A SEQUENCE LISTING APPENDIX

A sequence listing appendix including an ASCII formatted file accompanies this application. The appendix includes a file named "SD14117_LST25.txt," created on Dec. 12, 2019 (size of 30.9 kilobytes), which is hereby incorporated by reference in its entirety.

FIELD OF THE INVENTION

The present invention relates to synthetic promoters, as well as expression cassettes, and recombinant scaffolds, and methods thereof. In particular embodiments, the synthetic promoter is inducible by one or more chemical compounds present during lignin depolymerization.

BACKGROUND OF THE INVENTION

Synthetic biology relies on many tools and constructs to engineer biological systems. One such construct includes a promoter that can control protein expression, including the extent or amount of protein being expressed. Furthermore, such promoters can be synthesized to be inducible in the presence of certain chemicals or proteins. In particular embodiments, synthetic promoters can be useful in constructing an efficient chassis for lignin break-down and valorization. Accordingly, there is a need for additional promoters for use in inducible systems and dynamic regulatory systems relying on biological breakdown of chemical agents.

SUMMARY OF THE INVENTION

The present invention describes an approach for providing enhanced synthetic promoters, which can be optionally induced in the presence of phenolic compounds. In one non-limiting instance, the breakdown of lignin sources can generate one or more phenolic compounds, and use of a phenolic-inducible promoter can provide a dynamic feedback system during lignin breakdown. In another non-limiting instance, the synthetic promoters herein can provide enhanced protein expression of a nucleic acid that is operably linked to the promoter. Such increased protein expression can provide efficient breakdown of complex compounds, such as polymers (e.g., lignin).

Accordingly, in a first aspect, the present invention features a synthetic promoter (e.g., a phenolic-inducible synthetic promoter) including a spacer region, wherein the spacer region includes: a first element (e.g., a −35 element) including a nucleic acid sequence having at least 80% sequence identity to any one of SEQ ID NOs:22-25 or a complement thereof; a second element (e.g., a variable element) including a nucleic acid sequence having at least 80% sequence identity to any one of SEQ ID NOs:26-33 or a complement thereof; and a third element (e.g., a −10 element) including a nucleic acid sequence having at least 80% sequence identity to any one of SEQ ID NOs:34-37 or a complement thereof.

In some embodiments, the synthetic promoter further includes an element (e.g., an UP element) upstream of the first element (e.g., the −35 element). In some embodiments, the element upstream of the first element includes a nucleic acid sequence having at least 80% sequence identity to any one of SEQ ID NOs: 10-21 or a fragment thereof or a complement of any of these.

In some embodiments, the synthetic promoter further includes an element (e.g., a DOWN element) downstream of the third element (e.g., the −10 element). In some embodiments, the element downstream of the third element a nucleic acid sequence having at least 80% sequence identity to any one of SEQ ID NOs:38-42 or a fragment thereof or a complement of any of these.

In some embodiments, the synthetic promoter includes a nucleic acid sequence having at least 80% sequence identity to any one of SEQ ID NOs: 1-9 or a fragment thereof or a complement of any of these.

In a second aspect, the present invention features an expression cassette including a synthetic promoter (e.g., a phenolic-inducible synthetic promoter, such as any described herein); and a gene located downstream of the synthetic promoter. In particular embodiments, the gene encodes a first protein that interacts with a first phenolic compound (e.g., any described herein).

In some embodiments, the first phenolic compound (e.g., any described herein) induces the synthetic promoter.

In a third aspect, the present invention features an expression cassette including: (i) a synthetic promoter (e.g., a phenolic-inducible synthetic promoter, wherein the synthetic promoter including a spacer region, wherein the spacer region includes: a first element including a nucleic acid sequence having at least 80% sequence identity to any one of SEQ ID NOs:22-25 or a complement thereof; a third element including a nucleic acid sequence having at least 80% sequence identity to any one of SEQ ID NOs:34-37 or a complement thereof; and a second element including a variable nucleic acid sequence disposed between the first and third elements); and (ii) a gene operably linked to the synthetic promoter (e.g., wherein the gene encodes a first protein that interacts with a first phenolic compound).

In some embodiments, the first phenolic compound (e.g., any described herein) induces the synthetic promoter.

In a fourth aspect, the present invention features an expression cassette including: (i) a first synthetic promoter (e.g., a first phenolic-inducible synthetic promoter, such as any described herein); (ii) a first gene operably linked to the first synthetic promoter (e.g., wherein the first gene encodes a first protein that interacts with a first phenolic compound); (iii) a second synthetic promoter (e.g., a second phenolic-inducible synthetic promoter, such as any described herein); and (iv) a second gene operably linked to the second synthetic promoter.

In some embodiments, the second gene encodes a second protein that interacts with a second phenolic compound, wherein the second phenolic compound is a product of a reaction between the first phenolic compound and the first protein. In other embodiments, the first and second phenolic compounds are different. In some embodiments, the first phenolic compound includes vanillin, and the second phenolic compound includes vanillate.

In some embodiments, the first synthetic promoter includes a spacer region, wherein the spacer region includes: a first element including a nucleic acid sequence having at least 80% sequence identity to any one of SEQ ID NOs:22-25 or a complement thereof; a third element including a nucleic acid sequence having at least 80% sequence identity to any one of SEQ ID NOs:34-37 or a complement thereof; and a second element including a variable nucleic acid sequence disposed between the first and third elements.

In some embodiments, the second synthetic promoter including a spacer region, wherein the spacer region includes: a first element including a nucleic acid sequence having at least 80% sequence identity to any one of SEQ ID NOs:22-25 or a complement thereof; a third element including a nucleic acid sequence having at least 80% sequence identity to any one of SEQ ID NOs:34-37 or a complement thereof; and a second element including a variable nucleic acid sequence disposed between the first and third elements. In other embodiments, the first and second synthetic promoters are the same. In yet other embodiments, the first and second synthetic promoters are different.

In some embodiments, the first protein includes LigV.

In a fifth aspect, the present invention features a recombinant gene including a synthetic promoter (e.g., a phenolic-inducible synthetic promoter, including any described herein).

In a sixth aspect, the present invention features a recombinant vector including an expression cassette (e.g., any described herein).

In a seventh aspect, the present invention features a host cell including a modified gene that includes a synthetic promoter (e.g., a phenolic-inducible synthetic promoter, including any described herein) or a recombinant vector (e.g., any described herein).

In an eighth aspect, the present invention features a population of cells includes a modified gene that includes a synthetic promoter (e.g., a phenolic-inducible synthetic promoter, including any described herein) or a recombinant vector (e.g., any described herein). In particular embodiments, the population of cells includes cells induced with a phenolic compound (e.g., any described herein, such as vanillin) at a concentration of from about 0.1 mM to 100 mM (e.g., from 0.1 mM to 1 mM, 0.1 mM to 5 mM, 0.1 mM to 10 mM, 0.1 mM to 25 mM, 0.1 mM to 50 mM, 0.1 mM to 75 mM, 0.5 mM to 1 mM, 0.5 mM to 5 mM, 0.5 mM to 10 mM, 0.5 mM to 25 mM, 0.5 mM to 50 mM, 0.5 mM to 75 mM, 0.5 mM to 100 mM, 1 mM to 5 mM, 1 mM to 10 mM, 1 mM to 25 mM, 1 mM to 50 mM, 1 mM to 75 mM, 1 mM to 100 mM, 2 mM to 5 mM, 2 mM to 10 mM, 2 mM to 25 mM, 2 mM to 50 mM, 2 mM to 75 mM, 2 mM to 100 mM, 5 mM to 10 mM, 5 mM to 25 mM, 5 mM to 50 mM, 5 mM to 75 mM, 5 mM to 100 mM, 7 mM to 10 mM, 7 mM to 25 mM, 7 mM to 50 mM, 7 mM to 75 mM, 7 mM to 100 mM, 10 mM to 25 mM, 10 mM to 50 mM, 10 mM to 75 mM, 10 mM to 100 mM, 15 mM to 25 mM, 15 mM to 50 mM, 15 mM to 75 mM, 15 mM to 100 mM, 20 mM to 50 mM, 20 mM to 75 mM, 20 mM to 100 mM, 50 mM to 75 mM, 50 mM to 100 mM, or 80 mM to 100 mM).

In an eighth aspect, the present invention features a method of treating of treating lignin or a derivative thereof, the method including: introducing a host cell (e.g., any described herein) to a source including lignin or a derivative thereof. In some embodiments, the source includes one or more phenolic compounds, lignin, lignocellulose, or a lignin derivative.

In any embodiment herein, the phenolic compound (e.g., the first phenolic compound) includes vanillin, vanillic acid, ferulic acid, coumaric acid, syringaldehyde, syringate, or protocatechuate or a salt thereof or an anionic form thereof (e.g., a negatively charged form thereof). In some embodiments, the phenolic compound (e.g., the first phenolic compound) includes a structure of formula (I) or a salt thereof or an anionic form thereof (e.g., a negatively charged form thereof). In some embodiments of formula (I), which X is a bond (e.g., a covalent bond), an optionally substituted alkylene (e.g., as defined herein), an optionally substituted alkenylene (e.g., as defined herein), or an optionally substituted heteroalkylene (e.g., as defined herein); $R^1$ is H, optionally substituted alkyl (e.g., as defined herein), optionally substituted alkoxy (e.g., as defined herein), optionally substituted alkanoyl (e.g., as defined herein), carboxyaldehyde, optionally substituted carboxyaldehydealkyl (e.g., as defined herein), hydroxyl, optionally substituted hydroxyalkyl (e.g., as defined herein), thiol, optionally substituted thioalkoxy (e.g., as defined herein), carboxyalkyl, or a protecting group; each of $R^2$ is, independently, H or optionally substituted alkyl; and $R^3$ is H, optionally substituted alkyl (e.g., as defined herein), optionally substituted alkoxy (e.g., as defined herein), optionally substituted alkanoyl (e.g., as defined herein), or hydroxyl.

In any embodiment herein, the gene encodes for one or more proteins, in which one or more proteins (e.g., a first protein) can include any of the following: ADH, ALDH, AroY, BADH, BzaA, CatA, CatA2, CouP, DesA, DesB, DesV, DesZ, EcdB, Ech, ErdD, Fes, FerA, FerB, FerB2, FerC, FDC, HADH, HDE, HpvZ, LigA, LigB, LigC, LigD, LigE, LigF, LigG, LigH, LigI, LigJ, LigK, LigL, LigM, LigN, LigO, LigP, LigR, LigU, LigV, LigW, LigW2, LigX, LigY, LigZ, Lpdc, LsdA, MetF, PC ADC, pHB3H, pHBALS, pHBDC, PhcC, PhcD, pHCS, pHCHL, PinZ, PobA, TE, VanA, VanB, or Vdh.

In any embodiment herein, the gene encodes for one or more proteins, in which one or more proteins (e.g., a first protein) can include any of the following: a C-α-dehydrogenase, a β-etherase, a dioxygenase, a hydrolase, an aromatic transporter, a vanillin dehydrogenase, or a feruloyl-CoA synthetase.

In any embodiment herein, the gene encodes for one or more proteins, in which one or more proteins (e.g., a first protein) can include any of the following: an alcohol dehydrogenase, an aldehyde dehydrogenase, a benzaldehyde dehydrogenase, a benzaldehyde-derivative dehydrogenase, a C-α-dehydrogenase, a CHMS dehydrogenase, a CHA aldolase, a catechol dioxygenase, a choline dehydrogenase, a coumarate transporter, a decarboxylase subunit, an enoyl-CoA-hydratase, a β-etherase, a ferulic acid decarboxylase, a ferulic acid responsive repressor, a feruloyl-CoA synthetase, a feruloyl-CoA hydratase/lyase, a 10-formyltetrahydrofolate synthetase, a gallate demethylase, a gallate decarboxylase, a gallate dioxygenase, a glutathione lyase, a glutathione S-transferase, a 3-hydroxyacyl-CoA dehydrogenase, a hydroxylase, a β-hydroxypropiovanillone oxidase, a lignostilbene dioxygenase, a LysR-type transcriptional regulator, a methylene folate reductase, an OMA hydratase, an OMA tautomerase, a p-hydroxybenzoate decarboxylase, a p-hydroxybenzoate hydroxylase, a p-hydroxybenzaldehyde synthase, a p-hydroxycinnamoyl-CoA hydratase/lyase, a p-hydroxycinnamoyl-CoA synthetase, a phthalate dioxygenase, a phthalate hydrolase, a pinoresinol/lariciresinol reductase, a protocatechuate decarboxylase, a protocatechuate dioxygenase, a PDC hydrolase, a syringate O-demethylase, a thiolase, a vanillate decarboxylase, a vanillin dehydrogenase, and a vanillate demethylase oxygenase.

In any of the embodiments herein, a fragment can include a contiguous fragment, which in turn can include at least 5, 10, 11, 12, 13, 14, 15, 16, 17, 18, 19, 20, 21, 22, 23, 24, or 25 contiguous nucleotides from a full-length nucleic acid sequence. In some embodiments, the contiguous fragment includes of from about 5 to about 100 nucleotides (e.g., from 5 to 10, 5 to 25, 5 to 50, 5 to 75, 5 to 100, 10 to 25, 10 to 50, 10 to 75, 10 to 100, 20 to 25, 20 to 50, 20 to 75, 20 to 100, 25 to 50, 25 to 75, 25 to 100, 50 to 75, 50 to 100, or 75 to 100 nucleotides).

In any of the embodiments herein, a contiguous fragment can include at least 5, 6, 7, 8, 9, 10, 11, 12, 13, 14, 15, 16, 17, 18, 19, 20, 25, 50, 75, 90, 100, 150, 200, 250, 300, or 350 contiguous amino acids from a full-length amino acid sequence. In some embodiments, the contiguous fragment includes of from about 5 to about 350 amino acids (e.g., from 5 to 10, 5 to 25, 5 to 50, 5 to 75, 5 to 100, 5 to 150, 5 to 200, 5 to 250, 5 to 300, 10 to 25, 10 to 50, 10 to 75, 10 to 100, 10 to 150, 10 to 200, 10 to 250, 10 to 300, 10 to 350, 20 to 25, 20 to 50, 20 to 75, 20 to 100, 20 to 150, 20 to 200, 20 to 250, 20 to 300, 20 to 350, 25 to 50, 25 to 75, 25 to 100, 25 to 150, 25 to 200, 25 to 250, 25 to 300, 25 to 350, 50 to 75, 50 to 100, 50 to 150, 50 to 200, 50 to 250, 50 to 300, 50 to 350, 75 to 100, 75 to 150, 75 to 200, 75 to 250, 75 to 300, and 75 to 350 amino acids).

In any embodiment herein, at least 80% sequence identity to a reference sequence can include at least 85%, 90%, 95%, 96%, 97%, 98%, or 99% sequence identity to the reference sequence (e.g., the reference nucleic acid sequence or the reference amino acid sequence).

Definitions

As used herein, the term "about" means +/−10% of any recited value. As used herein, this term modifies any recited value, range of values, or endpoints of one or more ranges.

The term "acyl," or "alkanoyl," as used interchangeably herein, represent an alkyl group, as defined herein, or hydrogen attached to the parent molecular group through a carbonyl group, as defined herein. This group is exemplified by formyl, acetyl, propionyl, butanoyl, and the like. The alkanoyl group can be substituted or unsubstituted. For example, the alkanoyl group can be substituted with one or more substitution groups, as described herein for alkyl. In some embodiments, the unsubstituted acyl group is a $C_{2-7}$ acyl or alkanoyl group.

By "alkaryl" is meant an aryl group, as defined herein, attached to the parent molecular group through an alkylene group, as defined herein. Similarly, by the term "alkheteroaryl" is meant a heteroaryl group, as defined herein, attached to the parent molecular group through an alkylene group. Other groups preceded by the prefix "alk-" are defined in the same manner. The alkaryl group can be substituted or unsubstituted. For example, the alkaryl group can be substituted with one or more substitution groups, as described herein for alkyl and/or aryl. Exemplary unsubstituted alkaryl groups are of from 7 to 16 carbons ($C_{7-16}$ alkaryl), as well as those having an alkylene group with 1 to 6 carbons and an aryl group with 4 to 18 carbons (i.e., $C_{1-6}$ alk-$C_{4-18}$ aryl).

By "alkenyl" is meant an optionally substituted $C_{2-24}$ alkyl group having one or more double bonds. The alkenyl group can be cyclic (e.g., $C_{3-24}$ cycloalkenyl) or acyclic. The alkenyl group can also be substituted or unsubstituted. For example, the alkenyl group can be substituted with one or more substitution groups, as described herein for alkyl.

By "alkenylene" is meant a multivalent (e.g., bivalent, trivalent, tetravalent, etc.) form of an alkenyl group, as described herein. In some embodiments, the alkenylene group is a $C_{2-3}$, $C_{2-6}$, $C_{2-12}$, $C_{2-16}$, $C_{2-18}$, $C_{2-20}$, or $C_{2-24}$ alkylene group. The alkenylene group can be branched or unbranched. The alkenylene group can also be substituted or unsubstituted. For example, the alkenylene group can be substituted with one or more substitution groups, as described herein for alkyl.

By "alkoxy" is meant —OR, where R is an optionally substituted alkyl group, as described herein. Exemplary alkoxy groups include methoxy, ethoxy, butoxy, trihaloalkoxy, such as trifluoromethoxy, etc. The alkoxy group can be substituted or unsubstituted. For example, the alkoxy group can be substituted with one or more substitution groups, as described herein for alkyl. Exemplary unsubstituted alkoxy groups include $C_{1-3}$, $C_{1-6}$, $C_{1-12}$, $C_{1-16}$, $C_{1-18}$, $C_{1-20}$, or $C_{1-24}$ alkoxy groups.

By "alkyl" and the prefix "alk" is meant a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic (e.g., $C_{3-24}$ cycloalkyl) or acyclic. The alkyl group can be branched or unbranched. The alkyl group can also be substituted or unsubstituted. For example, the alkyl group can be substituted with one, two, three or, in the case of alkyl groups of two carbons or more, four substituents independently selected from the group consisting of: (1) $C_{1-6}$ alkoxy (e.g., —OAk, in which Ak is an alkyl group, as defined herein); (2) $C_{1-6}$ alkylsulfinyl (e.g., —S(O)Ak, in which Ak is an alkyl group, as defined herein); (3) $C_{1-6}$ alkylsulfonyl (e.g., —SO$_2$Ak, in which Ak is an alkyl group, as defined herein); (4) amino (e.g., —NR$^{N1}$R$^{N2}$, where each of R$^{N1}$ and R$^{N2}$ is, independently, H or optionally substituted alkyl, or R$^{N1}$ and R$^{N2}$, taken together with the nitrogen atom to which each are attached, form a heterocyclyl group); (5) aryl; (6) arylalkoxy (e.g., —OA$^L$Ar, in which A$^L$ is an alkylene group and Ar is an aryl group, as defined herein); (7) aryloyl (e.g., —C(O)Ar, in which Ar is an aryl group, as defined herein); (8) azido (e.g., an —N$_3$ group); (9) cyano (e.g., a —CN group); (10) carboxyaldehyde (e.g., a —C(O)H group); (11) $C_{3-8}$ cycloalkyl; (12) halo; (13) heterocyclyl (e.g., a 5-, 6- or 7-membered ring, unless otherwise specified, containing one, two, three, or four non-carbon heteroatoms (e.g., independently selected from the group consisting of nitrogen, oxygen, phosphorous, sulfur, or halo)); (14) heterocyclyloxy (e.g., —OHet, in which Het is a heterocyclyl group); (15) heterocyclyloyl (e.g., —C(O) Het, in which Het is a heterocyclyl group); (16) hydroxyl (e.g., a —OH group); (17) N-protected amino; (18) nitro (e.g., an —NO$_2$ group); (19) oxo (e.g., an =O group); (20) $C_{3-8}$ spirocyclyl (e.g., an alkylene diradical, both ends of which are bonded to the same carbon atom of the parent group to form a spirocyclyl group); (21) $C_{1-6}$ thioalkoxy (e.g., —SAk, in which Ak is an alkyl group, as defined herein); (22) thiol (e.g., an —SH group); (23) —CO$_2$R$^A$, where R$^A$ is selected from the group consisting of (a) hydrogen, (b) $C_{1-6}$ alkyl, (c) $C_{4-18}$ aryl, and (d) $C_{1-6}$ alk-$C_{4-18}$ aryl; (24) —C(O)NR$^B$R$^C$, where each of R$^B$ and R$^C$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; (25) —SO$_2$R$^D$, where R$^G$ is selected from the group consisting of (a) $C_{1-6}$ alkyl, (b) $C_{4-18}$ aryl, and (c) $C_{1-6}$ alk-$C_{4-18}$ aryl; (26) —$SO_2NR^ER^F$, where each of $R^E$ and $R^F$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; and (27) —$NR^GR^H$, where each of $R^G$ and $R^H$ is, independently, selected from the group consisting of (a) hydrogen, (b) an N-protecting group, (c) $C_{1-6}$ alkyl, (d) $C_{2-6}$ alkenyl, (e) $C_{2-6}$ alkynyl, (f) $C_{4-18}$ aryl, (g) $C_{1-6}$ alk-$C_{4-18}$ aryl, (h) $C_{3-8}$ cycloalkyl, and (i) $C_{1-6}$ alk-$C_{3-8}$ cycloalkyl, wherein in one embodiment no two groups are bound to the nitrogen atom through a carbonyl group or a sulfonyl group. The alkyl group can be a primary, secondary, or tertiary alkyl group substituted with one or more substituents (e.g., one or more halo or alkoxy). In some embodiments, the unsubstituted alkyl group is a $C_{1-3}$, $C_{1-6}$, $C_{1-12}$, $C_{1-16}$, $C_{1-28}$, $C_{1-20}$, or $C_{1-24}$ alkyl group.

By "alkylene" is meant a multivalent (e.g., bivalent, trivalent, tetravalent, etc.) form of an alkyl group, as described herein. Exemplary alkylene groups include methylene, ethylene, propylene, butylene, etc. In some embodiments, the alkylene group is a $C_{1-3}$, $C_{1-6}$, $C_{1-2}$, $C_{1-16}$, $C_{4-18}$, $C_{1-20}$, $C_{1-24}$, $C_{2-3}$, $C_{2-6}$, $C_{2-12}$, $C_{2-16}$, $C_{2-18}$, $C_{2-20}$, or $C_{2-24}$ alkylene group. The alkylene group can be branched or unbranched. The alkylene group can also be substituted or unsubstituted.

For example, the alkylene group can be substituted with one or more substitution groups, as described herein for alkyl.

By "aryl" is meant a group that contains any carbon-based aromatic group including, but not limited to, benzyl, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one, two, three, four, or five substituents independently selected from the group consisting of: (1) $C_{1-6}$ alkanoyl (e.g., —C(O)Ak, in which Ak is an alkyl group, as defined herein); (2) $C_{1-6}$ alkyl; (3) $C_{1-6}$ alkoxy (e.g., —OAk, in which Ak is an alkyl group, as defined herein); (4) $C_{1-6}$ alkoxy-$C_{1-6}$ alkyl (e.g., an alkyl group, which is substituted with an alkoxy group —OAk, in which Ak is an alkyl group, as defined herein); (5) $C_{1-6}$ alkylsulfinyl (e.g., —S(O)Ak, in which Ak is an alkyl group, as defined herein); (6) $C_{1-6}$ alkylsulfinyl-$C_{1-6}$ alkyl (e.g., an alkyl group, which is substituted by an alkylsulfinyl group —S(O)Ak, in which Ak is an alkyl group, as defined herein); (7) $C_{1-6}$ alkylsulfonyl (e.g., —$SO_2$Ak, in which Ak is an alkyl group, as defined herein); (8) $C_{1-6}$ alkylsulfonyl-$C_{1-6}$ alkyl (e.g., an alkyl group, which is substituted by an alkylsulfonyl group —$SO_2$Ak, in which Ak is an alkyl group, as defined herein); (9) aryl; (10) amino (e.g., —$NR^{N1}R^{N2}$, where each of $R^{N1}$ and $R^{N2}$ is, independently, H or optionally substituted alkyl, or $R^{N1}$ and $R^{N2}$, taken together with the nitrogen atom to which each are attached, form a heterocyclyl group); (11) $C_{1-6}$ aminoalkyl (e.g., meant an alkyl group, as defined herein, substituted by an amino group); (12) heteroaryl; (13) $C_{1-6}$ alk-$C_{4-18}$ aryl (e.g., -$A^L$Ar, in which $A^L$ is an alkylene group and Ar is an aryl group, as defined herein); (14) aryloyl (e.g., —C(O)Ar, in which Ar is an aryl group, as defined herein); (15) azido (e.g., an —$N_3$ group); (16) cyano (e.g., a —CN group); (17) $C_{1-6}$ azidoalkyl (e.g., a —$N_3$ azido group attached to the parent molecular group through an alkyl group, as defined herein); (18) carboxyaldehyde (e.g., a —C(O)H group); (19) carboxyaldehyde-$C_{1-6}$ alkyl (e.g., -$A^L$C(O)H, in which $A^L$ is an alkylene group, as defined herein); (20) $C_{3-8}$ cycloalkyl; (21) $C_{1-6}$ alk-$C_{3-8}$ cycloalkyl (e.g., -$A^L$Cy, in which $A^L$ is an alkylene group and Cy is a cycloalkyl group, as defined herein); (22) halo (e.g., F, Cl, Br, or I); (23) $C_{1-6}$ haloalkyl (e.g., an alkyl group, as defined herein, substituted with one or more halo); (24) heterocyclyl; (25) heterocyclyloxy (e.g., —OHet, in which Het is a heterocyclyl group); (26) heterocyclyloyl (e.g., —C(O)Het, in which Het is a heterocyclyl group); (16) hydroxyl (e.g., a —OH group); (27) hydroxyl (e.g., a —OH group); (28) $C_{1-6}$ hydroxy alkyl (e.g., an alkyl group, as defined herein, substituted by one to three hydroxyl groups, with the proviso that no more than one hydroxyl group may be attached to a single carbon atom of the alkyl group); (29) nitro (e.g., an —$NO_2$ group); (30) $C_{1-6}$ nitroalkyl (e.g., an alkyl group, as defined herein, substituted by one to three nitro groups); (31) N-protected amino; (32) N-protected amino-$C_{1-6}$ alkyl; (33) oxo (e.g., an =O group); (34) $C_{1-6}$ thioalkoxy (e.g., —SAk, in which Ak is an alkyl group, as defined herein); (35) thio-$C_{1-6}$ alkoxy-$C_{1-6}$ alkyl (e.g., an alkyl group, which is substituted by an thioalkoxy group —SAk, in which Ak is an alkyl group, as defined herein); (36) —$(CH_2)_rCO_2R^A$ where r is an integer of from zero to four, and $R^A$ is selected from the group consisting of (a) hydrogen, (b) $C_{1-6}$ alkyl, (c) $C_{4-18}$ aryl, and (d) $C_{1-6}$ alk-$C_{4-18}$ aryl; (37) —$(CH_2)_rCONR^BR^C$, where r is an integer of from zero to four and where each $R^B$ and $R^C$ is independently selected from the group consisting of (a) hydrogen, (b) $C_{1-6}$ alkyl, (c) $C_{4-18}$ aryl, and (d) $C_{1-6}$ alk-$C_{4-18}$ aryl; (38) —$(CH_2)_rSO_2R^D$, where r is an integer of from zero to four and where $R^u$ is selected from the group consisting of (a) $C_{1-6}$ alkyl, (b) $C_{4-18}$ aryl, and (c) $C_{1-6}$ alk-$C_{4-18}$ aryl; (39) —$(CH_2)_rSO_2NR^ER^F$, where r is an integer of from zero to four and where each of $R^E$ and $R^F$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; (40) —$(CH_2)_rNR^GR^H$, where r is an integer of from zero to four and where each of $R^G$ and $R^H$ is, independently, selected from the group consisting of (a) hydrogen, (b) an N-protecting group, (c) $C_{1-6}$ alkyl, (d) $C_{2-6}$ alkenyl, (e) $C_{2-6}$ alkynyl, (f) $C_{4-18}$ aryl, (g) $C_{1-6}$ alk-$C_{4-18}$ aryl, (h) $C_{3-8}$ cycloalkyl, and (i) $C_{1-6}$ alk-$C_{3-8}$ cycloalkyl, wherein in one embodiment no two groups are bound to the nitrogen atom through a carbonyl group or a sulfonyl group; (41) thiol; (42) perfluoroalkyl (e.g., an alkyl group, as defined herein, having each hydrogen atom substituted with a fluorine atom); (43) perfluoroalkoxy (e.g., —ORf, in which Rf is an alkyl group, as defined herein, having each hydrogen atom substituted with a fluorine atom); (44) aryloxy (e.g., —OAr, where Ar is an optionally substituted aryl group, as described herein); (45) cycloalkoxy (e.g., —OCy, in which Cy is a cycloalkyl group, as defined herein); (46) cycloalkylalkoxy (e.g., —O$A^L$Cy, in which $A^L$ is an alkylene group and Cy is a cycloalkyl group, as defined herein); and (47) arylalkoxy (e.g., —O$A^L$Ar, in which $A^L$ is an alkylene group and Ar is an aryl group, as defined herein). In particular embodiments, an unsubstituted aryl group is a $C_{4-18}$, $C_{4-14}$, $C_{4-12}$, $C_{4-10}$, $C_{6-18}$, $C_{6-14}$, $C_{6-12}$, or $C_{6-10}$ aryl group.

By "carboxyaldehyde" is meant a —C(O)H group.

By "carboxyaldehydealkyl" is meant a carboxyaldehyde group, as defined herein, attached to the parent molecular group through an alkylene group, as defined herein.

By "carboxyl" is meant a —$CO_2$H group.

By "carboxyalkyl" is meant a carboxyl group, as defined herein, attached to the parent molecular group through an alkylene group, as defined herein.

By "heteroalkylene" is meant an alkylene group, as described herein, having at least one heteroatom incorporated therein. Examples of heteroatoms include, but are not limited to, nitrogen, oxygen, sulfur, and phosphorus. In some embodiments, the heteroalkylene group is a $C_{1-3}$, $C_{1-6}$, $C_{1-12}$, $C_{1-16}$, $C_{1-18}$, $C_{1-20}$, or $C_{1-24}$ alkylene group. The heteroalkylene group can be branched or unbranched. The heteroalkylene group can also be substituted or unsubstituted. For example, the heteroalkylene group can be substituted with one or more substitution groups, as described herein for alkyl.

By "hydroxyl" is meant —OH.

By "hydroxyalkyl" is meant an alkyl group, as defined herein, substituted by one to three hydroxyl groups, with the proviso that no more than one hydroxyl group may be attached to a single carbon atom of the alkyl group and is exemplified by hydroxymethyl, dihydroxypropyl, and the like.

By "protecting group" is meant any group intended to protect a reactive group against undesirable synthetic reactions. Commonly used protecting groups are disclosed in "Greene's Protective Groups in Organic Synthesis," John Wiley & Sons, New York, 2007 (4th ed., eds. P. G. M. Wuts and T. W. Greene), which is incorporated herein by reference. O-protecting groups include an optionally substituted alkyl group (e.g., forming an ether with reactive group O), such as methyl, methoxymethyl, methylthiomethyl, benzoyloxymethyl, t-butoxymethyl, etc.; an optionally substituted alkanoyl group (e.g., forming an ester with the reactive group O), such as formyl, acetyl, chloroacetyl, fluoroacetyl (e.g., perfluoroacetyl), methoxyacetyl, pivaloyl, t-butylacetyl, phenoxyacetyl, etc.; an optionally substituted aryloyl group (e.g., forming an ester with the reactive group O), such as —C(O)—Ar, including benzoyl; an optionally substituted alkylsulfonyl group (e.g., forming an alkyl sulfonate with reactive group O), such as —SO$_2$—R$^{S1}$, where R$^{S1}$ is optionally substituted $C_{1-12}$ alkyl, such as mesyl or benzylsulfonyl; an optionally substituted arylsulfonyl group (e.g., forming an arylsulfonate with reactive group O), such as —SO$_2$—R$^{S4}$, where R$^{S4}$ is optionally substituted $C_{4-18}$ aryl, such as tosyl or phenylsulfonyl; an optionally substituted alkoxycarbonyl or aryloxycarbonyl group (e.g., forming a carbonate with reactive group O), such as —C(O)—OR$^{T1}$, where R$^{T1}$ is optionally substituted $C_{1-12}$ alkyl or optionally substituted $C_{4-18}$ aryl, such as methoxycarbonyl, methoxymethylcarbonyl, t-butyloxycarbonyl (Boc), or benzyloxycarbonyl (Cbz); or an optionally substituted silyl group (e.g., forming a silyl ether with reactive group O), such as —Si—(R$^{T2}$)$_3$, where each R$^{T2}$ is, independently, optionally substituted $C_{1-12}$ alkyl or optionally substituted $C_{4-18}$ aryl, such as trimethylsilyl, t-butyldimethylsilyl, or t-butyldiphenylsilyl. N-protecting groups include, e.g., formyl, acetyl, benzoyl, pivaloyl, t-butylacetyl, alanyl, phenyl sulfonyl, benzyl, Boc, and Cbz. Such protecting groups can employ any useful agent to cleave the protecting group, thereby restoring the reactivity of the unprotected reactive group.

By "salt" is meant an ionic form of a compound or structure (e.g., any formulas, compounds, or compositions described herein), which includes a cation or anion compound to form an electrically neutral compound or structure. Salts (e.g., simple salts having binary compounds, double salts, triple salts, etc.) are well known in the art. For example, salts are described in Berge S M et al., "Pharmaceutical salts," *J. Pharm. Sci.* 1977 January; 66(1):1-19; International Union of Pure and Applied Chemistry, "Nomenclature of Inorganic Chemistry," Butterworth & Co. (Publishers) Ltd., London, England, 1971 (2nd ed.); and in "Handbook of Pharmaceutical Salts: Properties, Selection, and Use," Wiley-VCH, April 2011 (2nd rev. ed., eds. P. H. Stahl and C. G. Wermuth). The salts can be prepared in situ during the final isolation and purification of the compounds of the invention or separately by reacting the free base group with a suitable organic acid (thereby producing an anionic salt) or by reacting the acid group with a suitable metal or organic salt (thereby producing a cationic salt). Representative anionic salts include acetate, adipate, alginate, ascorbate, aspartate, benzenesulfonate, benzoate, bicarbonate, bisulfate, bitartrate, borate, bromide, butyrate, camphorate, camphorsulfonate, chloride, citrate, cyclopentanepropionate, digluconate, dihydrochloride, diphosphate, dodecylsulfate, edetate, ethanesulfonate, fumarate, glucoheptonate, glucomate, glutamate, glycerophosphate, hemisulfate, heptonate, hexanoate, hydrobromide, hydrochloride, hydroiodide, hydroxyethanesulfonate, hydroxynaphthoate, iodide, lactate, lactobionate, laurate, lauryl sulfate, malate, maleate, malonate, mandelate, mesylate, methanesulfonate, methylbromide, methylnitrate, methyl sulfate, mucate, 2-naphthalenesulfonate, nicotinate, nitrate, oleate, oxalate, palmitate, pamoate, pectinate, persulfate, 3-phenylpropionate, phosphate, picrate, pivalate, polygalacturonate, propionate, salicylate, stearate, subacetate, succinate, sulfate, tannate, tartrate, theophyllinate, thiocyanate, triethiodide, toluenesulfonate, undecanoate, valerate salts, and the like. Representative cationic salts include metal salts, such as alkali or alkaline earth salts, e.g., barium, calcium (e.g., calcium edetate), lithium, magnesium, potassium, sodium, and the like; other metal salts, such as aluminum, bismuth, iron, and zinc; as well as nontoxic ammonium, quaternary ammonium, and amine cations, including, but not limited to ammonium, tetramethylammonium, tetraethylammonium, methylamine, dimethylamine, trimethylamine, triethylamine, ethylamine, pyridinium, and the like. Other cationic salts include organic salts, such as chloroprocaine, choline, dibenzylethylenediamine, diethanolamine, ethylenediamine, methylglucamine, and procaine.

By "thioalkoxy" is meant an alkyl group, as defined herein, attached to the parent molecular group through a sulfur atom. Exemplary unsubstituted thioalkoxy groups include $C_{1-6}$ thioalkoxy.

By "thiol" is meant an —SH group.

The terms "polynucleotide" and "nucleic acid," used interchangeably herein, refer to a polymeric form of nucleotides of any length, either ribonucleotides or deoxyribonucleotides. Thus, this term includes, but is not limited to, single-stranded (e.g., sense or antisense), double-stranded, or multi-stranded ribonucleic acids (RNAs), deoxyribonucleic acids (DNAs), threose nucleic acids (TNAs), glycol nucleic acids (GNAs), peptide nucleic acids (PNAs), locked nucleic acids (LNAs), or hybrids thereof, genomic DNA, cDNA, DNA-RNA hybrids, or a polymer comprising purine and pyrimidine bases or other natural, chemically or biochemically modified, non-natural, or derivatized nucleotide bases. Polynucleotides can have any useful two-dimensional or three-dimensional structure or motif, such as regions including one or more duplex, triplex, quadruplex, hairpin, and/or pseudoknot structures or motifs.

The term "modified," as used in reference to nucleic acids, means a nucleic acid sequence including one or more modifications to the nucleobase, nucleoside, nucleotide, phosphate group, sugar group, and/or internucleoside linkage (e.g., phosphodiester backbone, linking phosphate, or a phosphodiester linkage).

The nucleoside modification may include, but is not limited to, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, $N^4$-acetylcytidine, 5-formylcytidine, $N^4$-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyl adenosine, $N^6$-methyladenosine, $N^6$-isopentenyladenosine, $N^6$-(cis-hydroxy-isopentenyl) adenosine, 2-methylthio-$N^6$-(cis-hydroxyisopentenyl) adenosine, $N^6$-glycinylcarbamoyl adenosine, $N^6$-threonylcarbamoyladenosine, 2-methylthio-$N^6$-threonyl carbamoyladenosine, $N^6,N^6$-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, $N^2$-methylguanosine, $N^2,N^2$-dimethylguanosine, 8-oxo-guanosine, 7-methyl-8-oxo-guanosine, 1-methyl-6-thio-guanosine, $N^2$-methyl-6-thio-guanosine, and $N^2,N^2$-dimethyl-6-thio-guanosine, and combinations thereof.

A sugar modification may include, but is not limited to, a locked nucleic acid (LNA, in which the 2'-hydroxyl is connected by a $C_{1-6}$ alkylene (e.g., a multivalent (e.g., bivalent, trivalent, tetravalent, etc.) form of an alkyl group) or $C_{1-6}$ heteroalkylene (e.g., a divalent form of an alkylene group containing one, two, three, or four non carbon heteroatoms (e.g., independently selected from the group consisting of nitrogen, oxygen, phosphorous, sulfur, or halo) bridge to the 4'-carbon of the same ribose sugar), replacement of the oxygen in ribose (e.g., with S, Se, or alkylene, such as methylene or ethylene), addition of a double bond (e.g., to replace ribose with cyclopentenyl or cyclohexenyl), ring contraction of ribose (e.g., to form a 4-membered ring of cyclobutane or oxetane), ring expansion of ribose (e.g., to form a 6- or 7-membered ring having an additional carbon or heteroatom, such as for anhydrohexitol, altritol, mannitol, cyclohexanyl, cyclohexenyl, and morpholino that also has a phosphoramidate backbone), multicyclic forms (e.g., tricyclic), and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with a-L-threofuranosyl-(3'→2')), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a polynucleotide molecule can include nucleotides containing, e.g., arabinose, as the sugar.

A backbone modification may include, but is not limited to, 2'-deoxy- or T-O-methyl modifications. Exemplary modifications include modifications to the T position of a nucleic acid, such as 2'-O-methyl, 2'-halo (e.g., 2'-fluoro, 2'-chloro, 2'-bromo, or 2-iodo), 2'-alkyl (e.g., T-methyl, T-ethyl, T-propyl, 2'-allyl, etc., in which alkyl can be an optionally substituted alkyl, as defined herein), 2'-aryl (e.g., 2'-phenyl, in which aryl can be an optionally substituted aryl, as defined herein), 2'-alkaryl (e.g., 2'-benzyl, in which alkaryl can be an aryl group, as defined herein, attached to the parent molecular group through an alkylene group, in which an alkylene group can be a multivalent (e.g., bivalent, trivalent, tetravalent, etc.) form of an alkyl group, as described herein), 2'-amino (e.g., 2'-$NH_2$, etc., in which amino can be $NR^{N1}R^{N2}$, where each of $R^{N1}$ and $R^{N2}$ is, independently, H, alkyl, or alkaryl, or $R^{N1}$ and $R^{N2}$, taken together with the nitrogen atom to which each are attached, form a heterocyclyl group), 2'-alkoxy (e.g. 2'-O-methoxy, 2'-O-ethoxy, etc., in which alkoxy can be —OR, where R is an optionally substituted alkyl group, as described herein), 2'-alkylamino (e.g., 2'-O-methylamino, 2'-O-ethylamino, etc.), 2'-O-alkylamino (e.g., 2'-O-methylamino, 2'-O-ethylamino, etc., in which alkylamino can be an alkyl group, as defined herein, substituted by an amino group, as defined herein), 2'-azido (in which azido is an —$N_3$ group), 2'-O-cyanoalkyl (e.g., 2'-O-cyanomethyl, etc., in which cyanoalkyl can be an alkyl group, as defined herein, substituted by a cyano group (a —CN group)), 2'-O-alkoxyalkyl (e.g., 2'-O-(2-methoxyethyl), etc., in which alkoxyalkyl can be an alkyl group, as defined herein, which is substituted with an alkoxy group, as defined herein), etc.

A phosphate group modification may include, but is not limited to, phosphorothioate, phosphoroselenates, boranophosphates, boranophosphate esters, hydrogen phosphonates, phosphoramidates, phosphorodiamidates, alkyl or aryl phosphonates, phosphotriesters, phosphorodithioates, bridged phosphoramidates, bridged phosphorothioates, or bridged methylene-phosphonates.

"Complementarity" or "complementary" refers to the ability of a nucleic acid to form hydrogen bond(s) with another nucleic acid sequence by either traditional Watson-Crick or other non-traditional types, e.g., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C). In addition, it is also known in the art that for hybridization between two RNA molecules (e.g., dsRNA), guanine (G) base pairs with uracil (U). A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" or "sufficient complementarity" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

Unless otherwise indicated, abbreviations for nucleotides include A or a (adenine), G or g (guanine), C or c (cytosine), T or t (thymidine), U or u (uracil), r (g or a), y (t/u or c), m (a or c), k (g or t/u), s (g or c), w (a or t/u), b (g or c or t/u; or not a), d (a or g or t/u; or not c), h (a or c or t/u; or not g), v (a or g or c; or not t; or not u), and n (a or g or c or t/u or absent or other).

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter, "Overview of principles of hybridization and the strategy of nucleic acid probe assay," Elsevier, N. Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. A "complement" can include a "reverse complement," in which a given sequence is reversed to provide a reverse sequence and then a complement, as defined herein, of that reverse sequence provides a reverse complement. Hybridization and washing conditions are well known and exemplified in Sambrook J, Fritsch E F, and Maniatis T, "Molecular Cloning: A Laboratory Manual," Second Edition, Cold Spring Harbor Laboratory Press, Cold Spring Harbor (1989), particularly Chapter 11 and Table 11.1 therein; and Sambrook J and Russell W, "Molecular Cloning: A Laboratory Manual," Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g., complementarity over 35 or less, 30 or less, 25 or less, 22 or less, 20 or less, or 18 or less nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides). Furthermore, the skilled artisan will recognize that the temperature and wash solution salt concentration may be adjusted as necessary, according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul S F et al., *J. Mol. Biol.* 1990; 215:403-10; Zhang J et al., *Genome Res.* 1997; 7:649-56) or by using the Gap program (Wisconsin Sequence Analysis Package, Version 8 for Unix, Genetics Computer Group, University Research Park, Madison Wis.), using default settings, which uses the algorithm of Smith T F et al., *Adv. Appl. Math.* 1981; 2(4):482-9).

By "protein," "peptide," or "polypeptide," as used interchangeably, is meant any chain of more than two amino acids, regardless of post-translational modification (e.g., glycosylation or phosphorylation), constituting all or part of a naturally occurring polypeptide or peptide, or constituting a non-naturally occurring polypeptide or peptide, which can include coded amino acids, non-coded amino acids, modified amino acids (e.g., chemically and/or biologically modified amino acids), and/or modified backbones.

The term "fragment" is meant a portion of a nucleic acid or a polypeptide that is at least one nucleotide or one amino acid shorter than the reference sequence. This portion contains, preferably, at least about 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1250, 1500, 1750, 1800 or more nucleotides; or 10, 20, 30, 40, 50, 60, 70, 80, 90, 100, 150, 200, 250, 300, 350, 400, 450, 500, 550, 600, 640 amino acids or more. In another example, any polypeptide fragment can include a stretch of at least about 5 (e.g., about 10, about 20, about 30, about 40, about 50, or about 100) amino acids that are at least about 40% (e.g., about 50%, about 60%, about 70%, about 80%, about 90%, about 95%, about 87%, about 98%, about 99%, or about 100%) identical to any of the sequences described herein can be utilized in accordance with the invention. In certain embodiments, a polypeptide to be utilized in accordance with the invention includes 2, 3, 4, 5, 6, 7, 8, 9, 10, or more mutations (e.g., one or more conservative amino acid substitutions, as described herein). In yet another example, any nucleic acid fragment can include a stretch of at least about 5 (e.g., about 7, about 8, about 10, about 12, about 14, about 18, about 20, about 24, about 28, about 30, or more) nucleotides that are at least about 40% (about 50%, about 60%, about 70%, about 80%, about 90%, about 95%, about 87%, about 98%, about 99%, or about 100%) identical to any of the sequences described herein can be utilized in accordance with the invention.

The term "conservative amino acid substitution" refers to the interchangeability in proteins of amino acid residues having similar side chains (e.g., of similar size, charge, and/or polarity). For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamic acid and aspartic acid; and a group of amino acids having sulfur containing side chains consists of cysteine and methionine. Exemplary conservative amino acid substitution groups are valine-leucine-isoleucine, phenylalanine-tyrosine, lysine-arginine, alanine-valine, glycine-serine, glutamate-aspartate, and asparagine-glutamine.

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith T F et al., *J. Mol. Biol.* 1981; 147:195-7) and BLAST (Basic Local Alignment Search Tool; Altschul S F et al., *J. Mol. Biol.* 1990; 215:403-10). These and other alignment algorithms are accessible using publicly available computer software such as "Best Fit" (Smith T F et al., *Adv. Appl. Math.* 1981; 2(4):482-9) as incorporated into GeneMatcher Plus™ (Schwarz and Dayhof, "Atlas of Protein Sequence and Structure," ed. Dayhoff, M. O., pp. 353-358, 1979), BLAST, BLAST-2, BLAST-P, BLAST-N, BLAST-X, WU-BLAST-2, ALIGN, ALIGN-2, CLUSTAL, T-COFFEE, MUSCLE, MAFFT, or Megalign (DNASTAR). In addition, those skilled in the art can determine appropriate parameters for measuring alignment, including any algorithms needed to achieve optimal alignment over the length of the sequences being compared. In general, for polypeptides, the length of comparison sequences can be at least five amino acids, preferably 10, 20, 30, 40, 50, 60, 70, 80, 90, 100, 125, 150, 175, 200, 250, 300, 400, 500, 600, 700, or more amino acids, up to the entire length of the polypeptide. For nucleic acids, the length of comparison sequences can generally be at least 10, 20, 30, 40, 50, 60, 70, 80, 90, 100, 125, 150, 175, 200, 250, 300, 400, 500, 600, 700, 800, 900, 1000, 1100, 1200, 1300, 1400, 1500, 1600, 1700, 1800, 1900, 2000, 2100, or more nucleotides, up to the entire length of the nucleic acid molecule. It is understood that for the purposes of determining sequence identity when comparing a DNA sequence to an RNA sequence, a thymine nucleotide is equivalent to an uracil nucleotide.

By "substantial identity" or "substantially identical" is meant a polypeptide or nucleic acid sequence that has the same polypeptide or nucleic acid sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least about 50%, 60%, 70%, 75%, 80%, 85%, 90%, 95%, 96%, 97%, 98%, 99%, or 100% sequence identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length amino acid sequence). For nucleic acids, the length of comparison sequences will generally be at least 5, 10, 11, 12, 13, 14, 15, 16, 17, 18, 19, 20, 21, 22, 23, 24, or 25 contiguous nucleotides (e.g., the full-length nucleotide sequence). Sequence identity may be measured using sequence analysis software on the default setting (e.g., Sequence Analysis Software Package of the Genetics Computer Group, University of Wisconsin Biotechnology Center, 1710 University Avenue, Madison, Wis., 53705). Such software may match similar sequences by assigning degrees of homology to various substitutions, deletions, and other modifications.

A "host," as used herein, denotes an in vivo or in vitro eukaryotic cell, a prokaryotic cell (e.g., bacterial or archaeal cell), or a cell from a multicellular organism (e.g., a cell line) cultured as a unicellular entity, which eukaryotic or prokaryotic cells can be, or have been, used as recipients for a nucleic acid, and include the progeny of the original cell which has been transformed by the nucleic acid. It is understood that the progeny of a single cell may not necessarily be completely identical in morphology or in genomic or total DNA complement as the original parent, due to natural, accidental, or deliberate mutation. A "recombinant host" (also referred to as a "genetically modified host cell") is a host cell into which has been introduced a heterologous nucleic acid, e.g., an expression vector. For example, a subject bacterial host cell is a genetically modified bacterial host cell by virtue of introduction into a suitable bacterial host cell of an exogenous nucleic acid (e.g., a plasmid or recombinant expression vector) and a subject eukaryotic host cell is a genetically modified eukaryotic host cell (e.g., a mammalian germ cell), by virtue of introduction into a suitable eukaryotic host cell of an exogenous nucleic acid.

By "linker" is meant any useful multivalent (e.g., bivalent) component useful for joining to different portions or segments. Exemplary linkers include a nucleic acid sequence, a chemical linker (e.g., an alkylene group such as a multivalent (e.g., bivalent, trivalent, tetravalent, etc.) form of an alkyl group, as described herein; a heteroalkylene group such as a divalent form of an alkylene group, as defined herein, containing one, two, three, or four non carbon heteroatoms (e.g., independently selected from the group consisting of nitrogen, oxygen, phosphorous, sulfur, or halo); or an ethylene glycol group, e.g., $-OCH_2CH_2-$, including a poly(ethylene glycol) (PEG) group $-(OCH_3CH_2)_2-$, in which n is any useful number in any of these (e.g., any useful n to provide any useful number average molar mass $M_n$)), etc.

A "vector" or "expression vector" is a replicon, such as plasmid, phage, virus, or cosmid, to which another nucleic acid segment, i.e., an "insert", may be attached so as to bring about the replication of the attached segment in a cell.

An "expression cassette" comprises a nucleic acid coding sequence operably linked, as defined herein, to a promoter sequence. Exemplary promoter sequences can include a nucleic acid regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation, as well as protein binding domains (consensus sequences) responsible for the binding of RNA polymerase. Eukaryotic promoters will often, but not always, contain "TATA" boxes and "CAT" boxes. Prokaryotic promoters can contain Shine-Dalgarno sequences in addition to the −10 and −35 consensus sequences.

An "expression control sequence" can be a nucleic acid sequence that controls and regulates the transcription and translation of another nucleic acid sequence. A coding sequence is "under the control" of transcriptional and translational control sequences in a cell when RNA polymerase transcribes the coding sequence into mRNA, which is then translated into the protein encoded by the coding sequence. Exemplary transcriptional and translational control sequences are DNA regulatory sequences, such as promoters, enhancers, polyadenylation signals, terminators, and the like, that provide for the expression of a coding sequence in a host cell.

"Operably linked" or "operatively linked" or "operatively associated with," as used interchangeably, refers to a juxtaposition wherein the components so described are in a relationship permitting them to function in their intended manner. For instance, a promoter is operably linked to a coding sequence if the promoter affects its transcription or expression. A nucleic acid molecule is operatively linked or operably linked to, or operably associated with, an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL.

By "attaching," "attachment," or related word forms is meant any covalent or non-covalent bonding interaction between two components. Non-covalent bonding interactions include, without limitation, hydrogen bonding, ionic interactions, halogen bonding, electrostatic interactions, n bond interactions, hydrophobic interactions, inclusion complexes, clathration, van der Waals interactions, and combinations thereof.

As used herein, the terms "top," "bottom," "upper," "lower," "above," and "below" are used to provide a relative relationship between structures.

Other features and advantages of the invention will be apparent from the following description and the claims.

BRIEF DESCRIPTION OF THE DRAWINGS

FIG. 11 shows exemplary promoter sequences (SEQ ID NOs:1-9).

FIG. 12 shows exemplary sequences of promoter regions (SEQ ID NOs:10-42).

DETAILED DESCRIPTION OF THE INVENTION

Figure 1A:
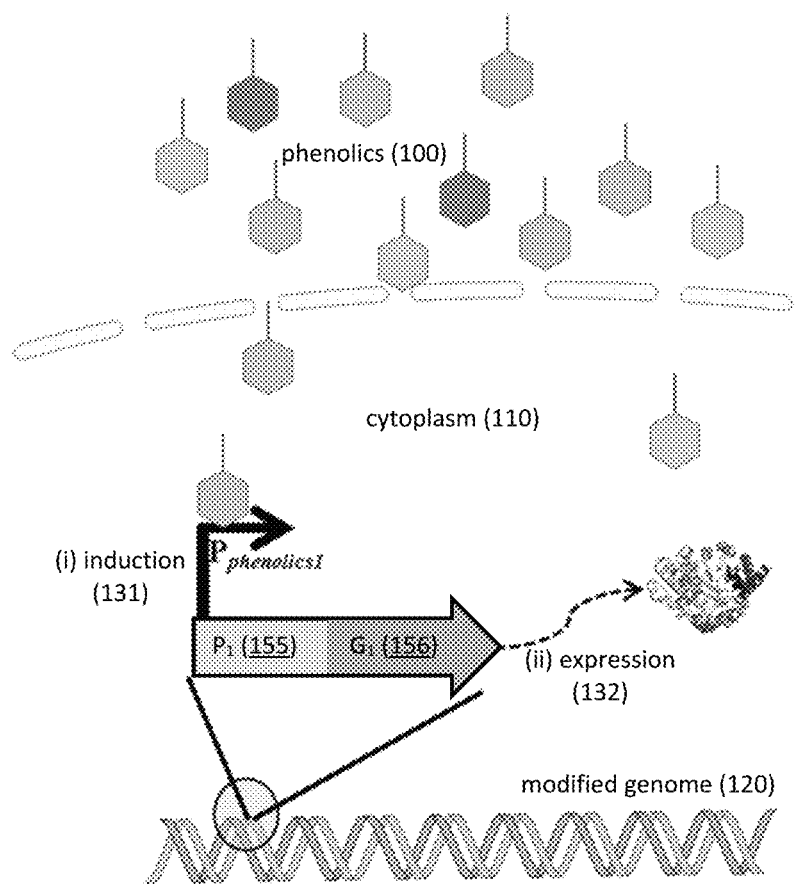
FIG. 1A-1C shows exemplary lignin valorization chassis engineered with a phenolic-inducible promoter. Provided are schematics of (A) phenolic-inducible expression of a construct including a promoter $P_1$ 155 and a gene $G_1$ 156, (B) an exemplary promoter 150 and its regions, and (C) an exemplary phenolic compound having a structure of formula (I).

The present invention relates, in part, to a synthetic promoter and methods thereof. In particular embodiments, the synthetic promoter is a phenolic-inducible synthetic promoter, in which one or more phenolic compounds facilitate the transcription of a gene and/or binding of a polymerase to one or more promoter sites. FIG. 1A describes use of an exemplary synthetic, exogenous promoter for in situ expression of a gene in the presence of a phenolic compound. As can be seen, one or more phenolic compounds 100 can initially pass through a host cell membrane and into the cytoplasm 110. The host cell can be altered to include a modified genome 120 having a phenolic-inducible synthetic promoter $P_1$ 155 operably linked to a gene $G_1$ 156. The presence of an appropriate phenolic compound (e.g., a first phenolic compound) facilitates induction 131 by, e.g., enhanced binding of a polymerase to a site in the synthetic promoter of the modified gene, which in turn provides expression 132 of the gene (e.g., a first gene, thereby providing a first protein). In this manner, expression can be tuned to be controlled by the presence of particular phenolic compound(s), which provides particularized protein expression.

Figure 1B:
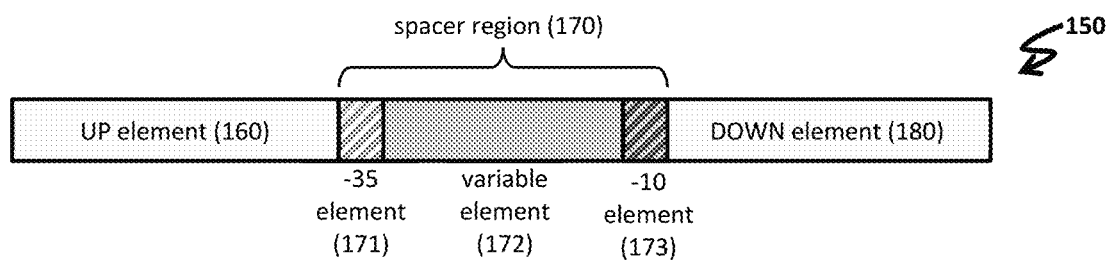

The synthetic promoter can include any useful regions or sites to bind a polymerase (e.g., an RNA polymerase), interact with transcription factor(s), recognize phenolic compound(s), and/or facilitate protein expression. FIG. 1B provides a schematic of an exemplary synthetic promoter 150 including various regions, including a spacer region 170 (e.g., a variable region), an UP element 160 positioned upstream of the spacer region, and a DOWN element 180 positioned downstream of the spacer region.

Exemplary sequences for synthetic promoters (or a portion thereof) are provided in FIG. 11 (SEQ ID NOs:1-9), in which n can be any nucleotide or a nucleotide present at the same position in an optimally aligned sequence (e.g., optimally aligned to any sequence herein, in which optimal alignment can be determined as described herein).

As can be seen, the spacer region is disposed between the UP and DOWN elements. The spacer region 170 can further include regions that facilitate polymerase recognition. For instance, the spacer region 170 can include a first element 171 (e.g., a −35 element), a second element 172 (e.g., a variable element), and a third element 173 (e.g., a −10 element).

Exemplary sequences for regions of synthetic promoters or spacer regions are provided in FIG. 12 (SEQ ID NOs: 10-42), in which n can be any nucleotide or a nucleotide present at the same position in an optimally aligned sequence (e.g., optimally aligned to any sequence herein, in which optimal alignment can be determined as described herein).

Synthetic promoters can be provided to a host cell in any useful manner or form. In one non-limiting instance, the synthetic promoter is provided as an expression cassette, in which a gene is operably linked to the synthetic promoter (e.g., located downstream of the synthetic promoter and/or linked by one or more covalent bonds or nucleic acid sequence(s)). The desired gene can have any useful property. In one non-limiting instance, the gene (e.g., a first gene) encodes a protein (e.g., a first protein) that is beneficial for degrading or breaking down lignin or a lignin derivative. The expression cassette can then provide one or more modified portions of the host cell's genome.

One or more expression cassettes can be designed to facilitate a dynamic regulator system, in which delivery of such expression cassette(s) to a host cell can establish one or more modified gene regions within the host. For instance and without limitation, a first phenolic compound that induces expression can result in expression of a first protein, which interacts with a substrate to produce the first phenolic compound. In this instance, a feedback-type loop can be established, in which presence of the first phenolic compound induces an in situ biological network to produce additional first phenolic compounds. For example, a feedback-type loop can be established by having a vanillin-inducible synthetic promoter operable linked to a nucleic acid encoding a LigF gene. Then, the presence of vanillin would promote expression of the LigF protein, which in turn will increase cellular concentrations of LigF to convert a substrate (e.g., MPHPV) into vanillin. Further increases in vanillin using this feedback-type loop could further stimulate production of LigF by way of the vanillin-inducible synthetic promoter.

Figure 2A:
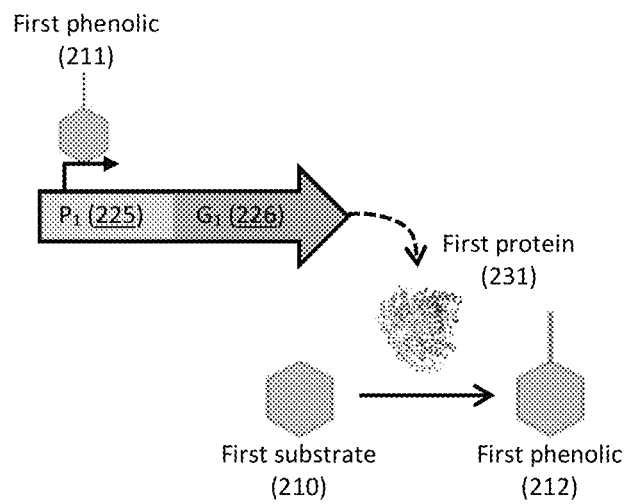
FIG. 2A-2C shows schematics of (A) a first exemplar dynamic regulator system that employs inducible promoters, (B) a second exemplary dynamic regulator system that employs inducible promoters, and (C) a reaction network of breakdown of various lignin components into phenolic compounds. Abbreviations include 5,5'-dehydrodivanillate (DDVA), 2,2',3-trihydroxy-3'-methoxy-5,5'-dicarboxybiphenyl (OH-DDVA), 5-carboxyvanillate (5CVA), guaiacylglycerol-β-guaiacyl ether (GGE), syringylglycerol-β-guaiacyl ether (SGE), syringylglycerol-β-syringyl ether (SSE), α-(2-methoxyphenoxy)-β-hydroxypropiovanillone (MPHPV), α-(2-methoxyphenoxy)-β-hydroxypropiosyringone (MPHPS), β-hydroxypropiovanillone (HPV), β-hydroxypropiosyringone (HPS), protocatechuate (PCA), cis, ev.v-muconic acid (CCMA), 3-O-methylgallate (3MGA), 2-pyrone-4,6-dicarboxylate (PDC), and dehydrodiconiferyl alcohol (DCA). Other abbreviations are described herein.

FIG. 2A provides a schematic of an exemplary feedback-type loop established by a modified gene (e.g., modified by delivery of one or more expression cassettes, such as any described herein) having a phenolic-inducible synthetic promoter $P_1$ 225 operably linked to a gene $G_1$ 226. The synthetic promoter is induced by the presence of a first phenolic compound 211, and expression of gene $G_1$ provides a first protein 231, which converts a first substrate 210 into a further first phenolic compound 212. Presence of further first phenolic compounds can further stimulate expression of the first protein.

In another non-limiting instance, a first phenolic compound that induces expression can result in expression of a first protein, which interacts with the first phenolic compound to produce a second phenolic compound. In this instance, a feedforward-type loop can be established, in which presence of the first phenolic compound induces an in situ biological network to produce a second phenolic compound that propagates intracellular degradation of the first phenolic compound. For example, a feedforward-type loop can be established by having a vanillin-inducible synthetic promoter operable linked to a nucleic acid encoding a LigV gene. Then, the presence of vanillin would promote expression of the LigV protein, which in turn will increase cellular concentrations of LigV to convert vanillin into vanillate, thus promoting conversion of vanillin into other phenolic degradation products.

A dynamic regulator system can include use of two or more expression cassettes, in which gene products from such cassettes can interact in parallel or consecutive reactions. In one non-limiting instance, cascading reaction networks can be implemented. For instance and without limitation, a first expression cassette can be inducible by a first phenolic compound, and a second expression cassette can be inducible by a second phenolic compound. Expression of the first gene (provided within the first expression cassette) can provide a first protein, which in turn provides the second phenolic compound. For example, a cascading network can be established by having a vanillin-inducible synthetic promoter operable linked to a nucleic acid encoding a LigV gene (provided by a first expression cassette) and a vanillate-inducible synthetic promoter operable linked to a nucleic acid encoding a VanA gene (provided by a second expression cassette). Then, the presence of vanillin would promote expression of the LigV protein, which in turn will increase cellular concentrations of LigV to convert vanillin into vanillate. Next, produced vanillate could promote expression of the VanA protein, which in turn can convert vanillate into PCA. In this manner, interacting reactions can be controlled by providing designed expression cassettes to a host cell.

Figure 2B:
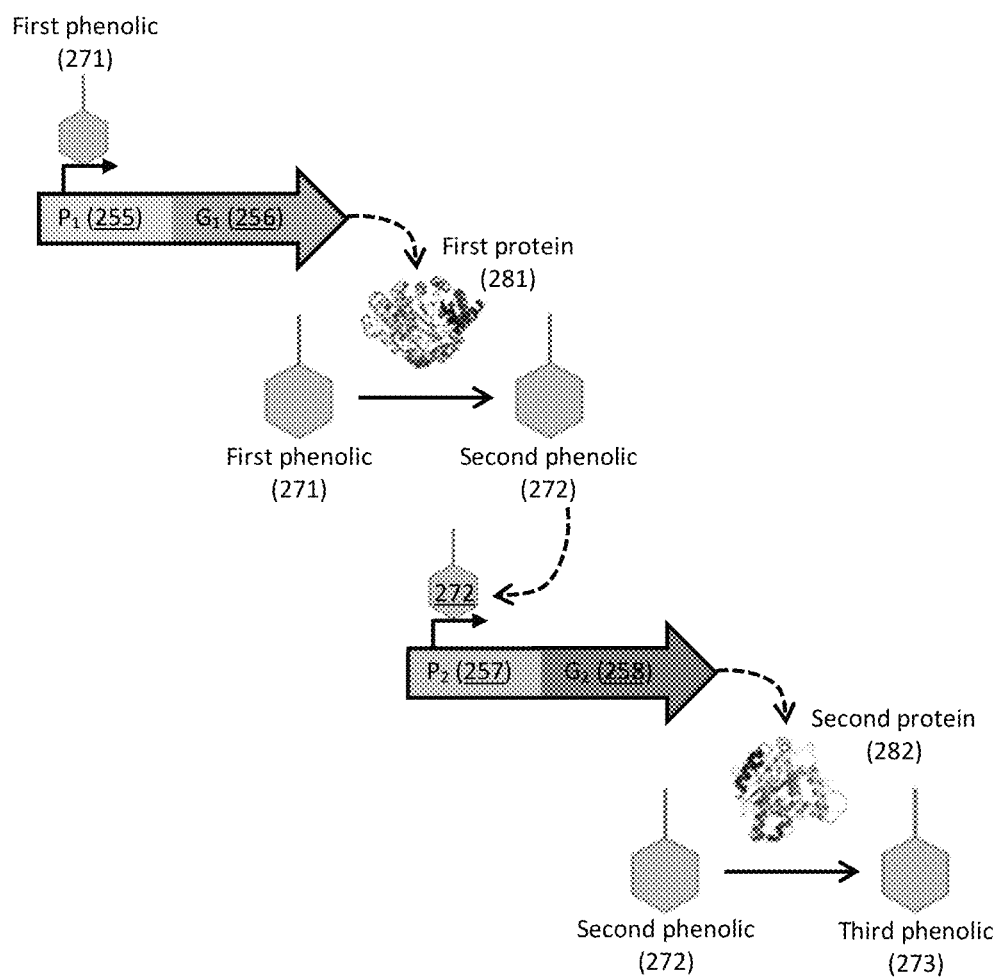

FIG. 2B provides a schematic of an exemplary cascading reaction network established by a plurality of modified genes (e.g., modified by delivery of one or more expression cassettes, such as any described herein). As can be seen, the modified genome can include a first phenolic-inducible synthetic promoter $P_1$ 255 operably linked to a first gene $G_1$ 256, as well as a second phenolic-inducible synthetic promoter $P_2$ 257 operably linked to a second gene $G_2$ 258.

The first synthetic promoter $P_1$ 255 is induced by the presence of a first phenolic compound 271, and expression of gene $G_1$ 256 provides a first protein 281, which converts a first phenolic compound 271 into a second phenolic compound 272. Then, the second synthetic promoter $P_2$ 257 is induced by the presence of the second phenolic compound 272, and expression of gene $G_2$ 258 provides a second protein 282, which converts a second phenolic compound 272 into a third phenolic compound 273.

Figure 2C:
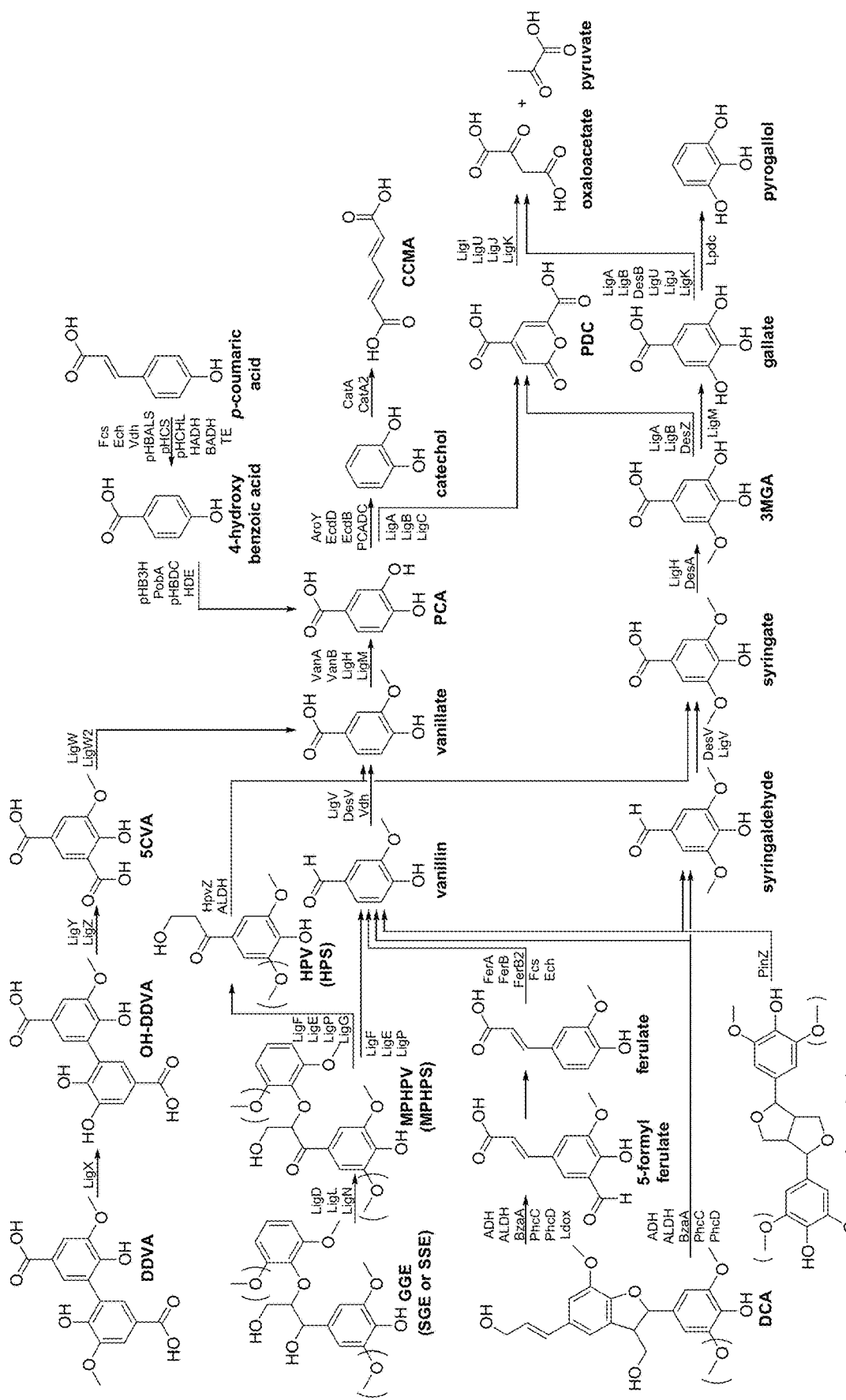

As can be seen, the synthetic promoter can be induced by any useful phenolic compound and be operably linked by any useful gene to express any useful protein (e.g., for degradation or conversion of a phenolic compound, lignin, or a lignin derivative). FIG. 2C shows exemplary phenolic compounds (chemical structures) and proteins useful degrading or converting phenolic compounds. Exemplary phenolic compounds include DDVA, OH-DDVA, 5CVA, GGE, SGE, SSE, MPHPV, MPHPS, HPV, HPS, 4-hydroxybenzoic acid, p-coumaric acid, DCA, 5-formyl ferulate, ferulate, pinoresinol, vanillin, vanillate, syringaldehyde, syringate, 3MGA, gallate, pyrogallol, PCA, catechol, or PDC.

A host cell can modified to include genes capable of expression one or more proteins (e.g., proteins in FIG. 2C) and in include promoters capable of being induced by one or more phenolic compound (e.g., compounds in FIG. 2C). Furthermore, modified regulatory systems can be established in a host cell to express of two or more proteins in a reaction sequence provided in FIG. 2C (e.g., in which a reaction is indicated by a substrate converted into a product by the presence of a protein, and a reaction sequence can include two or more reactions in which reactions are immediately upstream or downstream of each other).

In one non-limiting embodiment, the expression cassette includes a first synthetic promoter inducible by a first phenolic compound and a first gene operable linked to the first promoter that is configured to express a first protein. Exemplary constructs can include any of the following: a vanillin-inducible promoter upstream of a gene encoding LigV, DesV, Vdh, LigF, LigE, LigP, LigG, FerA, FerB, FerB2, Fcs, Ech, ADH, ALDH, BzaA, PhcC, PhcD, and/or PinZ, as well as any other protein described herein (e.g., in FIG. 2C); a vanillin-inducible promoter upstream of a gene encoding LigV, DesV, Vdh, VanA, VanB, LigH, LigM, LigA, LigB, and/or LigC, as well as any other protein described herein; a vanillate-inducible promoter upstream of a gene encoding LigV, DesV, Vdh, LigW, LigW2, HpvZ, ALDH, VanA, VanB, LigH, and/or LigM, as well as any other protein described herein (e.g., in FIG. 2C); a coumaric acid-inducible promoter upstream of a gene encoding Fcs, Ech, Vdh, pHBALS, pHCS, pHCHL, HADH, BADH, TE, pHB3H, PobA, pHBDC, and/or HDE, as well as any other protein described herein (e.g., in FIG. 2C); a syringaldehyde-inducible promoter upstream of a gene encoding ADH, ALDH, BzaA, PhcC, PhcD, and/or PinZ, as well as any other protein described herein (e.g., in FIG. 2C); a syringaldehyde-inducible promoter upstream of a gene encoding LigV, DesV, Vdh, LigH, DesA, DesZ, LigM, LigA, LigB, and/or LigC, as well as any other protein described herein; a syringate-inducible promoter upstream of a gene encoding DesV, LigV, HpvZ, ALDH, LigH, and/or DesA, as well as any other protein described herein (e.g., in FIG. 2C); a PCA-inducible promoter upstream of a gene encoding VanA, VanB, LigH, LigM, AroY, EcdD, EcdB, PCADC, LigA, LigB, LigC, pHB3H, PobA, pHBDC, and/or HDE, as well as any other protein described herein (e.g., in FIG. 2C); and a 3MGA-inducible promoter upstream of a gene encoding LigH, DesA, LigA, LigB, DesZ, and/or LigM, as well as any other protein described herein (e.g., in FIG. 2C).

In another non-limiting embodiment, the expression cassette includes a first synthetic promoter inducible by a first phenolic compound and a first gene operable linked to the promoter that is configured to express a first protein, as well as a second synthetic promoter inducible by a second phenolic compound and a second gene operable linked to the promoter that is configured to express a second protein. The first and second phenolic compounds can be the same or different.

A recombinant gene can include any useful synthetic promoter (e.g., any described herein) that is upstream of a gene. Expression cassettes (e.g., any described herein) can be provided in any useful vector. Furthermore, a host cell can include a modified gene that include any useful synthetic promoter (e.g., any described herein), which can be provided in any useful manner (e.g., an expression cassette, a vector, etc.).

Phenolic Compounds

The present invention relates, in part, to a synthetic promoter capable of being induced by the presence of one or more phenolic compounds. Induction can be characterized by enhanced transcription of a gene operably linked to the promoter in the presence of a phenolic compound, as compared to transcription in the absence of the phenolic compound.

Exemplary phenolic compounds include one or more lignin-derived aromatics (e.g., one or more degradation products of lignin). Non-limiting phenolic compounds include monoaryl compounds (e.g., vanillin; vanillate or vanillic acid, as well as salts thereof and deprotonated forms thereof, ferulate or ferulic acid, as well as salts thereof and deprotonated forms thereof; coumarate or coumaric acid (e.g., p-coumaric acid), as well as salts thereof and deprotonated forms thereof; syringaldehyde; syringate or syringic acid, as well as salts thereof and deprotonated forms thereof, vanilloyl acetaldehyde (VAL); vanilloyl acetic acid; 5-carboxyvanillate (5CVA); or protocatechuate (PCA).

Figure 1C:
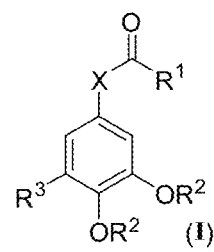

Further exemplary phenolic compounds include those having a structure of formula (I) (FIG. 1C) or a salt thereof or an anionic form thereof, in which X is a bond (e.g., a covalent bond), an optionally substituted alkylene, an optionally substituted alkenylene, or an optionally substituted heteroalkylene; $R_1$ is H, optionally substituted alkyl, optionally substituted alkoxy, optionally substituted alkanoyl, carboxyaldehyde, carboxyaldehydealkyl, hydroxyl, hydroxyalkyl, thiol, thioalkoxy, carboxyalkyl, or a protecting group; each of $R^2$ is, independently, H or optionally substituted alkyl; and $R^3$ is H, optionally substituted alkyl, optionally substituted alkoxy, optionally substituted alkanoyl, or hydroxyl.

Genes and Gene Products, Including Proteins

The present invention relates, in part, to a novel promoter that can be operably linked to a gene (e.g., a heterologous gene). In particular embodiments, the gene is a protein (e.g., involved in the catabolism or synthesis of one or more phenolic compounds, such as any described herein).

Exemplary genes and proteins include one or more of the following: ADH (e.g., an alcohol dehydrogenase), ALDH (e.g., an aldehyde dehydrogenase), AroY (e.g., a protocatechuate decarboxylase, such as in GenBank Acc. Nos. KX774258, ADF61496, and BAH20873), BADH (e.g., a benzaldehyde dehydrogenase), BzaA (e.g., a benzaldehyde-derivatives dehydrogenase, such as in GenBank Acc. No. BAK67466), CatA (e.g., a catechol dioxygenase, such as in GenBank Acc. No. BAA07037, D37782, or GAM30370), CatA2 (e.g., a catechol 1,2-dioxygenase, such as in GenBank Acc. No. D37782), CouP (e.g., a coumarate transporter, such as in GenBank Acc. No. 4JB2_A or in GenBank Acc. No. CAE27230), DesA (e.g., a syringate O-demethylase, such as in GenBank Acc. No. BAK67175), DesB (e.g., a gallate dioxygenase, such as in GenBank Acc. No. BAK65008), DesV (e.g., a dehydrogenase or a benzaldehyde dehydrogenase, such as in GenBank Acc. No. BAK67507), DesZ (e.g., a 3-O-methylgallate 3,4-dioxygenase, such as in GenBank Acc. No. BAK66578), EcdB (e.g., a decarboxylase subunit, such as in GenBank Acc. No. ADF63617), EcdD (e.g., a decarboxylase subunit, such as in GenBank Acc. No. ADF63615), Ech (e.g., enoyl-CoA-hydratase or p-hydroxycinnamoyl-CoA hydratase/lyase, such as in GenBank Acc. No. Y13067 and in Gene ID Nos. 1046422 and 1047000), Fcs (e.g., a feruloyl-CoA synthetase, such as in GenBank Acc. Nos. AJ238746 or NP_745496.2 and in Gene ID No. 1046999), FerA (e.g., a feruloyl-CoA synthetase, such as in GenBank Acc. No. BAK67177), FerB (e.g., a feruloyl-CoA hydratase/lyase, such as in GenBank Acc. No. BAK67178), FerB2 (e.g., a feruloyl-CoA hydratase/lyase, such as in GenBank Acc. No. BAK65462), FerC (e.g., such as in GenBank Acc. No. BAK67179), FDC (e.g., a ferulic acid decarboxylase, such as FDC1 or in GenBank Acc. No. BK006938), HADH (3-hydroxyacyl-CoA dehydrogenase), HDE (e.g., a hydroxylase), HpvZ (e.g., a choline dehydrogenase or a β-hydroxypropiovanillone (HPV) oxidase, such as exemplary amino acid sequences provided as UniProt Acc. Nos. G2IQT6, G2IPY4, G2INY6, and G2INY7, as well as exemplary nucleic acid sequences provided as Ensembl Gene ID Nos. SLG 09500, SLG_09510, and SLG_12830), LigA (e.g., a protocatechuate 4,5-dioxygenase, such as in DDBJ Acc. No. M34835-1 or in GenBank Acc. No. BAK65926), LigB (e.g., a protocatechuate 4,5-dioxygenase, such as in DDBJ Acc. No. M34835-2 or in GenBank Acc. No. BAK65925), LigC (e.g., a 4-carboxy-2-hydroxymuconate-6-semialdehyde (CHMS) dehydrogenase, such as in GenBank Acc. No. BAK65924), LigD (e.g., a C-α-dehydrogenase, such as in DDBJ Acc. No. D11473-1 and in GenBank Acc. No. BAK65539), LigE (e.g., a β-etherase or a glutathione S-transferase (GSTase), such as in DDBJ Acc. No. M11473-3 and in GenBank Acc. No. BAK65541), LigF (e.g., a β-etherase or a GSTase, such as in DDBJ Acc. No. D11473-2 and in GenBank Acc. No. BAK65540), LigG (e.g., a glutathione lyase or a GSTase, such as in DDBJ Acc. No. AB026292 and in GenBank Acc. No. BAK65542; UniProt Acc. Nos. Q9WXJ9, G2IN94, and A0A158S6W2; or Ensembl Gene ID Nos. SPHV1_50078 and SPHV1_50078), LigDFG, LigH (e.g., a 10-formyltetrahydrofolate synthetase, such as in DDBJ Acc. No. AB006079-1 or in GenBank Acc. No. BAK65951), LigI (e.g., a 2-pyrone-4,6-dicarboxylate (PDC) hydrolase, such as in DDBJ Acc. No. AB015964 or in GenBank Acc. No. BAK65932), LigJ (e.g., an 4-oxalomesaconate (OMA) hydratase, such as in GenBank Acc. No. BAK65927), LigK (e.g., a 4-carboxy-4-hydroxy-2-oxoadipate (CHA) aldolase, such as in GenBank Acc. No. BAK65930), LigL (e.g., a C-α-dehydrogenase, such as in GenBank Acc. No. BAK68041), LigM (e.g., a 3-O-methylgallate-O-demethylase, such as in GenBank Acc. No. KX774255 or in GenBank Acc. Nos. BAK65949 or BAK65949.1), LigN (e.g., a C-α-dehydrogenase, such as in GenBank Acc. No. BAK68265), LigO (e.g., a C-α-dehydrogenase, such as in GenBank Acc. No. BAK68263), LigP (e.g., a β-etherase, such as in GenBank Acc. No. BAK67935), LigR (e.g., such as in GenBank Acc. No. BAK65929), LigU (e.g., a tautomerase or an OMA tautomerase, such as in GenBank Acc. No. BAK65931), LigV (e.g., a vanillin dehydrogenase, such as in GenBank Acc. Nos. KX774254, BAK65381, or BAK65381.1), LigW (e.g., a decarboxylase or a 5-carboxyvanillate decarboxylase, such as in GenBank Acc. No. BAK65460), LigW2 (e.g., a decarboxylase or a 5-carboxyvanillate decarboxylase, such as in GenBank Acc. No. BAK65956), LigX (e.g., a 5,5'-dehydrodivanillate (DDVA) O-demethylase component, such as in GenBank Acc. Nos. BAK65452, BAK65525, or BAK66795; including LigXa, LigXb, LigXc, and/or LigXd), LigY (e.g., a hydrolase or a 2,2', 3-trihydroxy-3'-methoxy-5,5'-dicarboxybiphenyl (OH-DDVA) meta-cleavage compound hydrolase, such as in DDBJ Acc. No. AB018415 and in GenBank Acc. No. BAK65450), LigZ (e.g., a dioxygenase and a OH-DDVA dioxygenase, such as in DDBJ Acc. No. AB007823-1 and in GenBank Acc. No. BAK65447), Lpdc (e.g., a gallate decarboxylase or 3-octaprenyl-4-hydroxybenzoate carboxy-lyase, such as in GenBank Acc. No. NC_004567.2 or Gene ID No. 1063372, locus tag Lp_2945), LsdA (e.g., a lignostilbene dioxygenase, such as in DDBJ Acc. No. AB015964), MetF (e.g., a methylene folate reductase, such as in GenBank Acc. No. BAK65950), PCADC (e.g., a protocatechuate decarboxylase), pHB3H (e.g., a p-hydroxybenzoate-3-hydroxylase), pHBALS (e.g., a p-hydroxybenzaldehyde synthase), pHBDC (e.g., a p-hydroxybenzoate decarboxylase), PhcC (e.g., a (+)-DCA-C oxidase, such as in GenBank Acc. No. BAK65623), PhcD (e.g., a (−)-DCA-C oxidase, such as in GenBank Acc. No. BAK65625), pHCHL (e.g., a p-hydroxycinnamoyl-CoA hydratase/lyase), pHCS (e.g., a p-hydroxycinnamoyl-CoA synthetase), PinZ (e.g., a pinoresinol/lariciresinol reductase, such as in GenBank Acc. No. BAK65407), PobA (e.g., a p-hydroxybenzoate hydroxylase, such as in GenBank Acc. No. X68438), TE (e.g., a thiolase), VanA (e.g., a vanillate-O-demethylase oxygenase subunit, such as in GenBank Acc. No. Y14759), VanB (e.g., a vanillate-O-demethylase reductase subunit, such as in GenBank Acc. No. Y14759), and Vdh (e.g., a vanillin dehydrogenase, such as in GenBank Acc. No. Y11520 and Gene ID No. 1047002).

In particular embodiments, the gene encodes for one or more of LigV, DesV, HpvZ, LigF, LigE, LigP, LigD, LigDFG, LigL, LigN, LigG, LigY, LigW, LigW2, LigM, DesA, LigA, LigB, LigC, LigX, LigZ, DesZ, FerA, FerB, FerB2, AroY, CatA, CouP, pHCS, Ech, FDC, HADH, or Lpdc. In other embodiments, the protein is selected from the group of LigV, DesV, HpvZ, LigF, LigE, LigP, LigD, LigDFG, LigL, LigN, LigG, LigY, LigW, LigW2, LigM, DesA, LigA, LigB, LigC, LigX, LigZ, DesZ, FerA, FerB, FerB2, AroY, CatA, CouP, pHCS, Ech, FDC, HADH, and Lpdc.

Further exemplary genes and proteins include one or more C-α-dehydrogenases (e.g., LigD, LigL, LigN, and LigO), such as exemplary amino acid sequences provided as UniProt Acc. Nos. Q01198, G0EUA3, G8Q248, A0A2W7NR13, C0SUJ9, C0SUK1, and C0SUK3, as well as exemplary nucleic acid sequences provided as Ensembl Gene ID Nos. ACIDI_44c00110, CNE_1c15670, GOACH_04_03020, SLG_08640, SLG_33660, SLG_35880, SLG_35900, and SPHV1_50071); one or more β-etherases (e.g., LigF, LigE, and LigP, such as exemplary amino acid sequences provided as UniProt Acc. Nos. P30347, P27457, G21N92, A0A2K8MHZ7, G21N93, A0A0M3FT69, and E1CJ68, as well as exemplary nucleic acid sequences provided as Ensembl Gene ID Nos. A8U91_02108, ACIDI_4c01430, BGL_2c14680, JAB1_29170, LOKO_01842, PsAD26_02197, PsWM33_05031, PsW74_02125, SHLA_51c000130, SE99_00257, SLG_08650, SLG_08660, SLG_32600, SPHV1_50077, and USDA257_c08850); one or more aromatic transporters (e.g., CouP or VanK, such as in GenBank Acc. Nos. AF009672, 4JB2_A, or CAE27230); one or more vanillin dehydrogenases (e.g., LigV or Vdh, such as in GenBank Acc. Nos. KX774254, BAK65381, BAK65381.1, or Y11520); and one or more feruloyl-CoA synthetases (e.g., FerA or Fcs, such as in GenBank Acc. Nos. BAK67177 or AJ238746).

Further exemplary genes and proteins include one or more of the following: an alcohol dehydrogenase, an aldehyde dehydrogenase, a benzaldehyde dehydrogenase (e.g., DesV), a benzaldehyde-derivative dehydrogenase (e.g., BzaA), a C-α-dehydrogenase (e.g., LigD, LigL, LigN, or LigO), a 4-carboxy-2-hydroxymuconate-6-semialdehyde (CHMS) dehydrogenase (e.g., LigC), a 4-carboxy-4-hydroxy-2-oxoadipate (CHA) aldolase (e.g., LigK), a catechol dioxygenase (e.g., CatA or CatA2), a choline dehydrogenase (e.g., a DCA-C oxidase and including HpvZ, PhcC, or PhcD), a coumarate transporter (e.g., CouP or VanK), a decarboxylase subunit (e.g., EcdB or EcdD), an enoyl-CoA-hydratase (e.g., a p-hydroxycinnamoyl-CoA hydratase/lyase), a β-etherase (e.g., LigE, LigF, or LigP), a ferulic acid decarboxylase (e.g., FDC1), a ferulic acid responsive repressor (e.g., FerC), a feruloyl-CoA synthetase (e.g., FerA or Fcs), a feruloyl-CoA hydratase/lyase (e.g., FerB or FerB2), a 10-formyltetrahydrofolate synthetase (e.g., LigH), a gallate demethylase (e.g., a 3-O-methylgallate-O-demethylase and including LigM), a gallate decarboxylase (e.g., a 3-octaprenyl-4-hydroxybenzoate carboxy-lyase and including Lpdc), a gallate dioxygenase (e.g., a 3-O-methylgallate 3,4-dioxygenase and including DesB or DesZ), a glutathione lyase (e.g., LigG), a glutathione S-transferase (GSTase) (e.g., LigE, LigF, or LigG), a 3-hydroxyacyl-CoA dehydrogenase, a hydroxylase, a p-hydroxypropiovanillone oxidase, a lignostilbene dioxygenase (e.g., LsdA), a LysR-type transcriptional regulator (LTTR) (e.g., LigR), a methylene folate reductase (e.g., MetF), an 4-oxalomesaconate (OMA) hydratase (e.g., LigJ), an OMA tautomerase (e.g., LigU), a p-hydroxybenzoate decarboxylase, a p-hydroxybenzoate hydroxylase (e.g., PobA), a p-hydroxybenzaldehyde synthase, a p-hydroxycinnamoyl-CoA hydratase/lyase, a p-hydroxycinnamoyl-CoA synthetase, a phthalate dioxygenase (e.g., a 5,5'-dehydrodivanillate (DDVA) O-demethylase component or a OH-DDVA dioxygenase; and including LigX, LigXa, LigXb, LigXc, LigXd, or LigZ), a phthalate hydrolase (e.g., a 2,2',3-trihydroxy-3'-methoxy-5,5'-dicarboxybiphenyl (OH-DDVA) meta-cleavage compound hydrolase and including LigY), a pinoresinol/lariciresinol reductase (e.g., PinZ), a protocatechuate decarboxylase (e.g., AroY), a protocatechuate dioxygenase (e.g., a protocatechuate 4,5-dioxygenase and including LigA and LigB), a 2-pyrone-4,6-dicarboxylate (PDC) hydrolase (e.g., LigI), a syringate O-demethylase (e.g., DesA), a thiolase, a vanillate decarboxylase (e.g., a 5-carboxyvanillate decarboxylase and including LigW and LigW2), a vanillin dehydrogenase (e.g., LigV or Vdh), and a vanillate demethylase oxygenase (e.g., a vanillate-O-demethylase oxygenase subunit and including VanA and VanB).

Each accession number (Acc. No.) and identification number (ID No.) recited herein, as well as associated sequences, is incorporated herein by reference in its entirety Such genes and proteins can be from any useful organism, including and not limited to any of the following: *Sphingomonas* (e.g., *S. paucimobilis*), *Sphingobium* (e.g., *Sphingobium* sp. SYK-6 or Cra20), *Pseudomonas* (e.g., *P. paucimobilis* or *P. fluorescens*), *Novosphingobium* (e.g., *Novosphingobium* sp. AAP83 or *Novosphingobium* sp. KN65.2), *Acidiphilium* (e.g., *Acidiphilium* sp. JA12-A), *Cupriavidus* spp. (e.g., *C. necator*), *Gordonia* (e.g., *Gordonia aichiensis* NBRC 108223), etc.), *Acinetobacter* (e.g., *A. baumannii*), *Burkholderia* (e.g., *Burkholderia glumae* PGI), *Ceratocystis* (e.g., *C. fimbriata* CBS 114723), *Halomonas* (e.g., *H. chromatireducens* or *H. elongata*), *Pseudovibrio* (e.g., *Pseudovibrio* sp. Ad26, *Pseudovibrio* sp. W74, or *Pseudovibrio* sp. WM33), *Pseudomonas* (e.g., *P. putida*), *Sinorhizobium* (e.g., *S. fredii* USDA 257), *Bradyrhizobium* (e.g., *B. diazoefficiens*), *Corynebacterium* (e.g. *C. glutamicum*), *Rhodopseudomonas* (e.g., *R. palustris*), etc.

Exogenous Nucleic Acids and Proteins

Hosts can be engineered to include an exogenous nucleic acid (e.g., any described herein), in which expression of such an exogenous nucleic acid produces exogenous proteins (e.g., any described herein). The term "heterologous" or "exogenous" as used herein with reference to nucleic acids and amino acids (e.g., enzymes), indicates nucleic acids and amino acids that are expressed in an organism other than the organism from which they originated or are found in nature, independently on the level of expression that can be lower, equal to, or higher than the level of expression of the molecule in the native microorganism. An exogenous nucleic acid may be from a different species (and so heterologous) or from the same species (and so homologous), relative to the cell being transformed. Thus, an exogenous nucleic acid (e.g., a gene) can include a homologous nucleic acid that occupies a different location in the genome of the cell or is under different control, relative to the endogenous copy of the nucleic acid. An exogenous nucleic acid may be present in more than one copy in the cell. An exogenous nucleic acid may be maintained in a cell as an insertion into the genome (nuclear or plastid) or as an episomal molecule.

In some embodiments, the exogenous nucleic acid is a nucleic acid that has been generated via human intervention, including by recombinant means or direct chemical synthesis, with a series of specified nucleic acid elements that permit transcription and/or translation of a particular nucleic acid in a host cell. The exogenous nucleic acid (e.g., an expression vector or an expression cassette) may be part of a plasmid, virus, or nucleic acid fragment. One of skill in the art understands that a "recombinant nucleic acid" that encodes a particular gene, or portion thereof, is isolated from the specific context in which it naturally occurs.

In particular embodiments, the exogenous nucleic acid includes one or more coding sequences (e.g., a nucleic acid to be transcribed) that is in operable linkage with a promoter (e.g., any described herein). In other embodiments, the coding sequence is in operable linkage with a control element (e.g., one or more promoters, enhancers, transcription termination sequences, and translation initiation sequences). In some embodiments, the exogenous nucleic acid includes a coding sequence and a promoter (e.g., any described herein, such as a phenolic-inducible synthetic promoter), optionally in combination with one or more control sequences. Expression cassettes for enzymes include, for example and without limitation, a translation initiation control sequence. An exogenous nucleic acid may be present or provided as a vector.

Promoters can include any useful combinations of regions or elements (e.g., any described herein). Further elements include, e.g., in the case of a polymerase II type promoter, a TATA element. A promoter also optionally includes distal enhancer or repressor elements, which may be located as much as several thousand base pairs from the start site of transcription. Non-limiting promoters can include a nucleic acid sequence having at least 80% sequence identity to any one of SEQ ID NOs:1-9 or a fragment thereof.

Sources

Exemplary sources include any including a phenolic compound (e.g., any described herein), lignin, or a lignin derivative (e.g., formed from a combination of one or more monomers, such as a monolignol monomer, a p-coumaryl alcohol or an alkoxyl form thereof (e.g., a methoxylated form), a coniferyl alcohol or an alkoxyl form thereof (e.g., a methoxylated form), and a sinapyl alcohol or an alkoxyl form thereof (e.g., a methoxylated form). In other embodiments, lignin or a lignin derivative can be characterized by the presence of one or more aromatic functional groups, such as a p-hydroxyphenyl group, a guaiacyl group, and/or a syringyl group.

Lignin can have different compositions depending on the plant material from which the lignin is derived. Exemplary lignin can include softwood lignin (e.g., derived from softwood and including of from about 25% to about 30% (w/w) of lignin), compression wood lignin (e.g., derived from compression wood and including of from about 35% to about 40% (w/w) of lignin), typical hardwood lignin (e.g., derived from hardwood and including of from about 20% to about 25% (w/w) of lignin), tropical hardwood lignin (e.g., derived from tropical hardwood and including of from about 30% to about 40% (w/w) of lignin), tension wood lignin (e.g., derived from tension wood and including of from about 20% to about 25% (w/w) of lignin), wheat lignin (e.g., derived from wheat, including any useful part of plant, such as the root, leaves, shoots, and/or stems), maize lignin (e.g., derived from maize, including any useful part of plant, such as the root, leaves, shoots, and/or stems; and including of from about 20% to 75% (w/w) of lignin), mixed grasses lignin (e.g., derived from mixed grasses, including any useful part of plant, such as the root, leaves, shoots, and/or stems).

The source can include any useful material, such as, e.g., various monosaccharides (e.g., dextrose, fructose, galactose, glucose, maltose, xylose, etc.), oligosaccharides, polysaccharides (e.g., cellulose, hemicellulose, starch, etc.), cellulosic material, fatty acids (e.g., saturated or unsaturated fatty acids), biomass hydrolysates, metabolic intermediates (e.g., acetate, lactate, succinate, etc.), alcohols and sugar alcohols (e.g., ethanol, ethylene glycol, glycerol, inositol, malitol, mannitol, sorbitol, or xylitol), lignin and lignin compounds (e.g., lignocellulose and lignocellulosic material), plants and plant products (e.g., corn, liquefied corn meal, corn steep liquor (a byproduct of corn wet milling process that contains nutrients leached out of corn during soaking), corn stover, corn fiber, rice straw, woody plants, herbaceous plants, molasses, etc., which can be found in, for example, in the stems, leaves, hulls, husks, and cobs of plants; or in the leaves, branches, and wood of trees), herbaceous material, agricultural residues, forestry residues, municipal solid wastes, waste paper, as well as pulp and paper mill residues, or mixtures thereof.

EXAMPLES

Example 1: Novel Promoter Engineering Technique to Increase Protein Expression Lignin valorization is viewed as a key for the development of a cost effective lignocellulosic biorefinery. Employing promoters inducible by phenolics can provide numerous advantages, including (1) the development of substrate-inducible systems, in which selected substrates within a reaction can further enhance protein expression; (2) the lower operating costs by replacing expensive inducers (e.g., isopropyl β-D-1-thiogalactopyranoside (IPTG) currently used for induction) with in situ inducers that are present or produced during lignin breakdown; (3) the development of dynamic regulatory systems; and (4) increased flexibility in operating conditions.

As described herein, hybrid synthetic promoters were constructed by replacing the spacer region of an endogenous promoter (e.g., $P_{emrR}$) with an exogenous nucleic acid sequence. The strength of the promoters was interrogated using a fluorescent reporter. In the presence of an exemplary phenolic compound (e.g., vanillin), the strains with the engineered promoters showed increased expression of the fluorescence reporter, as compared to a strain with the native promoter. Flow cytometry was employed to identify heterogeneity if present in the cell population after induction with phenolic compounds. In particular experiments, we observed the emergence of a sub-population constituting healthy and dividing cells in cultures induced with an exemplary phenolic compound (vanillin) at mM concentration levels (e.g., of from about 0.1 mM to about 100 mM). In particular experiments, the size of this sub-population remained the same, regardless of the promoter employed; and further analysis uncovered that this smaller sub-population of cells were primarily responsible for the increased expression that was observed with the engineered promoters. In part, the study also revealed that to achieve higher density of heterologous protein expression, efforts may include both approaches of increasing the expression level of genes and also maintaining a healthy cell population in the presence of phenolic compounds. Additional details are provided herein.

Example 2: Hybrid Phenolic-Inducible Promoters Towards Construction of Self-Inducible Systems for Microbial Lignin Valorization Background: Engineering strategies to create promoters that are both higher strength and tunable in the presence of inexpensive compounds are of high importance to develop metabolic engineering technologies that can be commercialized. Lignocellulosic biomass stands out as the most abundant renewable feedstock for the production of biofuels and chemicals. However, lignin a major polymeric component of the biomass is made up of aromatic units and remains as an untapped resource. Novel synthetic biology tools for the expression of heterologous proteins are one critical component for the effective engineering of a microbe to valorize lignin. To our knowledge, this study demonstrates the first successful attempt in the creation of engineered promoters that can be induced by aromatics present in lignocellulosic hydrolysates to increase heterologous protein production.

Results: A hybrid promoter engineering approach was used for the construction of phenolic-inducible promoters of higher strength. The exemplary hybrid promoters were constructed by replacing the spacer region of an endogenous promoter $P_{emrR}$ present in E. coli that was naturally inducible by phenolics. In the presence of vanillin, the engineered promoters $P_{vtac}$, $P_{vtrc}$, and $P_{vtic}$ increased protein expression by 4.6-, 3.0-, and 1.5-fold, respectively, in comparison with a native promoter, $P_{emrR}$. In the presence of vanillic acid, $P_{vtac}$, $P_{vtrc}$, and $P_{vtic}$ improved protein expression by 9.5-, 6.8-, and 2.1-fold, respectively, in comparison with $P_{emrR}$. Among the cells induced with vanillin, the emergence of a sub-population constituting the healthy and dividing cells using flow cytometry was observed. The analysis also revealed this smaller sub-population to be the primary contributor for the increased expression that was observed with the engineered promoters.

Conclusions: This study demonstrates the first successful attempt in the creation of engineered promoters that can be induced by aromatics to increase heterologous protein production. Employing promoters inducible by phenolics can provide the following exemplary advantages: (1) develop substrate inducible systems; (2) lower operating costs by replacing expensive IPTG currently used for induction; (3) develop dynamic regulatory systems; and (4) provide flexibility in operating conditions. The flow cytometry findings strongly suggest the need for novel approaches to maintain a healthy cell population in the presence of phenolics to achieve increased heterologous protein expression and, thereby, valorize lignin efficiently. Additional details follow.

Example 3: Exemplary Experimental Methods

Materials: Restriction enzymes, T4 DNA ligase, and plasmid miniprep kit were purchased from Thermo Fisher Scientific (Waltham, Mass.). Gel purification kit and Q5 polymerase were purchased from Promega (Madison, Wis.) and New England Biolabs (Ipswich, Mass.), respectively. All the reagents and cell culture media were purchased from Sigma-Aldrich (St. Louis, Mo.). Oligonucleotides were synthesized by Integrated DNA Technologies (Coralville, Iowa). The FluoSphere® beads used for calibration of the flow cytometer were purchased from Invitrogen (Carlsbad, Calif.). The E. coli strain carrying the plasmid pNW33N was purchased from the Bacillus Genetic Stock Center (Columbus, Ohio). E. coli Mach purchased from Invitrogen was used for all the cloning and fluorescence experiments.

Construction of plasmids and strains: The vector pNW33N containing a gene encoding for chloramphenicol resistance served as the backbone for all the plasmids constructed in this study. mCherry was PCR amplified from the plasmid pCtl-RFP-S$_{Arac}$ (see, e.g., Chou H H et al., "Programming adaptive control to evolve increased metabolite production," Nat. Commun. 2013; 4:2595 (8 pp.)). The promoters to be tested were incorporated in the forward primers (Table 1) that were employed for amplifying mCherry. Therefore, the DNA fragments obtained from this PCR amplification step had the promoters incorporated in the region upstream to the transcription initiation site of mCherry.

TABLE 1

Exemplary oligonucleotides

| Primer name | Sequence (5'→3') | SEQ ID NO: |
|---|---|---|
| Pr_f10a | gcgcggatccgaatcattrnctaa aacaatacatttactttatttgtc actgtcgttactatateggctgaa attaatgaggtcatacccaaataa ggaggatattatggtttccaaggg egaggag | 43 |

TABLE 1-continued

Exemplary oligonucleotides

| Primer name | Sequence (5'→3') | SEQ ID NO: |
|---|---|---|
| Pr_fl1a | gcgcggatccgaatcatifitcta aaacaatacatttgacaattaatc atcggctcgtataatgatcggctg aaattaatgaggtcatacccaaat aaggaggggaattcatggtttcca agggcgaggag | 44 |
| Pr_fl2a | gcgcggatccgaatcatifitcta aaacaatacatttgacaattaatc atccggctcgtataatgatcggct gaaattaatgaggtcatacccaaa taaggaggggaattcatggtttcc aagggcgaggag | 45 |
| Pr_fl3a | gcgcggatccgaatcattttcta aaacaatacatttgacaattaatc atcgcggctcgtataatgatcggc tgaaattaatgaggtcatacccaa ataaggaggggaattcatggttc caagggcgaggag | 46 |
| Pr_fl10b | cggctgaaattaatgaggtcatac ccaa | 47 |
| Pr_r1c | gcgcaagcttgcggccgcagagtt tgtagaaacgcaaaaaggcc | 48 |
| Pr_r1d | aagcttgcggccgcagagttt | 49 |
| Pr_f9 | gtcgatcggttcatcattcaccaaa | 50 |
| Pr_r2 | tgtgagttagctcactcattaggca | 51 |

The PCR obtained fragments were digested using the restriction enzymes BamHI and HindIII. The digested fragments were purified and ligated into the same restriction sites of pNW33N using T4 DNA ligase. The ligation products were transformed into *E. coli* Mach1 cells using electroporation.

Figure 3:
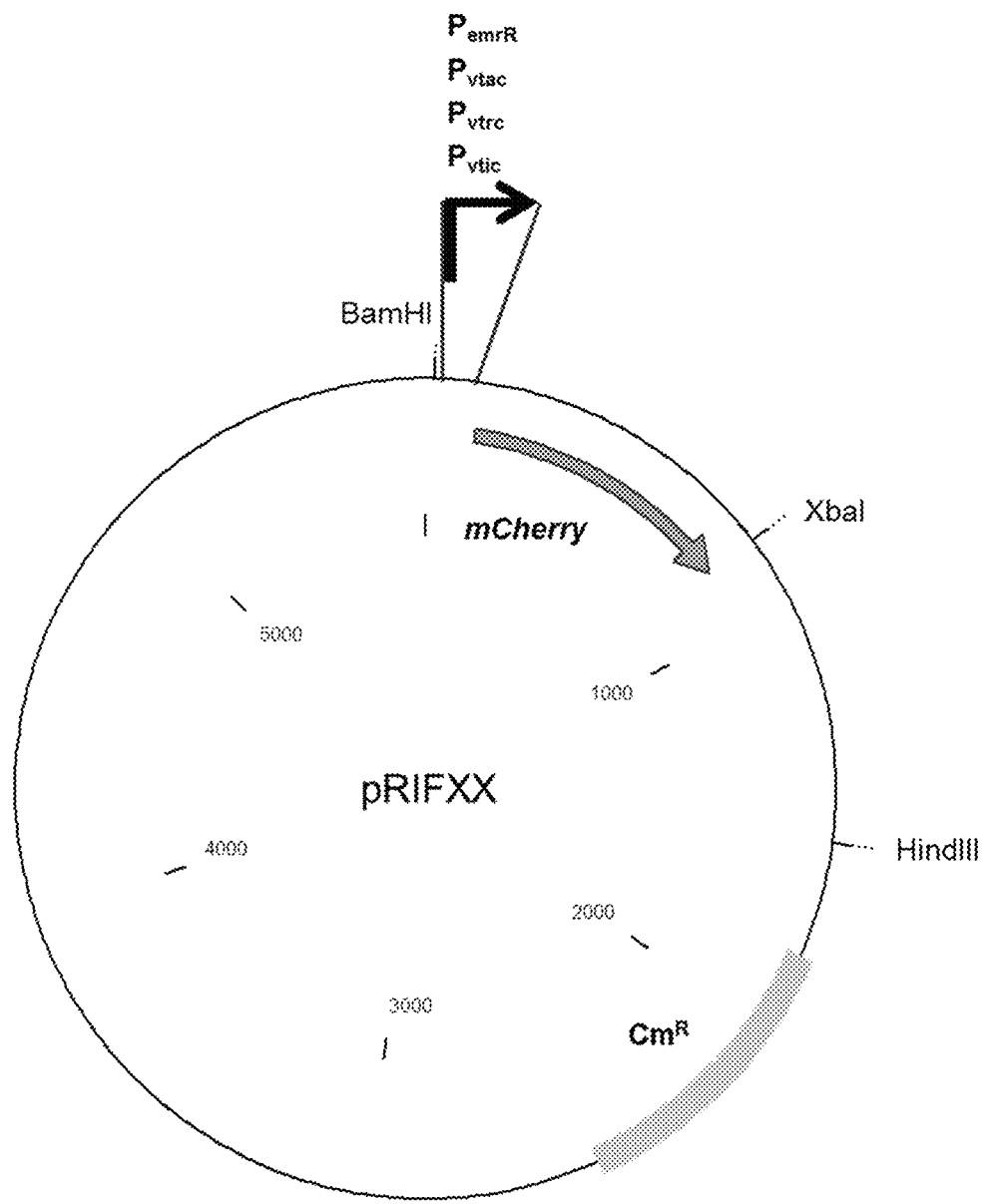
FIG. 3 shows a vector map of an exemplary construct used to interrogate the strength of the promoters described herein. Based upon the promoter present in the construct, pRIFXX can be pRIF01, pRIF02, pRIF03, or pRIF04.

The plasmids and strains constructed in this study to interrogate the strength of the promoters are listed in Table 2. Sequencing of the plasmid constructs was performed by Quintara Biosciences. A vector map of the plasmid constructed for interrogating the strength of the different engineered promoters is shown in FIG. 3.

TABLE 2

Plasmids and strains

| Plasmids/strains | Description | Source or reference |
|---|---|---|
| Plasmids | | |
| pNW33N | Backbone plasmid for all vectors constructed in this study | Bacillus Genetic Stock Center (BGSC) |
| pRIF01 | Derived from pNW33N with mCherry and the promoter, $P_{emrR}$ | Described herein |
| pRIF02 | Derived from pNW33N with mCherry and the promoter, $P_{vtac}$ | Described herein |
| pRIF03 | Derived from pNW33N with mCherry and the promoter, $P_{vtrc}$ | Described herein |
| pRIF04 | Derived from pNW33N with mCherry and the promoter, $P_{vtic}$ | Described herein |
| Strains | | |
| *E. coli* Mach1 | Host strain | Invitrogen |
| RIF00 | *E. coli* with pNW33N | BGSC |
| RIF01 | *E. coli* $P_{emrR}$::mCherry::Cm$^r$ | Described herein |
| RIF02 | *E. coli* $P_{vtac}$::mCherry::Cm$^r$ | Described herein |
| RIF03 | *E. coli* $P_{vtrc}$::mCherry::Cm$^r$ | Described herein |
| RIF04 | *E. coli* $P_{vtic}$::mCherry::Cm$^r$ | Described herein |

Sequences of the promoters are listed in Table 3.

TABLE 3

Exemplary nucleotide sequence of promoters

| Promoter name | Sequence (5'→3') | SEQ ID NO: |
|---|---|---|
| PemrR | gaatcattttctaaaacaataca tttactttatttgtcactgtcgtt actatatcggctgaaattaatgag gtcatacccaaat | 52 |
| Pvtac | gaatcattttctaaaacaataca tttgacaattaatcatcggctcgt ataatgatcggctgaaattaatga ggtcatacccaaat | 53 |
| Pvtrc | gaatcattttctaaaacaataca tttgacaattaatcatccggctcg tataatgatcggctgaaattaatg aggtcatacccaaat | 54 |
| Pvtic | gaatcattttctaaaacaataca tttgacaattaatcatcgcggctc gtataatgatcggctgaaattaat gaggtcatacccaaat | 55 |

Cell growth and bulk fluorescence measurements: For the fluorescence experiments, frozen stocks of the strains were used to inoculate 5 ml of LB medium containing 25 mg l$^{-1}$ chloramphenicol and incubated at 37° C. with an orbital shaking of 250 r.p.m. Overnight cultures were used to inoculate (0.1% volume/volume) an M9 salt medium containing 25 mg l$^{-1}$ chloramphenicol, 20 g l$^{-1}$ glucose, and 5 g l$^{-1}$ yeast extract. The M9 salt medium (Sigma-Aldrich) contains 6.78 g l$^{-1}$ Na$_2$HPO$_4$, 3 g l$^{-1}$ KH$_2$PO$_4$, 0.5 g l$^{-1}$ NaCl, 1 g l$^{-1}$ NH$_4$Cl, 0.1 mM CaCl$_2$), and 2 mM MgSO$_4$. 200 µl cultures of each strain (in triplicates) were loaded into black 96-well plates (black polystyrene plates with flat pclear bottom from Greiner Bio-One) and covered with Breathe-Easier sealing membrane (Sigma).

The cultures were grown until mid-log phase at 37° C. and 250 rpm. The mid-log phase cells were induced with phenolics such as vanillin, coumaric acid, and vanillic acid at varying concentrations. The induced cells were incubated in a plate reader (Tecan Infinite 200 Pro) at 30° C. and a 3 mm shaking amplitude. The optical density of the cultures and the mCherry fluorescence was monitored at required intervals in the plate reader. Cell density was measured by monitoring the absorption of the cultures at 600 nm (OD600). Fluorescence was recorded using an excitation wavelength of 575±9 nm and an emission wavelength of 610±20 nm with a manual gain of 100 and a Z-position of 20,000 µm. Fluorescence readings are reported as normalized fluorescence given by the ratio of fluorescence of the cells to the OD600. The fold changes were reported as the ratio of fluorescence level of the strain with engineered promoter to the strain with the basal promoter.

Flow cytometric analysis: Flow cytometric measurements were performed to study the heterogeneity amongst the *E. coli* cell population. The cells were transferred to a BD Accuri® C6 Flow Cytometer® (Accuri Cytometers, Ann Arbor, Mich.) 24 h after induction with either vanillin or coumaric acid. The fluorescence emission from the cells was detected from all detector positions, and to study the expression of mCherry (Em$_{max}$=610 nm), the signal from standard FL3 long-pass filter was utilized (see, e.g., Dinkelmann M et al., "Expanding fluorescence detection options with the Accuri® C6 Flow Cytometer® System," *Nat. Methods* 2010; 7(9):768 (2 pp.)).

In addition, data were collected for the cells from forward scatter (FSC) and side scatter (SSC) channels. For all measurements, a flow rate of 14 µl min$^{-1}$ was employed, corresponding to a core size of 10 µm. Calibrations were performed for scatter and fluorescence intensity using a set of fluorescently doped polystyrene beads with varying diameter (2.0, 7.52, 9.7, and 15.41 µm diameter) suspended in filter sterilized (0.22 µm, Millipore) de-ionized water (see, e.g., Davis R W et al., "Multiplex fluorometric assessment of nutrient limitation as a strategy for enhanced lipid enrichment and harvesting of *Neochloris oleoabundans*," *Biotechnol. Bioeng.* 2012; 109(10):2503-12; and Shapiro H M (ed.), *Practical flow cytometry* (4th ed.), John Wiley & Sons, Inc. (Hoboken, N.J.), July 2003 (736 pp.)). The primary threshold for an event was adjusted to a signal intensity value of 10,000 on FSC-H. Measurements were collected in triplicates from approximately 70×10$^3$ cells per well to ensure statistical significance. The data generated by the flow cytometer were plotted and analyzed with FlowJo V7.

Example 4: Diversification of Synthetic Biology Tools with Phenolics-Inducible Synthetic Promoters Lignin, an alkyl-aromatic polymer comprising 15-40% weight of the plant biomass, is generated in large quantities as a byproduct from the pulp and paper industry and also from the second-generation biofuel industry (see, e.g., Bruijnincx P C A et al., "Biomass conversion: lignin up for break-down," Nat. Chem. 2014; 6(12):1035-6; and Cotana F et al., "Lignin as co-product of second generation bioethanol production from ligno-cellulosic biomass." *Energy Procedia* 2014; 45:52-60). Its rich aromatic carbon content makes it an attractive renewable resource for the production of valuable materials, chemicals, and alternatives to fossil fuels (see, e.g., Xia Q et al. "Direct hydrodeoxygenation of raw woody biomass into liquid alkanes," *Nat. Commun.* 2016; 7:11162 (10 pp.); Salvachúa D et al., "Towards lignin consolidated bioprocessing: simultaneous lignin depolymerization and product generation by bacteria," *Green Chem.* 2015; 17(11):4951-67; and Varanasi P et al., "Survey of renewable chemicals produced from lignocellulosic biomass during ionic liquid pretreatment," *Biotechnol. Biofuels* 2013; 6:14 (9 pp.)).

However, lignin has thus far been underutilized; the most common current application is combustion of the solid-phase residue for its thermal energy content (see, e.g., White R H, "Effect of lignin content and extractives on the higher heating value of wood," *Wood Fiber Sci.* 1987; 19(4):446-52). Lignin valorization based on lignin-degrading microbes and enzymes can contribute to more efficient and environmentally benign use of lignin for sustainable production of value-added chemicals (see, e.g., Salvachna D et al., *Green Chem.* 2015; 17(11):4951-67).

Lignin is highly recalcitrant to microbial attack due to the presence of phenylpropanoid aryl-C$_3$ units cross-linked via C—C and C—O bonds-its chemical heterogeneity further complicates the problem (see, e.g., Bugg T D H et al., "Pathways for degradation of lignin in bacteria and fungi," *Nat. Prod. Rep.* 2011; 28(12):1883-96). Metabolic pathway engineering is emerging as a successful route to valorize lignin for the production of valuable renewable chemicals such as vanillin and cis, cis-muconic acid, which can serve the food, flavor, plastic, and adhesive industries (see, e.g., Sainsbury P D et al., "Breaking down lignin to high-value chemicals: the conversion of lignocellulose to vanillin in a gene deletion mutant of *Rhodococcus jostii* RHA1," *ACS Chem. Biol.* 2013; 8(10):2151-6; Vardon D R et al., "Adipic acid production from lignin," *Energy Environ. Sci.* 2015; 8(2):617-28; and Wu W et al., "Lignin valorization: two hybrid biochemical routes for the conversion of polymeric lignin into value-added chemicals," *Sci. Rep.* 2017; 7:8420 (13 pp.)). Synthetic biology tools such as promoters, ribosome-binding sites, terminators, and ribozymes for the regulation of biological modules are some essential components for the development of an efficient metabolic engineering chassis for these applications (see, e.g., Yadav V G et al., "The future of metabolic engineering and synthetic biology: towards a systematic practice," *Metab. Eng.* 2012; 14(3): 233-41; and Blazeck J et al., "Promoter engineering: recent advances in controlling transcription at the most fundamental level," *Biotechnol. J.* 2013; 8(1):46-58).

One of the most promising route to increase flux for product synthesis is to regulate or increase protein expression at the transcriptional level (see, e.g., Blazeck J et al., *Biotechnol. J.* 2013; 8(1):46-58; Lee J W et al., "Systems metabolic engineering of microorganisms for natural and non-natural chemicals," *Nat. Chem. Biol.* 2012; 8(6):536-46; and Ajikumar P K et al., "Isoprenoid pathway optimization for taxol precursor overproduction in *Escherichia coli*," *Science* 2010; 330(6000):70-4). Promoter engineering enables discovery of additional synthetic promoter elements that lie beyond the endogenous promoters and allows tunable control of gene expression. Therefore, constructing novel synthetic promoters through promoter engineering is critical to aid lignin valorization efforts.

Promoters inducible by phenolics can provide the following advantages in a lignin valorization chassis (see, e.g., FIG. 1A): (1) the engineered pathway can be designed to be activated in the presence of a lignin depolymerization product and catalyze the conversion of the same phenolic compound into its product. This leads to the development of substrate-inducible systems; (2) external inducers such as IPTG or galactose are not required, reducing the overall process cost and the extra stress resulting from the external inducer (see, e.g., Hannig G et al., "Strategies for optimizing heterologous protein expression in *Escherichia coli*," *Trends Biotechnol.* 1998; 16(2):54-60); (3) with the development of multiple phenolic-inducible promoters, a dynamic regulatory system (see, e.g., FIG. 2A), can be developed. A dynamic regulatory system can avoid the buildup of toxic intermediates and saves carbon and energy for the cell which otherwise would be expended for protein synthesis, thereby, improving product yield, rate, and titer (see, e.g., Zhang F et al., "Design of a dynamic sensor-regulator system for production of chemicals and fuels derived from fatty acids," *Nat. Biotechnol.* 2012; 30(4):354-9; and Chubukov V et al., "Synthetic and systems biology for microbial production of commodity chemicals," *NPJ Syst. Biol. Appl.* 2016; 2:16009 (11 pp.)); and (4) a phenolic-inducible promoter is independent of operation conditions, unlike other promoters that are inducible by environmental factors such as pH and temperature (see, e.g., Chou C H et al., "Characterization of a pH-inducible promoter system for high-level expression of recombinant proteins in *Escherichia coli*," *Biotechnol. Bioeng.* 1995; 47(2):186-92; and Dunn M A et al., "Identification of promoter elements in a low-temperature-responsive gene (blt4.9) from barley (*Hordeum vulgare* L.)," *Plant Mol. Biol.* 1998; 38(4):551-64). Therefore, the system is more robust and provides flexibility in the selection of operation conditions.

In a prokaryotic promoter, the conserved hexameric −35 element (e.g., TTGACA) and the −10 element (e.g., TATAAT), also known as the Pribnow box, are the primary binding sites for the RNA polymerase (see, e.g., Pribnow D, "Bacteriophage T7 early promoters: nucleotide sequences of two RNA polymerase binding sites," *J. Mol. Biol.* 1975; 99(3):419-43; and Pribnow D, "Nucleotide sequence of an RNA polymerase binding site at an early T7 promoter," *Proc. Nat'l Acad. Sci. USA* 1975; 72(3):784-8). Improvement in promoter strength can be achieved by random mutagenesis of the entire promoter region (see, e.g., Alper H et al., "Tuning genetic control through promoter engineering," *Proc. Nat'l Acad. Sci. USA* 2005; 102(36):12678-83 (correction in *Proc. Nat'l Acad. Sci. USA* 2006; 103(8): 3006-7); and Nevoigt E et al., "Engineering promoter regulation," *Biotechnol. Bioeng.* 2007; 96(3):550-8), saturation mutagenesis of nucleotide spacer regions (see, e.g., Jensen P R et al., "The sequence of spacers between the consensus sequences modulates the strength of prokaryotic promoters," *Appl. Environ. Microbiol.* 1998; 64(1):82-7; De Mey M et al., "Construction and model-based analysis of a promoter library for *E. coli*: an indispensable tool for metabolic engineering," *BMC Biotechnol.* 2007; 7:34 (14 pp.); and Tornoe J et al., "Generation of a synthetic mammalian promoter library by modification of sequences spacing transcription factor binding sites," *Gene* 2002; 297(1-2):21-32), or through a hybrid promoter engineering approach (see, e.g., De Boer H A et al., "The tac promoter: a functional hybrid derived from the trp and lac promoters," *Proc. Nat'l Acad. Sci. USA* 1983; 80(1):21-5; Blazeck J et al., "Tuning gene expression in *Yarrowia lipolytica* by a hybrid promoter approach," *Appl. Environ. Microbiol.* 2011; 77(22):7905-14; and Blazeck J et al., "Controlling promoter strength and regulation in *Saccharomyces cerevisiae* using synthetic hybrid promoters," *Biotechnol. Bioeng.* 2012; 109(11): 2884-95).

Hybrid promoter engineering has resulted in the creation of powerful promoters that are being used by researchers around the world. $P_{tac}$, which was developed in 1983, was the first of the widely used hybrid promoters (see, e.g., De Boer H A et al., *Proc. Nat'l Acad. Sci. USA* 1983; 80(1): 21-5). In fact, $P_{tac}$ along with its derivatives $P_{trc}$ and $P_{tic}$ are still commonly used today after more than thirty years of its discovery (see, e.g., Brosius J et al., "Spacing of the −10 and −35 regions in the tac promoter: effect on its in vivo activity," *J. Biol. Chem.* 1985; 260(6):3539-41). The use of these promoters for the expression of heterologous proteins is routine for *Escherichia coli*, *Bacillus subtilis*, and *Synechocystis* 6803, among others (see, e.g., Lee B R et al., "Utilization of *Escherichia coli* tac promoter in *Bacillus subtilis*," *Biotechnol. Lett.* 1990; 12(12):925-30; Varman A M et al., "Metabolic engineering of *Synechocystis* sp. strain PCC 6803 for isobutanol production," *Appl. Environ. Microbiol.* 2012; 79(3):908-14; and Oxer M D et al., "High level heterologous expression in *E. coli* using the anaerobically-activated nirB promoter," *Nucleic Acids Res.* 1991; 19(11): 2889-92).

Hybrid promoters based on the assembly of enhancer element and core promoter fusions have been successfully employed to improve the transcription efficiency or enable novel promoter regulation in eukaryotic systems as well (see, e.g., Blazeck J et al., *Biotechnol. Bioeng.* 2012; 109 (11):2884-95; Madzak C et al., "Heterologous protein expression and secretion in the non-conventional yeast *Yarrowia lipolytica*: a review," *J. Biotechnol.* 2004; 109(1-2): 63-81; and Juven-Gershon T et al., "Rational design of a super core promoter that enhances gene expression," *Nat. Methods* 2006; 3(11):917-22). This further demonstrates hybrid promoter engineering to be a promising and an efficient promoter engineering strategy for applications beyond prokaryotes.

In this study, we have utilized a hybrid promoter engineering approach to create novel promoters that have improved gene expression in the presence of phenolics. The various aromatic compounds present in the lignin-rich liquor generated after the pretreatment of lignocellulosic biomass are listed in Table 4. Vanillin is one of the primary phenolic compounds explored as an inducer in this study, since it appears in majority of the streams generated from the lignin depolymerization (Table 4, see also, e.g., Harris E E et al., "Reaction of hardwood lignin with hydrogen," *J. Am. Chem. Soc.* 1938; 60(6):1467-70; Oasmaa A et al., "Catalytic hydrotreating of lignin with water-soluble molybdenum catalyst," *Energy Fuels* 1993; 7(3):426-9; Voitl T et al., "Oxidation of lignin using aqueous polyoxometalates in the presence of alcohols," *ChemSusChem* 2008; 1(8-9):763-9; Xiang Q et al., "Production of oxychemicals from precipitated hardwood lignin," *Appl. Biochem. Biotechnol.* 2001; 91(1):71-80; Villar J C et al., "Oxidation of hardwood kraft-lignin to phenolic derivatives with oxygen as oxidant," *Wood Sci. Technol.* 2001; 35(3):245-55; Varanasi P et al., "Survey of renewable chemicals produced from lignocellulosic biomass during ionic liquid pretreatment," *Biotechnol. Biofuels* 2013; 6:14 (9 pp.); Duan J et al., "Biodegradation of kraft lignin by a newly isolated anaerobic bacterial strain, *Acetoanaerobium* sp. WJDL-Y2," *Lett. Appl. Microbiol.* 2016; 62(1):55-62; Raj A et al., "Identification of low molecular weight aromatic compounds by gas chromatography-mass spectrometry (GC-MS) from kraft lignin degradation by three *Bacillus* sp.," *Int. Biodeterior. Biodegradation* 2007; 59(4):292-6; Sainsbury P D et al., "Breaking down lignin to high-value chemicals: the conversion of lignocellulose to vanillin in a gene deletion mutant of *Rhodococcus jostii* RHA1," *ACS Chem. Biol.* 2013; 8(10): 2151-6; Chen Y et al., "Kraft lignin biodegradation by *Novosphingobium* sp. B-7 and analysis of the degradation process," *Bioresour. Technol.* 2012; 123:682-5; and Reiter J et al., "Enzymatic cleavage of lignin β-O-4 aryl ether bonds via net internal hydrogen transfer," *Green Chem.* 2013; 15(5):1373-81).

Example 5: Construction of Hybrid Promoters Inducible by Phenolics

A biosensor was constructed to interrogate the activity of the promoter $P_{emrR}$ by introducing a gene coding mCherry downstream of it and expressed in the *E. coli* strain Mach1. In addition, to verify that the promoter was active under the experimental conditions for this study, the strain RIF01 (Table 2) expressing mCherry under the control of $P_{emrR}$ was tested in the presence of vanillin. Vanillin was chosen as the first phenolic compound to be explored; since it appears as a common substrate in most of the lignin, depolymerization methods employed (Table 4).

TABLE 4

Aromatic compounds generated from the depolymerization of lignin

| Method | Depolymerization agent | Lignin source | Major products |
| --- | --- | --- | --- |
| Catalytic | Cu-CrO | Hardwood lignin | Methanol, 4-n-propylcyclohexanol, 4-n-propylcyclohexanediol, and glycol |
|  | Mo | Kraft pine lignin | Phenol, cyclohexane, benzene, naphthalene, and phenanthrene |
|  | $H_3PMo_{12}O_{40}$ | Kraft lignin | Vanillin and methyl vanillate |
|  | $CuSO_4/FeCl_3$ | Yellow poplar wood chips | Vanillin, syringaldehyde, acetovanillone, and acetosyringone |
|  | CuO | Hardwood kraft lignin | Syringaldehyde, vanillin, syringic acid, and vanillic acid |
| Ionic liquid | [C2mim][OAc] at 160° C. | Kraft lignin, eucalyptus, switchgrass, pine | Guaiacol, vanillin, syringol, eugenol, and catechol |
| Microbial | *Aneurinibacillus aneurinilyticus* | Kraft lignin | Guaiacol, acetoguiacone, gallic acid, and ferulic acid |
|  | *Bacillus* sp. | Kraft lignin | Ferulic acid, 3,4,5 trimethoxy benzaldehyde, and t-cinnamic acid |
|  | *Rhodococcus jostii* RHA1 mutant | Wheat straw lignocellulose | Vanillin, 4-hydroxybenzaldehyde, and ferulic acid |
|  | *Novosphingobium* sp. B-7 | Kraft lignin | Ethanediol, p-hydroxybenzoic acid, and vanillic acid |
| Enzymatic | A β-O-4 linkage cleaving enzyme system (LigDFG) | Softwood alkali-lignin and hardwood alkali-lignin | Guaiacol, ferulic acid, eugenol, vanillin, and acetovanillone |

Hybrid promoter engineering in general involves the fusion of two promoters comprising different characteristics, resulting in either a promoter of higher strength or an optimal promoter tailored to perform a specific function. The first step in this work was to identify an appropriate endogenous promoter that exhibits gene regulation in the presence of phenolics. The basal promoter from which the hybrid promoters for this study were developed was identified from an earlier research conducted by Strachan et al. (see, e.g., Strachan C R et al., "Metagenomic scaffolds enable combinatorial lignin transformation," *Proc. Nat'l Acad. Sci. USA* 2014; 111(28):10143-8). Strachan and others interrogated the intergenic regions in *E. coli* leading to the discovery of the promoter $P_{emrR}$, which was found to be active in the presence of a few lignin derived monoaromatic compounds. In this study, towards diversifying the synthetic biology tools, three engineered promoters were constructed by swapping the spacer region of $P_{emrR}$ to increase heterologous protein production in the presence of phenolics. Additional details follow.

Figure 4A:
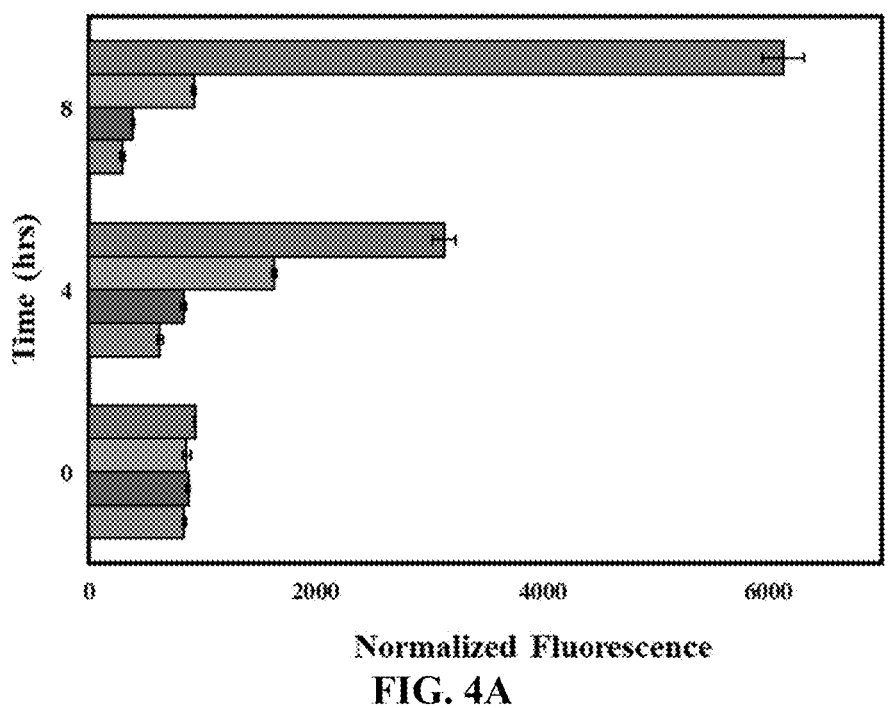
FIG. 4A-4B shows construction of hybrid promoter to increase the strength of induction by phenolics. Provided is a graph showing (A) identification of a basal promoter inducible by phenolics. The promoter $P_{emrR}$ is tested in the presence of vanillin by the expression of mCherry in E. coli and is found to be naturally inducible by vanillin that can be inferred by an increase in fluorescence at higher vanillin concentrations. For each time point, data bars are provided for induction with 0 mM, 0.1 mM, 1 mM, or 5 mM vanillin (from bottom to top). Each data bar represents the average of three biological replicates and the error bars represent standard deviation (s.d.). Also provided is a schematic showing (B) an exemplary hybrid promoter engineering strategy for the construction of higher strength promoters inducible by phenolics. Swapping the spacer region from any stronger promoter with a phenolic-inducible promoter may increase promoter strength but retain inducibility.

FIG. 4A confirms the induction of the promoter $P_{emrR}$ with the addition of vanillin. In the presence of 5 mM vanillin, the fluorescence of the RIF01 strain increased by over 20-fold in comparison with cultures without vanillin (FIG. 4A). Therefore, $P_{emrR}$ was selected as the basal promoter to be engineered for the construction of phenolic-inducible promoters of higher strength.

The strength of a promoter is primarily dependent on the similarity of the hexameric elements (−35 element and the −10 element) to the consensus sequence along with the length and sequence of the spacer region in between (see, e.g., Haugen S P et al., "Advances in bacterial promoter recognition and its control by factors that do not bind DNA," *Nat. Rev. Microbiol.* 2008; 6(7):507-19; and Ross W et al., "*Escherichia coli* promoters with UP elements of different strengths: modular structure of bacterial promoters," *J. Bacteriol.* 1998; 180(20):5375-83). The sequences upstream and downstream of the spacer region have been known to contain activator and repressor-binding sites to either enhance or repress transcription of a gene in some bacterial promoters (see, e.g., Nelson D L & Cox M M, *Lehning* principles of biochemistry (6th ed.), W. H. Freeman and Company (New York, N.Y.), 2013 (1328 pp.)).

Figure 4B:
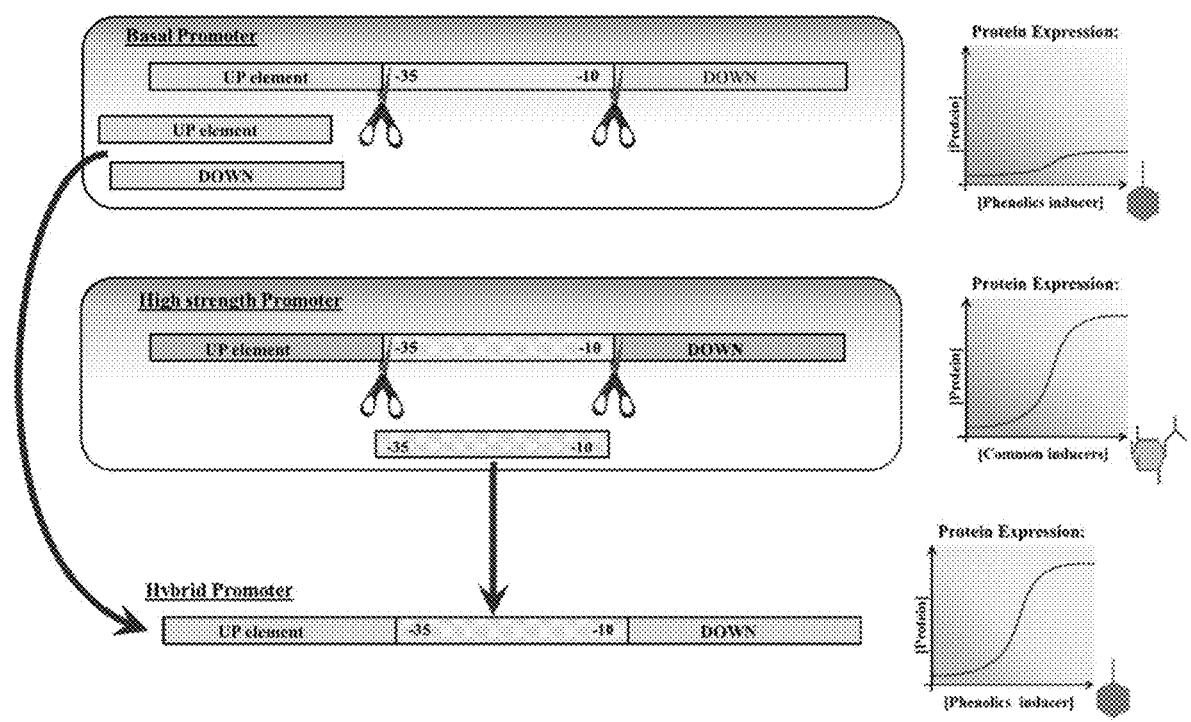

One of the previous successful efforts for engineering *E. coli* promoters involved fusing the enhancer element from different promoters to the core promoter of Pia resulting in transcription increase by 1.5-90-fold (see, e.g., Ross W et al., *J. Bacteriol.* 1998; 180(20):5375-83). However, given the lack of knowledge on the architecture of the endogenous promoter, $P_{emrR}$, it is prudent not to disturb these sites on the first trial as they may interact with the phenolics or a phenolic bound complex to modify transcription. The spacer provides flexibility for the binding of the sigma factor and mutagenesis of the spacer region has been successful in increasing transcription in several cases (see, e.g., Jensen P R et al., *Appl. Environ. Microbiol.* 1998; 64(1):82-7). Therefore, in this study as a new strategy to both diversify and increase the promoter strength, engineered promoters were created by importing the spacer regions from strong *E. coli* promoters and by fusing them with $P_{emrR}$ (FIG. 4B). The promoters $P_{tac}$, $P_{trc}$, and $P_{tic}$ were chosen to evaluate the effect of fusing their spacer regions into $P_{emrR}$. In addition, the three promoters differ from each other by one nucleotide and have varying levels of gene expression (i.e., the strength of $P_{tac} > P_{trc} > P_{tic}$) (see, e.g., Brosius J et al., *J. Biol. Chem.* 1985; 260(6):3539-41). This work can be used as a proof of concept for the construction of more diverse engineered promoters from the spacers of other *E. coli* promoters if the same order of gene expression can be observed among the three engineered promoters.

Example 6: Vanillin as an Inducer

Figure 5:
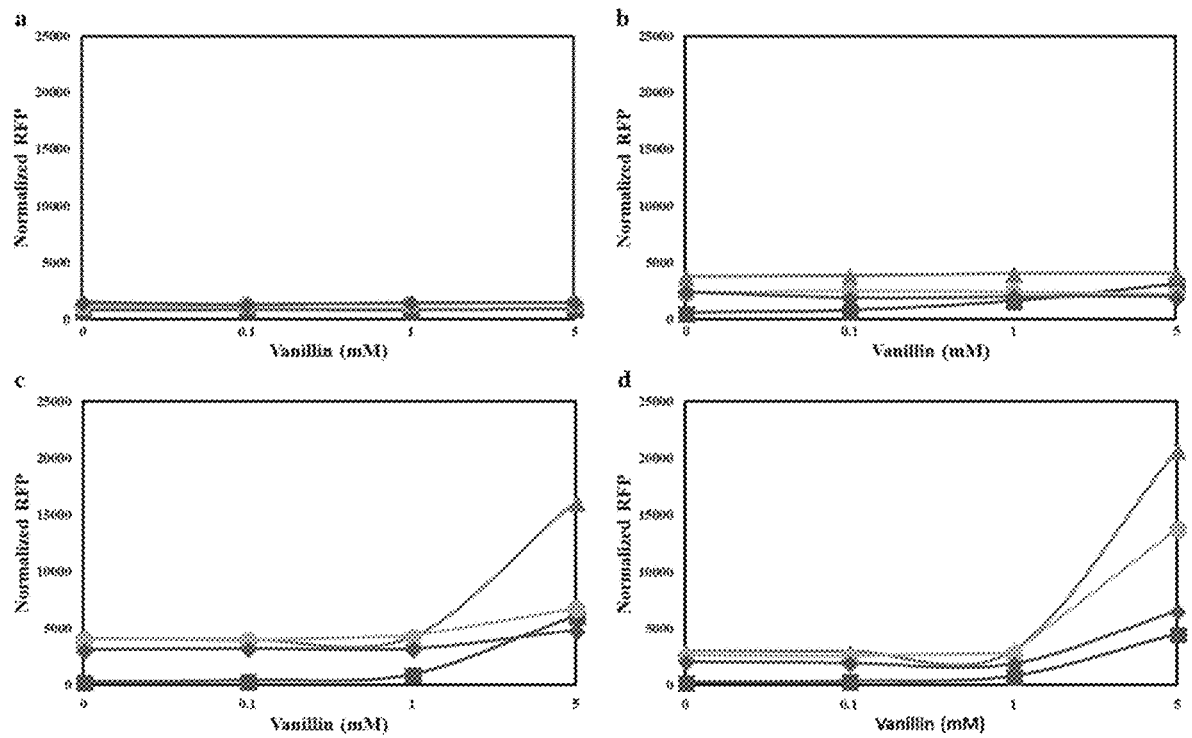
FIG. 5 shows performance of the engineered promoters in the presence of vanillin. Time after the addition of vanillin (inducer): a 0 h; b 4 h; c 8 h; and d 12 h. Gene expression is more prominent after 8 or 12 h after induction. The fluorescence of E. coli strains expressing mCherry under the native promoter $P_{emrR}$ and the engineered promoters $P_{vtac}$, $P_{vtrc}$, and $P_{vtic}$ were monitored using a fluorescence plate reader and normalized based on the cell density OD600. The cells were grown in an M9 salt medium containing 25 mg l$^{-1}$ chloramphenicol, 20 g l$^{-1}$ glucose, and 5 g l$^{-1}$ yeast extract at 30° C., and a 3 mm shaking amplitude. $P_{emrR}$, red squares; $P_{vtac}$, orange triangles; $P_{vtrc}$, grey circles; $P_{vtic}$, blue diamonds. Each data point represents the average of three biological replicates and the error bars represent s.d. The standard deviations between the biological replicates were too small for the error bars to be visible.

Engineered promoters $P_{vtac}$, $P_{vtrc}$, and $P_{vtic}$ were constructed utilizing the strategy discussed in the previous section. To evaluate the performance of the engineered promoters, strains RIF02, RIF03, and RIF04 were constructed that had mCherry expressing downstream of the promoters $P_{vtac}$, $P_{vtrc}$, and $P_{vtic}$, respectively. The fluorescence measured from the promoters demonstrated that RIF02 carrying the engineered promoter $P_{vtac}$ had the highest fluorescence 12 h after induction followed by the other strains with engineered promoters $P_{vtrc}$ and $P_{vtic}$ (FIG. 5). With respect to the control strain RIF01, the strains with the engineered promoters $P_{vtac}$, $P_{vtrc}$, and $P_{vtic}$ had an increase in fluorescence by 4.6, 3.0, and 1.5-fold, respectively, when induced with 5 mM vanillin. This finding showed good correlation with the strength of the IPTG-inducible promoters from which the spacer sequences were obtained, i.e., strength of $P_{vtac} > P_{vtrc} > $Pytic. This offers the possibility that incorporation of the spacer region from other *E. coli* promoters can enhance the strength of the phenolic-inducible promoter.

Fluorescence from the negative control strain, RIF00, containing an empty vector was 39-fold less in comparison with RIF01. This confirms that the background fluorescence from the culture due to the medium, vanillin, and *E. coli* is negligible. However, the experiment also revealed that the engineered promoters were highly leaky in comparison with $P_{emrR}$. Even in the absence of vanillin, the normalized fluorescence of the strains RIF02, RIF03, and RIF04 was higher than RIF01. Therefore, further engineering studies may be conducted on the flanking regions of the −10 and −35 motifs that may contain the activation and repression sites required to reduce the leaky expression of genes in the presence of engineered promoters.

Example 7: Promoter Activity with Other Phenolics

The study was further extended to other phenolics, including vanillic acid, coumaric acid, guaiacol, and syringate, by testing the strains RIF01, RIF02, RIF03, and RIF04 for their fluorescence emission. These phenolics were chosen, since they are closer in structure to vanillin, and at the same time, some of these compounds are also commonly present in the lignin depolymerized products, as listed in Table 4. However, not all of these phenolics were discovered to have gene regulation potential for the promoters that were tested.

Figure 6A:
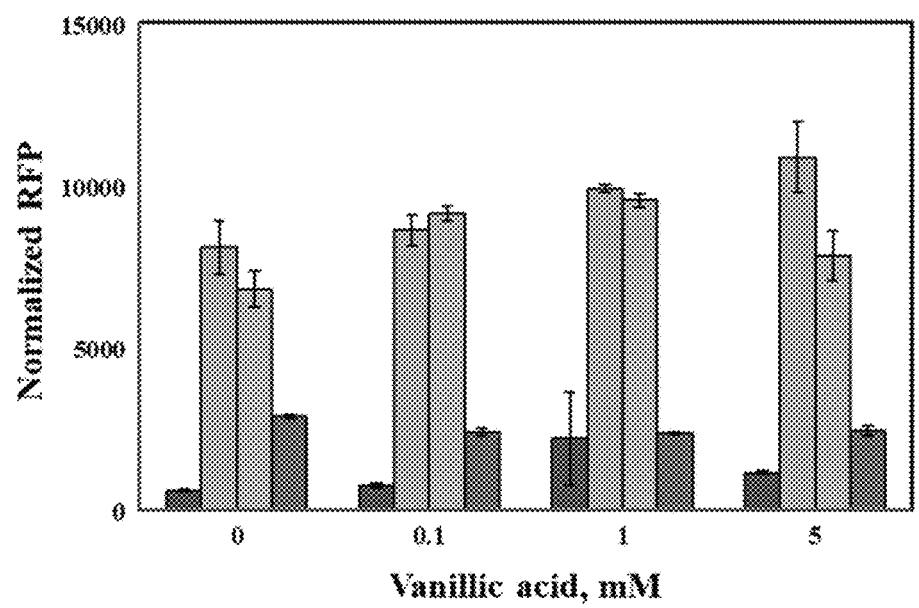
FIG. 6A-6B shows performance of the engineered promoters in the presence of (A) vanillic acid or (B) coumaric acid. The fluorescence of E. coli strains expressing mCherry under the native promoter $P_{emrR}$ and the engineered promoters $P_{vtac}$, $P_{vtrc}$, and $P_{vtic}$ were monitored after 24 h of induction using a fluorescence plate reader and normalized based on the cell density OD600. The cells were grown in an M9 salt medium containing 25 mg l$^{-1}$ chloramphenicol, 20 g l$^{-1}$ glucose, and 5 g l$^{-1}$ yeast extract at 30° C. and a 3 mm shaking amplitude. For each concentration of vanillin, data bars are provided for promoters $P_{emrR}$, $P_{vtac}$, $P_{vtrc}$, and $P_{vtic}$ (from left to right). Each data bar represents the average of three biological replicates and the error bars represent s.d.
Figure 7:
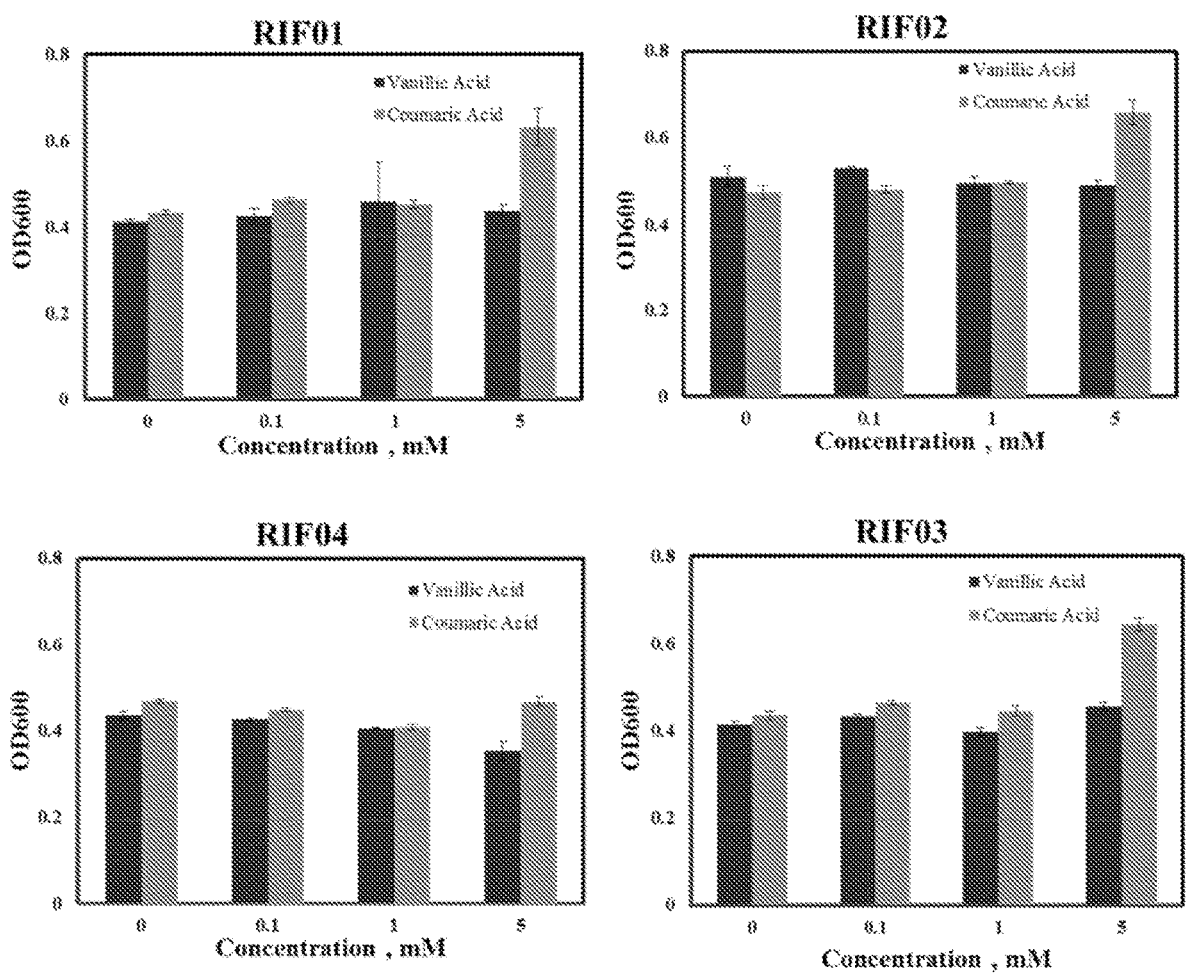
FIG. 7 shows optical density of the E. coli strains under varying concentrations of vanillic acid and coumaric acid. For each concentration, data bars are provided for vanillic acid (left) and coumaric acid (right).

Vanillic acid and coumaric acid had some level of induction; nevertheless, it took a long duration (24 h) for the induction effect to emerge. The longer duration required for the induction could possibly be due to the transport limitation of the phenolics across the cell wall in comparison with vanillin. In comparison with $P_{emrR}$, the engineered promoters $P_{vtac}$, $P_{vtrc}$, and $P_{vtic}$ resulted in the improvement of expression levels by 9.5-, 6.8-, and 2.1-fold, respectively, with the addition of 5 mM vanillic acid (FIG. 6A). Interestingly, the fluorescence at higher concentrations of vanillic acid and coumaric acid started to fall off slightly, especially for the strains engineered with the $P_{vtac}$ and $P_{vtrc}$ promoters despite no apparent drop in the OD600 of the cells at these concentrations. The OD600 of the cells at 24 h are shown in FIG. 7.

Figure 6B:
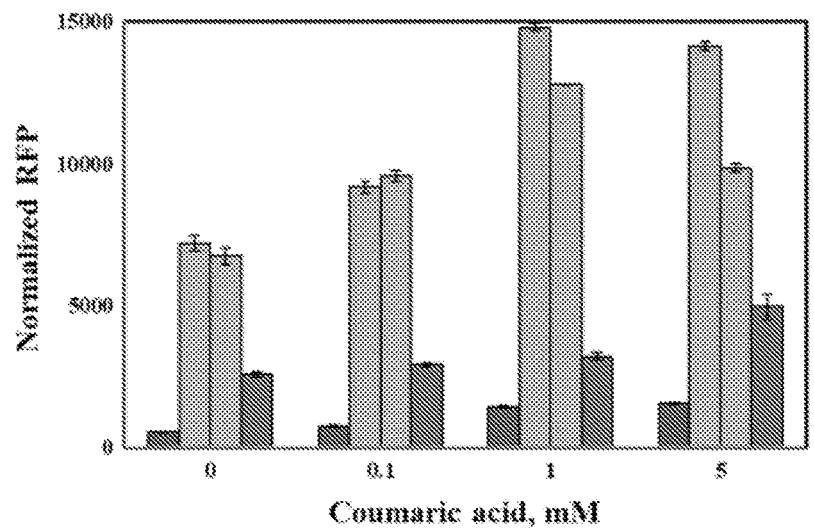

In the presence of 1 mM coumaric acid (FIG. 6B), the engineered promoters $P_{vtac}$ and $P_{vtrc}$ improved gene expression by 10.4- and 8.5-fold, respectively, whereas in the presence of 5 mM coumaric acid, the fold change for the promoters $P_{vtac}$ and $P_{vtrc}$ was 7.1 and 6.4, respectively, in comparison with $P_{emrR}$. In addition, the basal level of expression for mCherry was higher for the engineered promoters (i.e., high leaky expression in the absence of the inducers vanillic acid and coumaric acid). This experiment also demonstrates that the promoter is highly specific towards vanillin and engineering the UP element of the promoter may result in altered specificity towards other phenolics.

Example 8: Flow Cytometric Analysis of the Cell Population

The fluorescence results discussed thus far were obtained from a microplate reader and these values are not representative of the entire cell population, but an average behavior of all the cells. However, heterogeneity in gene expression can be present in the cell population due to several reasons. For example, a difference in gene expression may result among the cells due to either cell differentiation or morphogenesis (see, e.g., Tracy B P et al., "Flow cytometry for bacteria: enabling metabolic engineering, synthetic biology and the elucidation of complex phenotypes," *Curr. Opin. Biotechnol.* 2010; 21(1):85-99).

Identifying population heterogeneity can help identify variables that negatively impact the gene expression and thereby aid in the development of robust expression systems. Flow cytometry is a technique that allows for the measurement of multiple physical and biological properties of single cells. Therefore, to analyze the heterogeneity within the cell population resulting from the induction of the promoters by phenolics, flow cytometry was employed in this study.

Figure 8A:
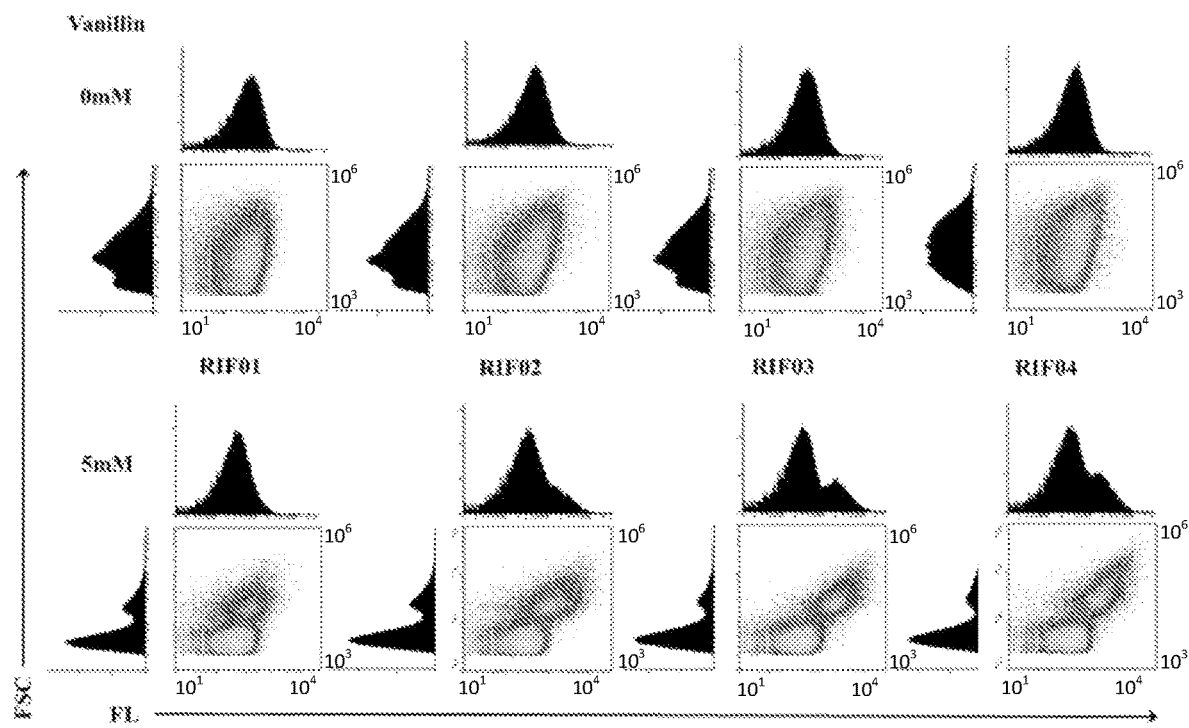
FIG. 8A-8B shows flow cytometric analysis of vanillin-induced cultures. E. coli strains RIF01, RIF02, RIF03, and RIF04 contained promoters $P_{emrR}$, $P_{vtac}$, $P_{vtrc}$, and $P_{vtic}$, respectively, for the expression of mCherry. Fluorescence (FL) was used as a measure of promoter strength, and forward scattering (FSC) was used as a measure of cell size. Provided are data for (A) strains induced with 0 mM or 5 mM of vanillin and (B) strains induced with 0 mM, 0.1 mM, 1 mM, 3 mM, or 5 mM of vanillin.
Figure 8B:
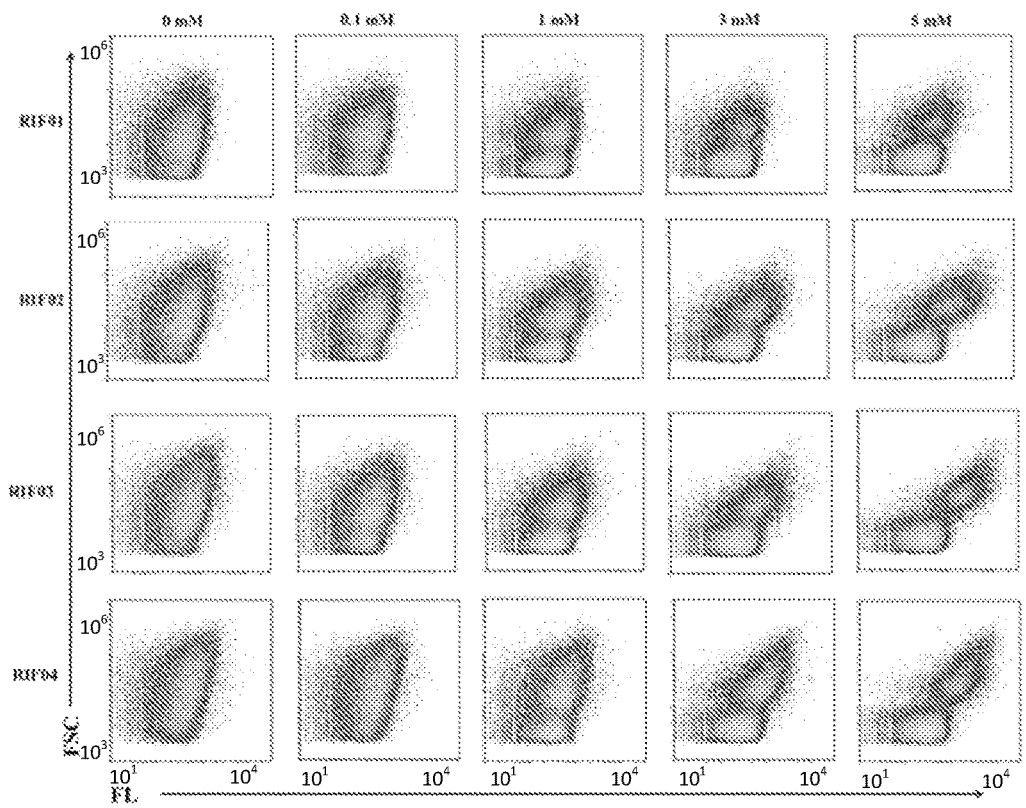
Figure 9A:
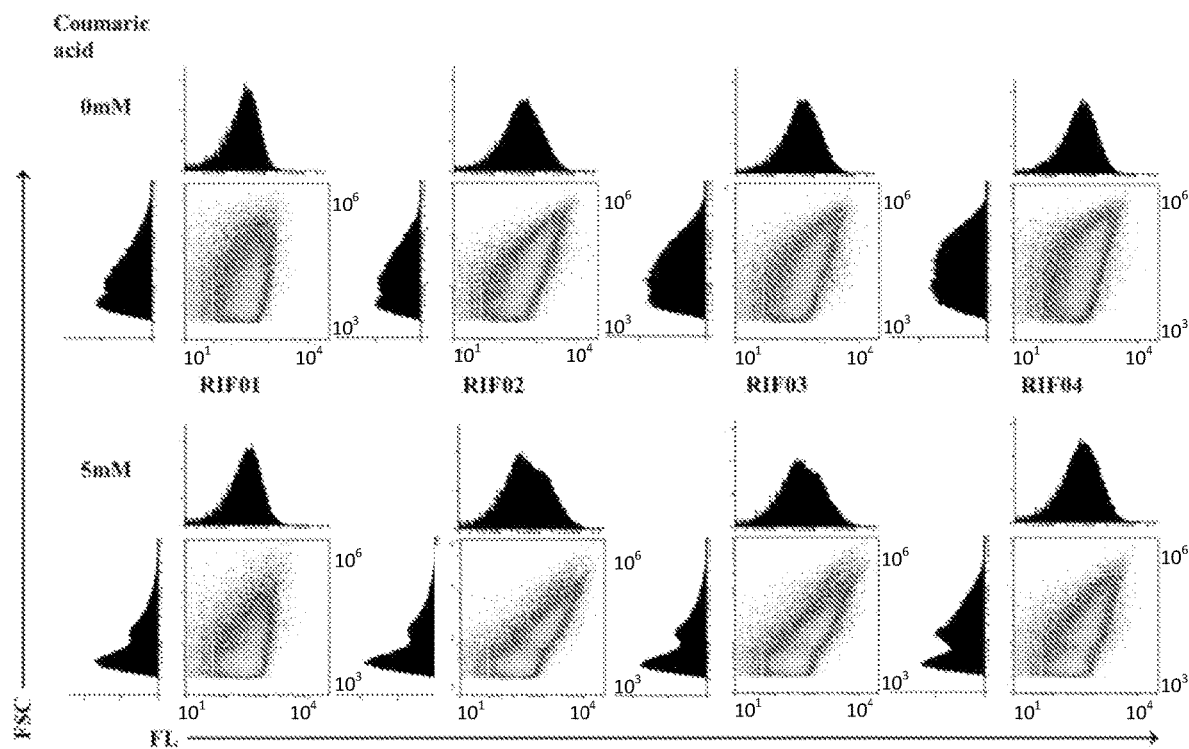
FIG. 9A-9B shows flow cytometric analysis of coumaric acid-induced cultures. E. coli strains RIF01, RIF02, RIF03, and RIF04 contained promoters $P_{emrR}$, $P_{vtac}$, $P_{vtrc}$, and $P_{vtic}$, respectively for the expression of mCherry. Fluorescence (FL) was used as a measure of promoter strength, and forward scattering (FSC) was used as a measure of cell size. Provided are data for (A) strains induced with 0 mM or 5 mM of coumaric acid and (B) strains induced with 0 mM, 0.1 mM, 1 mM, or 5 mM of coumaric acid.
Figure 9B:
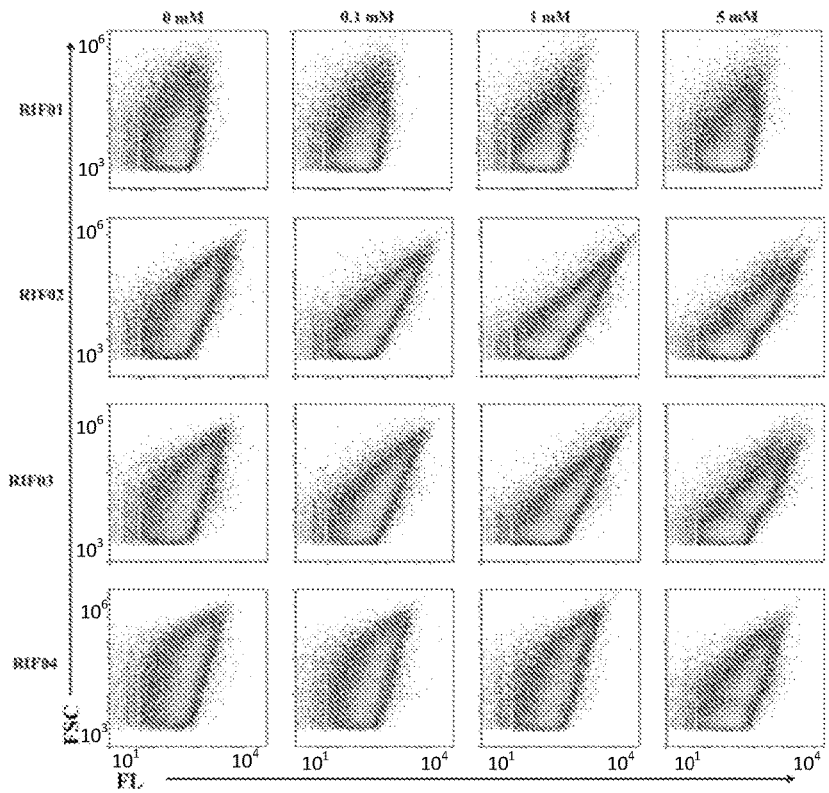

Vanillin and coumaric acid-induced cultures were analyzed 24 h after induction for their fluorescence and light-scattering intensities with a flow cytometer. While intensity of fluorescence can be used as inference for protein levels, forward scattering can be used as a measure for the size of the bacterial cell. The correlation between forward scattering and fluorescence intensities among the different strains of *E. coli* with variation in inducer concentration are shown for vanillin as the inducer (FIG. 8A-8B) and coumaric acid as the inducer (FIG. 9A-9B).

In agreement with our previous findings, the strains with the engineered promoters have a cell population that fluoresces much higher than the control strain, RIF01. In addition, a distinct sub-population of cells with higher forward scattering and higher fluorescence appeared for cultures that were induced with high concentrations of vanillin (greater than 1 mM vanillin). Light-scattering intensity has been considered to be roughly proportional to relative cell size and it has been observed that stationary phase cultures have a decreased cell size in comparison with exponential phase cultures (see, e.g., Akerlund T et al., "Analysis of cell-size and DNA content in exponentially growing and stationary-phase batch cultures of *Escherichia coli*," *J. Bacteriol.* 1995; 177(23):6791-7). A sub-population with lower forward scattering contained only background fluorescence, likely corresponding to the stationary phase cells with lower relative cell size. Interestingly, majority of the increase in fluorescence resulting from the engineered promoters was observed to come from the sub-population that had higher forward scattering.

Furthermore, the heterogeneity within the cell population was not observed for *E. coli* cells that were induced with IPTG (see, e.g., Balzer S et al., "A comparative analysis of the properties of regulated promoter systems commonly used for recombinant gene expression in *Escherichia coli*," *Microb. Cell Fact.* 2013; 12:26 (14 pp.)). With coumaric acid, although highly fluorescent cells had higher forward scattering, distinct sub-population did not appear as was the case with vanillin. To methodically identify the impact of promoter engineering on the heterogeneity of the cell population, the results were tabulated for cells with high forward scattering and high fluorescence for induction with vanillin (Table 5) or coumaric acid (Table 6).

TABLE 5

Vanillin-induced sub-population of cells with high fluorescence and forward scattering

| Strain | Concentration, mM | Cell population % (FL3-A >$10^3$) | Cell population % (FSC-A >$10^4$) |
| --- | --- | --- | --- |
| RIF01 | 0 | 2.91 ± 0.51 | 54.38 ± 4.47 |
|  | 0.1 | 2.87 ± 0.44 | 54.46 ± 1.65 |
|  | 1.0 | 2.09 ± 0.28 | 40.10 ± 2.17 |
|  | 3.0 | 2.22 ± 0.22 | 28.57 ± 0.48 |
|  | 5.0 | 5.18 ± 0.73 | 24.26 ± 2.98 |
| RIF02 | 0 | 8.62 ± 0.05 | 59.51 ± 1.67 |
|  | 0.1 | 6.37 ± 0.31 | 54.19 ± 2.99 |
|  | 1.0 | 7.08 ± 0.28 | 44.72 ± 1.97 |
|  | 3.0 | 8.68 ± 0.67 | 30.35 ± 0.56 |
|  | 5.0 | 13.52 ± 1.02 | 26.17 ± 2.44 |
| RIF03 | 0 | 7.81 ± 0.46 | 61.97 ± 0.41 |
|  | 0.1 | 6.21 ± 0.93 | 55.98 ± 1.29 |
|  | 1.0 | 6.48 ± 0.74 | 39.91 ± 1.73 |
|  | 3.0 | 8.58 ± 0.77 | 27.39 ± 0.47 |
|  | 5.0 | 16.89 ± 0.60 | 21.34 ± 0.50 |
| RIF04 | 0 | 7.61 ± 0.48 | 69.11 ± 0.39 |
|  | 0.1 | 7.21 ± 0.52 | 66.87 ± 0.72 |
|  | 1.0 | 7.48 ± 0.59 | 57.25 ± 2.04 |
|  | 3.0 | 15.67 ± 1.06 | 39.13 ± 2.03 |
|  | 5.0 | 18.22 ± 1.11 | 25.24 ± 1.21 |

TABLE 6

Coumaric acid induced sub-population of cells with high fluorescence and forward scattering

| Strain | Concentration, mM | Cell population % (FL3-A >$10^3$) | Cell population % (FSC-A >$10^4$) |
| --- | --- | --- | --- |
| RIF01 | 0 | 3.34 ± 0.15 | 53.49 ± 0.87 |
|  | 0.1 | 3.07 ± 0.01 | 44.25 ± 0.71 |
|  | 1.0 | 3.87 ± 0.26 | 36.46 ± 0.51 |
|  | 5.0 | 4.01 ± 0.44 | 35.23 ± 3.34 |
| RIF02 | 0 | 20.88 ± 1.12 | 55.27 ± 1.47 |
|  | 0.1 | 24.90 ± 0.58 | 46.40 ± 1.81 |
|  | 1.0 | 24.37 ± 0.99 | 37.67 ± 0.55 |
|  | 5.0 | 21.43 ± 1.05 | 34.60 ± 1.45 |
| RIF03 | 0 | 16.67 ± 1.88 | 57.80 ± 2.17 |
|  | 0.1 | 20.49 ± 0.2 | 48.20 ± 1.31 |
|  | 1.0 | 22.95 ± 0.71 | 39.70 ± 0.89 |
|  | 5.0 | 21.62 ± 1.28 | 37.90 ± 1.40 |
| RIF04 | 0 | 12.93 ± 0.92 | 65.47 ± 0.38 |
|  | 0.1 | 12.58 ± 0.86 | 61.27 ± 0.15 |
|  | 1.0 | 14.45 ± 0.97 | 55.90 ± 0.87 |
|  | 5.0 | 15.85 ± 2.35 | 47.37 ± 2.99 |

It can be verified from the tables that in the presence of 5 mM vanillin, the highly fluorescent cell population increased from 500 in RIF01 to between 13 and 1700 for the strains with engineered promoters (i.e., the strains RIF02, RIF03, and RIF04). However, the population of the cells with high forward scattering intensity remained about the same for all the promoters (i.e., between 24 and 27% of the total). These data suggest that there is no negative impact on the healthy and dividing cell population due to overexpression with the engineered promoters.

In addition, the high forward scattering intensity population decreased from between 50 and 70% in the absence of vanillin to between 24 and 27% with 5 mM vanillin. These data along with the presence of sub-population in FIG. 8A-8B suggest that vanillin stress is the likely cause for the observed heterogeneity. Therefore, the flow cytometry results suggest that the healthy population fraction needs to be maximized to achieve increased expression of the heterologous proteins.

Example 9: Promoter Strength with Variations in Temperature

Temperature is one fundamental parameter in controlling the productivity of microbial fermentations, since each microbial species have their optimal growth temperature and the optimal temperature for the heterologous enzyme being expressed may vary. In addition, for certain heterologous expressions, low-temperature fermentations may be preferred to ensure proper folding and thereby the function of the heterologous proteins (see, e.g., Baneyx F et al., "Recombinant protein folding and misfolding in *Escherichia coli*," *Nat. Biotechnol.* 2004; 22(11):1399-408; and Khow O et al., "Strategies for production of active eukaryotic proteins in bacterial expression system," *Asian Pac. J. Trop. Biomed.* 2012; 2(2):159-62). Therefore, to study the impact of operating temperatures on promoter strength, protein expression at two different operating temperatures, 25° C. and 37° C., was examined. The cells were incubated at either of these temperatures after induction with vanillin instead of 30° C. that was regularly employed.

Figure 10A:
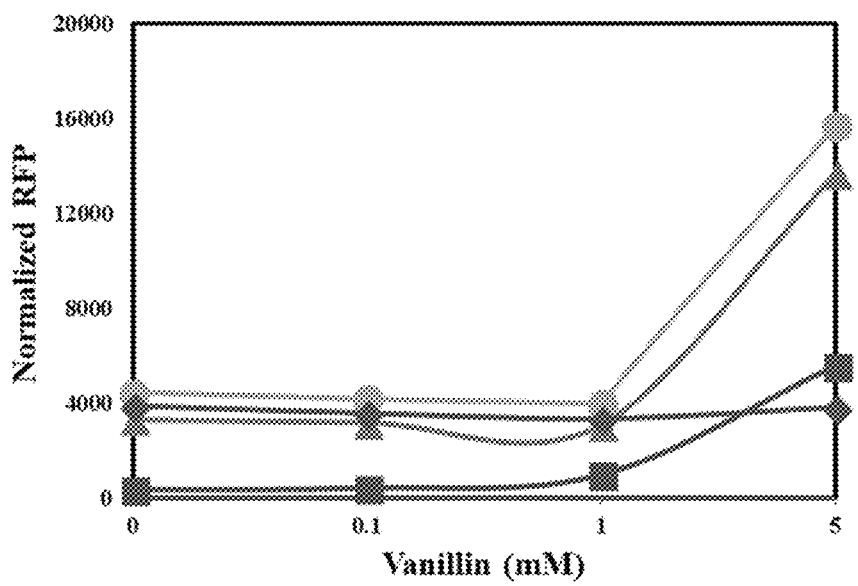
FIG. 10A-10B shows performance of the engineered promoters at two different temperatures: (A) 37° C. and (B) 25° C. The fluorescence of E. coli strains expressing mCherry under the native promoter $P_{emrR}$ and the engineered promoters $P_{vtac}$, $P_{vtrc}$, and $P_{vtic}$ were monitored after 8 and 24 h of induction at 37° C. and 25° C., respectively, using a fluorescence plate reader and normalized based on the cell density—OD600. The cells were grown in an M9 salt medium containing 25 mg l$^{-1}$ chloramphenicol, 20 g l$^{-1}$ glucose, and 5 g l$^{-1}$ yeast extract at the corresponding temperatures and a 3 mm shaking amplitude. $P_{emrR}$, red squares; $P_{vtac}$, orange triangles; $P_{vtrc}$, grey circles; $P_{vtic}$, blue diamonds. Each data point represents the average of three biological replicates and the error bars represent s.d. The standard deviations between the biological replicates were too small for the error bars to be visible.
Figure 10B:
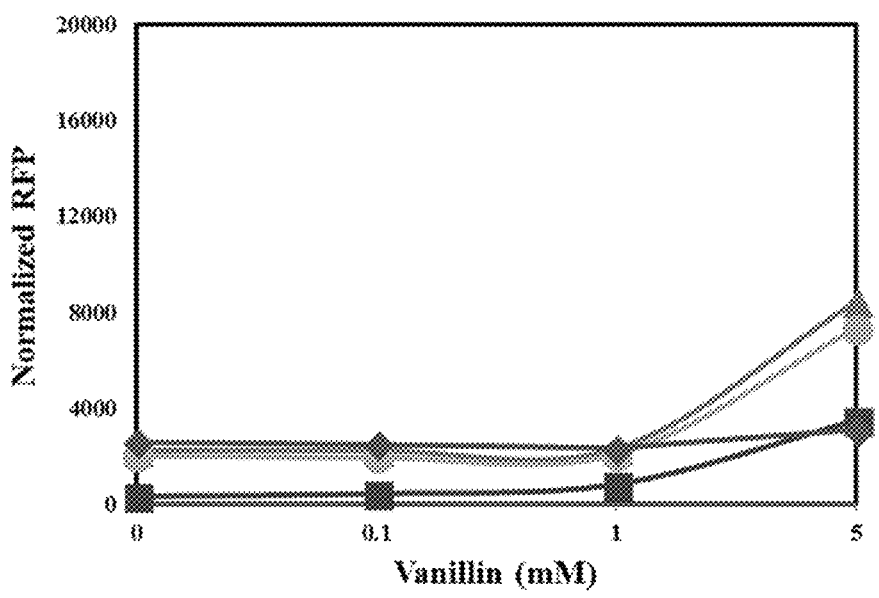

From FIG. 10A-10B, it can be verified that the inducibility profile with vanillin has been retained at both these temperatures and this offers flexibility in operating temperatures for employing these promoters. At 37° C., the mCherry expression profile obtained 8 h after induction (FIG. 10A)

was comparable to the data obtained at 30° C. (FIG. 5). However, at 25° C., the maximum normalized RFP values were reduced by half and were observed only 24 h after induction (FIG. 10B). Without wishing to be limited by mechanism, this is likely due to the reduced growth rate of E. coli at lower temperatures.

These experiments reveal that a change in temperature does not necessarily impact the intensity of the expression strength for these promoters. Therefore, the microbial systems developed for lignin valorization with such engineered promoters can be operated at temperatures that are optimal for the microbe and the heterologous protein under study. We also envision that this work will serve as a springboard for the development of more promoters that will be inducible by a variety of other phenolics generated from lignin depolymerization and their subsequent deployment towards the development of an efficient lignin valorization chassis.

Example 10: Further Directions

As described herein, to demonstrate the strategy of swapping spacer region to modulate promoter strength while retaining inducibility, we have constructed three different phenolic-inducible promoters from a basal promoter. To our knowledge, this is the first research work that focuses exclusively on the development of promoters inducible by lignin-derived phenolics. By employing a hybrid promoter-engineering approach, three different engineered promoters were constructed by incorporating the spacer region of higher strength endogenous promoters in E. coli. In the subsequent experiments, we demonstrated that this engineering strategy resulted in significant improvements in the strength of the hybrid promoters. Therefore, this strategy should be generally applicable for improving the strength of engineered promoters by incorporating spacer regions from other high strength promoters.

Furthermore, the strategy may also be employed to improve or diversify the strength of promoters that are inducible by other chemicals and factors. However, the engineered promoters were observed to be highly leaky, and therefore, reducing the leakiness of the promoters may require further engineering of the regions upstream and downstream of the −10 and −35 elements. The promoters were also observed to have a very long response time in the presence of vanillic acid and coumaric acid. We hypothesize that this could possibly be due to limitation in the transport of phenolics across the cell membrane. Therefore, studies on transporters and engineering host cells with transporters are critical for the development of an efficient microbial lignin valorization system.

Flow cytometry was employed to identify any heterogeneity in the cell population after induction with phenolics. The emergence of a sub-population constituting the metabolically active and dividing cells was observed especially in the cultures that were induced with 5 mM vanillin. In addition, this sub-population was identified as the major contributor for the heterologous protein that was expressed by the addition of phenolics as inducers. Therefore, further research effort will be required to increase the fitness of the strains in the presence of the phenolics which are known growth inhibitors at moderate-to-high concentrations. This aim can be achieved, e.g., by applying the following techniques: (1) utilizing a rich media; (2) evolving the strains to improve their growth in the presence of the phenolics; and (3) engineering the strains with stress tolerance genes. This study should stimulate expansion of promoter engineering efforts to utilize cheap chemicals present in lignocellulosic biomass hydrolysates as inducers, potentially eliminating the need for common supplemental inducers (e.g., such as IPTG, arabinose, etc.).

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A phenolic-inducible synthetic promoter comprising a spacer region, wherein the spacer region comprises:
   a first element comprising a nucleic acid sequence having at least 80% sequence identity to any one of SEQ ID NOs: 22-25;
   a second element comprising a nucleic acid sequence having at least 80% sequence identity to any one of SEQ ID NOs: 26-33; and
   a third element comprising a nucleic acid sequence having at least 80% sequence identity to any one of SEQ ID NOs: 34-37;
   wherein the promoter comprises a nucleic acid sequence having at least 98% sequence identity to any one of SEQ ID NOs: 1-9.

2. The synthetic promoter of claim 1, further comprising:
   an element upstream of the first element, wherein the element comprises a nucleic acid sequence having at least 80% sequence identity to any one of SEQ ID NOs: 10-21.

3. The synthetic promoter of claim 1, further comprising:
   an element downstream of the third element, wherein the element comprises a nucleic acid sequence having at least 80% sequence identity to any one of SEQ ID NOs: 38-42.

4. An expression cassette comprising:
   (i) a phenolic-inducible synthetic promoter, wherein the synthetic promoter comprises a spacer region, wherein the spacer region comprises:
      a first element comprising a nucleic acid sequence having at least 80% sequence identity to any one of SEQ ID NOs: 22-25;
      a third element comprising a nucleic acid sequence having at least 80% sequence identity to any one of SEQ ID NOs: 34-37; and
      a second element comprising a variable nucleic acid sequence disposed between the first and third elements; and
   (ii) a gene operably linked to the synthetic promoter, wherein the gene encodes a first protein that interacts with a first phenolic compound;
   wherein the promoter comprises a nucleic acid sequence having at least 98% sequence identity to any one of SEQ ID NOs: 1-9;
   wherein the first phenolic compound comprises a structure of formula (I) or a salt thereof or an anionic form thereof;

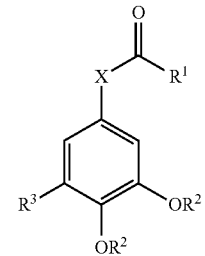

in which X is a bond, an optionally substituted alkylene, an optionally substituted alkenylene, or an optionally substituted heteroalkylene R₁ is H, optionally substituted alkyl, optionally substituted alkoxy, optionally substituted alkanoyl, carboxyaldehyde, carboxyaldehydealkyl, hydroxyl, hydroxyalkyl, thiol, thioalkoxy, or carboxyalkyl; each of $R_2$ is, independently, H or optionally substituted alkyl; and $R_3$ is H, optionally substituted alkyl, optionally substituted alkoxy, optionally substituted alkanoyl, or hydroxyl.

5. The expression cassette of claim 4, wherein the first phenolic compound induces the synthetic promoter.

6. The expression cassette of claim 5, wherein the first phenolic compound comprises vanillin, vanillic acid, ferulic acid, coumaric acid, syringaldehyde, syringate, or protocatechuate or a salt thereof or an anionic form thereof.

7. The expression cassette of claim 4, wherein the first protein comprises alcohol dehydrogenase, aldehyde dehydrogenase, protocatechuate decarboxylase, benzaldehyde dehydrogenase, benzaldehydederivatives dehydrogenase, catechol dioxygenase, 20 catechol 1,2-dioxygenase, coumarate transporter, DesA-syringate O-demethylase, DesB-gallate dioxygenase, DesV dehydrogenase or benzaldehyde dehydrogenase, 3-0-25 methylgallate 3,4-dioxygenase, decarboxylase subunit, noyl-CoAhydratase or phydroxycinnamoyl-CoA hydratase/lyase, feruloyl-CoA synthetase, feruloyl-CoA synthetase, feruloyl-CoA hydratase/lyase, feruloyl-CoA hydratase/lyase, FerC, ferulic acid decarboxylase, 3-hydroxyacyl-CoA dehydrogenase, hydroxylase, choline dehydrogenase or a β-hydroxypropiovanillone (HPV) oxidase, protocatechuate 4,5-dioxygenase, protocatechuate 4,5-dioxygenase, 4-carboxy-2-hydroxymuconate-6-semialdehyde (CHMS) dehydrogenase, C-α-dehydrogenase, β-etherase or a glutathione S-transferase (GSTase), β-etherase or a GSTase, glutathione lyase, 10-formyltetrahydrofolate synthetase, 2-pyrone-4,6-dicarboxylate (PDC) hydrolase, 4-oxalomesaconate (OMA) hydratase, 4-carboxy-4-hydroxy-2-oxoadipate (CHA) aldolase, C-α-dehydrogenase, 3-0-methylgallate-O-demethylase, C-α-dehydrogenase, C-α-dehydrogenase, β-etherase, tautomerase or an OMA tautomerase, vanillin dehydrogenase, decarboxylase or 5-carboxyvanillate decarboxylase, decarboxylase or a 5-carboxyvanillate decarboxylase, 5,5'-dehydrodivanillate (DDVA) O-demethylase component, hydrolase or a 2,2', 3-trihydroxy-3'-methoxy-5,5'-dicarboxybiphenyl (OHDDVA) meta-cleavage compound hydrolase, dioxygenase, or a OH-DDVA dioxygenase, gallate decarboxylase or 3-octaprenyl-4-hydroxybenzoate carboxy-lyase, lignostilbene dioxygenase, methylene folate reductase, protocatechuate decarboxylase, p-hydroxybenzoate-3-hydroxylase, p-hydroxybenzaldehyde synthase, p-hydroxybenzoate decarboxylase, (+)-DCA-C oxidase, (−)-DCA-C oxidase, p-hydroxycinnamoyl-CoA synthetase, p-hydroxycinnamoyl-CoA hydratase/lyase, pinoresinol/lariciresinol reductase, p-hydroxybenzoate hydroxylase, thiolase, vanillate-O-demethylase oxygenase subunit, vanillate-O-demethylase reductase subunit, or vanillin dehydrogenase, each as present in *E. coli*.

8. The expression cassette of claim 4, wherein the first protein comprises a C-α-dehydrogenase, a β-etherase, a dioxygenase, a hydrolase, an aromatic transporter, a vanillin dehydrogenase, or a feruloyl-CoA synthetase.

9. The expression cassette of claim 4, further comprising:
a second phenolic-inducible synthetic promoter, wherein the second phenolic-inducible synthetic promoter comprises a spacer region, wherein the spacer region comprises:
a first element comprising a nucleic acid sequence having at least 80% sequence identity to any one of SEQ ID NOs: 22-25;
a third element comprising a nucleic acid sequence having at least 80% sequence identity to any one of SEQ ID NOs: 34-37; and
a second element comprising a variable nucleic acid sequence disposed between the first and third elements; and
a second gene operably linked to the second synthetic promoter, wherein the second gene encodes a second protein that interacts with a second phenolic compound and wherein the second phenolic compound is a product of a reaction between the first phenolic compound and the first protein.

10. The expression cassette of claim 9, wherein the first phenolic compound comprises vanillin and the second phenolic compound comprises vanillate.

11. The expression cassette of claim 10, wherein the first protein comprises vanillin dehydrogenase as present in *E. coli*.

12. A recombinant gene comprising a phenolic-inducible synthetic promoter of claim 1.

13. A recombinant vector comprising an expression cassette of claim 1.

14. An isolated host cell comprising a modified gene that comprises a phenolic-inducible synthetic promoter of claim 1.

15. A method of treating lignin or a derivative thereof, the method comprising:
introducing to a source comprising lignin or a derivative thereof a host cell comprising a modified gene that comprises a phenolic-inducible synthetic promoter comprising a spacer region, wherein the spacer region comprises:
a first element comprising a nucleic acid sequence having at least 80% sequence identity to any one of SEQ ID NOs: 22-25;
a second element comprising a nucleic acid sequence having at least 80% sequence identity to any one of SEQ ID NOs: 26-33; and
a third element comprising a nucleic acid sequence having at least 80% sequence identity to any one of SEQ ID NOs: 34-37;
wherein the promoter comprises a nucleic acid sequence having at least 98% sequence identity to any one of SEQ ID NOs: 1-9.

16. The method of claim 15, wherein the source comprises one or more phenolic compounds, lignin, lignocellulose, or a lignin derivative.

17. The expression cassette of claim 4, wherein the second element comprises a nucleic acid sequence having at least 80% sequence identity to any one of SEQ ID NOs: 26-33.

18. The synthetic promoter of claim 1, wherein the promoter is characterized in *E. coli* and comprises SEQ ID NO: 6; wherein the first element is SEQ ID NO: 25, the second element is SEQ ID NO: 33; and the third element is SEQ ID NO: 37; further comprising intact full-length SEQ ID NO: 10 or SEQ ID NO: 39.

\* \* \* \* \*